US009732156B2

(12) United States Patent
Adamkewicz et al.

(10) Patent No.: US 9,732,156 B2
(45) Date of Patent: Aug. 15, 2017

(54) METHODS OF TREATING RHEUMATOID ARTHRITIS USING ANTIBODIES TO MATRIX METALLOPROTEINASE 9

(71) Applicant: Gilead Biologics, Inc., Foster City, CA (US)

(72) Inventors: Joanne I. Adamkewicz, Belmont, CA (US); Victoria Smith, Burlingame, CA (US); Zung Thai, Redwood City, CA (US); Michael J. Hawkins, San Francisco, CA (US)

(73) Assignee: Gilead Biologics, Inc., Foster City, CA (US)

( * ) Notice: Subject to any disclaimer, the term of this patent is extended or adjusted under 35 U.S.C. 154(b) by 630 days.

(21) Appl. No.: 13/781,662

(22) Filed: Feb. 28, 2013

(65) Prior Publication Data
US 2013/0224210 A1    Aug. 29, 2013

Related U.S. Application Data

(60) Provisional application No. 61/605,181, filed on Feb. 29, 2012, provisional application No. 61/755,444, filed on Jan. 22, 2013.

(51) Int. Cl.
| | | |
|---|---|---|
| C07K 16/40 | (2006.01) | |
| A61K 39/395 | (2006.01) | |
| A61K 45/06 | (2006.01) | |
| A61K 31/513 | (2006.01) | |
| A61K 39/00 | (2006.01) | |

(52) U.S. Cl.
CPC ............ *C07K 16/40* (2013.01); *A61K 31/513* (2013.01); *A61K 39/3955* (2013.01); *A61K 45/06* (2013.01); *A61K 2039/505* (2013.01); *A61K 2039/507* (2013.01); *C07K 2317/24* (2013.01)

(58) Field of Classification Search
None
See application file for complete search history.

(56) References Cited

U.S. PATENT DOCUMENTS

| | | | |
|---|---|---|---|
| 4,816,567 A | 3/1989 | Cabilly | |
| 5,545,806 A | 8/1996 | Lonberg et al. | |
| 5,545,807 A | 8/1996 | Surani et al. | |
| 5,569,825 A | 10/1996 | Lonberg et al. | |
| 5,625,126 A | 4/1997 | Lonberg et al. | |
| 5,633,425 A | 5/1997 | Lonberg et al. | |
| 5,661,016 A | 8/1997 | Lonberg et al. | |
| 7,101,975 B1 | 9/2006 | Brooks et al. | |
| 7,524,938 B2 | 4/2009 | Sagi et al. | |
| 7,566,449 B2 | 7/2009 | Brooks et al. | |
| 8,003,110 B1 * | 8/2011 | Rath | A61K 39/0011 424/185.1 |
| 8,377,443 B2 * | 2/2013 | McCauley | C07K 16/40 424/141.1 |
| 8,501,916 B2 | 8/2013 | McCauley et al. | |
| 9,120,863 B2 | 9/2015 | McCauley et al. | |
| 9,260,532 B2 | 2/2016 | McCauley et al. | |
| 9,550,836 B2 | 1/2017 | Smith et al. | |
| 2002/0159971 A1 | 10/2002 | Houde et al. | |
| 2004/0141982 A1 | 7/2004 | Lust et al. | |
| 2004/0175817 A1 | 9/2004 | Jepson et al. | |
| 2005/0287148 A1 | 12/2005 | Chatterjee et al. | |
| 2007/0172482 A1 | 7/2007 | Sagi et al. | |
| 2009/0186031 A1 | 7/2009 | Wood et al. | |
| 2009/0208510 A1 | 8/2009 | Sagi et al. | |
| 2009/0297449 A1 | 12/2009 | Devy | |
| 2009/0311245 A1 | 12/2009 | Devy et al. | |
| 2010/0098659 A1 * | 4/2010 | Watson | C12N 13/00 424/85.4 |
| 2012/0135004 A1 | 5/2012 | McCauley et al. | |
| 2013/0023654 A1 | 1/2013 | McCauley et al. | |
| 2013/0281675 A1 | 10/2013 | McCauley et al. | |
| 2015/0140580 A1 | 5/2015 | Smith et al. | |

FOREIGN PATENT DOCUMENTS

| | | |
|---|---|---|
| EP | 0 685 557 | 12/1995 |
| WO | WO-01/04157 | 1/2001 |
| WO | WO-02/066057 | 8/2002 |
| WO | WO-03/006006 | 1/2003 |
| WO | WO-03/044058 | 5/2003 |
| WO | WO-2004/022096 | 3/2004 |
| WO | WO-2004/076614 | 9/2004 |
| WO | WO-2006/037513 | 4/2006 |
| WO | WO-2007/005426 | 1/2007 |
| WO | WO-2007/094842 | 8/2007 |
| WO | WO-2007/144781 | 12/2007 |
| WO | WO-2008/088864 | 7/2008 |
| WO | WO 2008/102359 A1 | 8/2008 |

(Continued)

OTHER PUBLICATIONS

International Search Report and Written Opinion for PCT/US2013/028456 mailed Jul. 26, 2013.
International Search Report and Written Opinion for PCT/US11/49448, mailed Jun. 22, 2012.
International Preliminary Report on Patentability for International Patent Application No. PCT/US2011/049448, mailed Mar. 5, 2013.
Notice of Allowance in U.S. Appl. No. 13/219,523, mailed Oct. 10, 2012.
Notice of Allowance in U.S. Appl. No. 13/619,318, mailed Apr. 2, 2013.
International Search Report and Written Opinion for PCT/US2012/027160, mailed Nov. 8, 2012. 2012.
Angal et al., "A Single Amino Acid Substitution Abolishes the Heterogeneity of Chimeric Mouse/Human (IgG4) Antibody," Molec. Immunol. (1993) 30:105-108.
BioMosaics, Anti-Human Active Matrix Metalloproteinase 9 Antibody, Jul. 15, 2009, retrieved from the Internet Feb. 12, 2012: <http://www.biomosaics.com/pdfs/B2057M.pdf>.

(Continued)

*Primary Examiner* — Sharon Wen

(57) ABSTRACT

The present disclosure provides compositions and methods of use involving binding proteins, e.g., antibodies and antigen-binding fragments thereof, that bind to the matrix metalloproteinase-9 (MMP9) protein (MMP9 is also known as gelatinase-B), such as where the binding proteins comprise an immunoglobulin (Ig) heavy chain (or functional fragment thereof) and an Ig light chain (or functional fragment thereof).

20 Claims, 38 Drawing Sheets

(56) References Cited

FOREIGN PATENT DOCUMENTS

| | | |
|---|---|---|
| WO | WO-2008/154439 | 12/2008 |
| WO | WO-2009/022328 | 2/2009 |
| WO | WO-2009/111450 | 9/2009 |
| WO | WO-2009/111508 | 9/2009 |
| WO | WO-2010/048432 | 4/2010 |
| WO | WO-2010/059543 | 5/2010 |
| WO | WO-2011/092700 | 8/2011 |
| WO | WO-2012/027721 | 3/2012 |
| WO | WO-2013/130078 | 9/2013 |
| WO | WO 2013/130905 A1 | 9/2013 |

OTHER PUBLICATIONS

Boerner et al., "Production of Antigen-Specific Human Monoclonal Antibodies from in Vitro-Primed Human Splenocytes," J. Immunol. (1991) 147:86-95.

Carter, "Potent Antibody Therapeutics by Design," Nature Reviews Immunology, (2006) 6: 343-357.

Davies et al., "Affinity improvement of single antibody VH domains: residues in all three hypervariable regions affect antigen binding," Immunotechnology (1996) 2(3):169-179.

Fishwild et al., "High-Avidity Human IgGK Monoclonal Antibodies from a Novel Strain of Minilocus Transgenic Mice," Nature Biotechnology (1996) 14:845-851.

Holt et al., "Domain antibodies: proteins for therapy," Trends in Biotechnology (2003) 21(11): 484-490.

Hoogenboom et al., "By-Passing Immunisation Human Antibodies from Synthetic Repertoires of Germline VH Gene Segments Rearranged in Vitro," J. Mol. Biol. (1992) 227:381-388.

Hu et al., "Inhibitors of gelatinase B/matrix metalloproteinase-9 activity comparison of a peptidomimetic and polyhistidine with single-chain derivatives of a neutralizing monoclonal antibody," Biochem. Pharmacol. (2004) 67(5):1001-1009.

Hu et al., "Matrix Metalloproteinase Inhibitors as Therapy for Inflammatory and Vascular Diseases," Nature Reviews: Drug Discovery (2007) 6:480-498.

Jones et al., "Replacing the Complementarity-Determining Regions in a Human Antibody with Those from a Mouse," Nature (1986) 321:522-525.

Lonberg et al., "Antigen-Specific Human Antibodies from Mice Comprising Four Distinct Genetic Modifications," Nature (1994) 368:856-859.

Lonberg et al., "Human Antibodies from Transgenic Mice," Intern. Rev. Immunol. (1995) 13:65-93.

Marks et al., "By-Passing Immunization Human Antibodies from V-gene Libraries Displayed on Phage," J. Mol. Biol. (1991) 222:581-597.

Marks et al., "By-Passing Immunization: Building High Affinity Human Antibodies by Chain Shuffling," Bio/Technology (1992) 10:779-783.

Martens et al., "A Monoclonal Antibody Inhibits Gelatinase B/MMP-9 by Selective Binding to Part of the Catalytic Domain and Not to the Fibronectin or Zinc Binding Domains," Biochimica et Biophysica Acta (2007) 1770:178-186.

Morrison, "Success in Specification," Nature (1994) 368:812-813.

Nagase et al., "Structure and function of matrix metalloproteinases and TIMPs," Cardiovasc. Res. (2006) 69(3):562-573.

Neuberger, "Generating High-Avidity Human Mabs in Mice," Nature Biotechnology (1996) 14:826.

Presta, "Antibody Engineering," Curr. Op. Struct. Biol. (1992) 2:593-596.

Riechmann et al., "Reshaping Human Antibodies for Therapy," Nature (1988) 332:323-329.

Tochowicz et al., "Crystal structures of MMP-9 complexes with five inhibitors: contribution of the flexible Arg424 side-chain to selectivity," J. Mol. Biol. (2007) 371(4):989-1006.

Vector Laboratories, Product Specifications, Antibody to Matrix Metalloproteinase 9, 2004, retrieved from the Internet Feb. 12, 2012: <http://www.vectorlabs.com/data/protocols/VPM644.pdf>.

Verhoeyen et al., "Reshaping Human Antibodies: Grafting an Antilysozyme Activity," Science (1988) 239:1534-1536.

Visse et al., "Matrix metalloproteinases and tissue inhibitors of metalloproteinases: structure, function, and biochemistry," Circ. Res. (2003) 92(8):827-839.

Wark et al., "Latest technologies for the enhancement of antibody affinity," Advanced Drug Delivery Reviews (2006) 58(5-6): 657-670.

Zapata et al., "Engineering Linear F(ab')2 Fragments for Efficient Production in *Escherichia coli* and Enhanced Antiproliferative Activity," Protein Eng. (1995) 8(10):1057-1062.

Office Action dated Dec. 8, 2014 for Vietnamese Patent Application No. 1-2014-03178.

Office Action dated Nov. 7, 2014 for Panama Patent Application No. PI/2014/90332-01.

Office Action dated May 25, 2015 for New Zealand Patent Application No. 629178.

Office Action dated Aug. 4, 2015 for Columbian Patent Application No. 14-190-938.

Partial supplementary European search report dated Oct. 15, 2015 for European Patent Application No. 13754254.4.

Office Action dated Jul. 15, 2015 for Chinese Patent Application No. 201380022489.6.

Pruijt, et al., "Prevention of interleukin-8-induced mobilization of hematopoietic progenitor cells in rhesus monkeys by inhibitory antibodies against the Metalloproteinase gelatinase B (MMP-9)", Proc. Natl. Acad. Sci. USA (1999) 96:10863-10868.

Ramos-Desimone et al., "Inhibition of Matrix Metalloproteinase 9 Activation by a Specific Monoclonal Antibody", Hybridoma (1993) 12(4):349-363.

Rudikoff et al., "Single Amino Acid Substitution Altering Antigen-Binding Specificity", Proc. Natl. Acad. Sci. USA (1982) 79:1979-1983.

European Application No. 11820759.6, Extended European Search Report dated Feb. 27, 2015, 9 pages.

Australian Application No. 2011293125, Notice of Grant, dated May 21, 2015, 1 page.

Australian Application No. 2011293125, Office Action dated May 16, 2014, 4 pages.

Australian Application No. 2015201367, Office Action dated Nov. 30, 2015, 5 pages.

Australian Application No. 2012318302, Office Action dated Nov. 13, 2014, 3 pages.

Australian Application No. 2012318302, Office Action dated Nov. 6, 2015, 4 pages.

Australian Application No. 2013203619, Notice of Acceptance dated Feb. 12, 2015, 2 pages.

Australian Application No. 2013203619, Office Action dated Nov. 27, 2014, 3 pages.

Canadian Application No. 2808418, Office Action dated Jul. 20, 2015, 4 pages.

Canadian Application No. 2808418, Office Action dated Jun. 12, 2014, 3 pages.

Chilean Application No. 535-2013, First Office Action dated Feb. 25, 2013, 27 pages (and 38 page translation).

Chilean Application No. 535-2013, dated Apr. 17, 2015 for Chilean Patent Application No. 525-2013, 26 pages (and 36 page English translation).

Chilean Patent Application No. 2282-2014, Opposition mailed on Aug. 17, 2015, 3 pages (and Agent's summary).

Chinese Office Action mailed on Jun. 9, 2014, for Chinese Patent Application No. 201180041422.8, 5 pages (with English translation).

Chinese Office Action mailed on Nov. 5, 2013, for Chinese Patent Application No. 201180041422.8, 14 pages (with English translation).

Colombian Office Action for Patent Application No. 14-190.943, dated Jul. 7, 2015, 11 pages (with translation).

Colombian Application No. 13-36730-5, Office Action issued by Industry and Trade Superintendence, issued on Aug. 26, 2014, 2 pages and 9 page English translation.

(56) References Cited

OTHER PUBLICATIONS

Colombian Application No. 13-36730-5, Resolution No. 641 (Grant) issued by Industry and Trade Superintendence, issued on Jan. 15, 2015, 5 pages (with English translation).
Eurasian Application No. 201390146, First Office Action dated Apr. 18, 2015, 4 pages (with English translation).
European Application No. 12708473.9, Office Action issued by the European Patent Office, dated Jan. 18, 2016, 6 pages.
Indonesian Application No. W00201301191, Office Action reported Jun. 9, 2015, 4 pages (with English translation).
Israeli Application No. 224614, Notification Prior to Examination dated Dec. 28, 2014.
Notification of Defects in Israeli Patent Application No. 224614 issued by the Ministry of Justice, The Patent Office, dated Aug. 9, 2015, 3 pages (with translation).
Office Action issued for Thai Patent Application No. 1401005042, dated Sep. 16, 2015, 2 pages—Non-English with Agent summary (2 pages).
JP Application No. 2013-526186, Notice of the Grounds for Rejection mailed on Aug. 26, 2014, 10 pages (with English Translation).
Korean Application No. 10-2013-7007599, Office Action dated Oct. 31, 2014, 6 pages (with English translation).
Mexican Application No. MX/a/2014/010447, Office Action dated Jan. 23, 2015, 4 pages (with English translation).
New Zealand Application No. 606880, Office Action dated Nov. 18, 2014, 2 pages.
New Zealand Application No. 701444, Office Action dated Nov. 18, 2014, 3 pages.
Notice of Allowance issued by the United States Patent and Trademark Office for U.S. Appl. No. 13/935,352, dated Oct. 15, 2015, 5 pages.
Notice of Allowance for Chinese Application No. 201180041422.8, dated Oct. 10, 2014, 2 pages (Non-English) and (6 page Agent Report and allowed claims).
Office Action issued by the Japanese Patent Office for Application No. 2013526186, dated Jun. 23, 2015, 5 pages (with translation).
Office Action issued by the New Zealand Intellectual Property Office for Application No. 629888, dated May 25, 2015, 3 pages.
U.S. Appl. No. 13/935,352, Final Office Action mailed Jun. 26, 2015, 9 pages.
U.S. Appl. No. 13/935,352, Non-Final Office Action mailed Mar. 26, 2015, 7 pages.
U.S. Appl. No. 13/935,352, Non-Final Office Action mailed Oct. 14, 2014, 8 pages.
U.S. Appl. No. 13/935,352, Notice of Allowance mailed Feb. 2, 2016, 7 pages.
U.S. Appl. No. 13/935,370, First Notice of Allowance mailed Jan. 2, 2015, 11 pages.
U.S. Appl. No. 13/935,370, Second Notice of Allowance mailed May 20, 2015, 8 pages.
Ukrainian Application No. 201302088, Office Action dated Dec. 27, 2013, 6 pages (with English translation).
Ukrainian Application No. 201302088, Office Action dated Feb. 24, 2015, 7 pages (with English translation).
Vietnam Application No. 1-2014-03178, Office Action dated Dec. 18, 2014, 2 pages (with English translation).
Office Action issued by the African Regional Intellectual Property Organization (ARIPO), for application No. AP/P/2013/006743, dated Sep. 28, 2015—received Nov. 13, 2015, 7 pages.
Second Office Action issued by the Eurasian patent Office for Application No. 201390146/28, received Dec. 29, 2015, 2 pages (with Engl translation).
Notice of Reasons for Rejection issued by the Japanese Patent Office for Application No. 2014-559872, dated Dec. 15, 2015, 6 pages (and 9 page English translation).
Notification Prior to Examination issued by the Israeli Patent office for Application No. 234304, dated Jan. 24, 2016, 3 pages (translation).
Office Action issued by the New Zealand Intellectual Property Office for Application No. 629178, dated Jan. 12, 2016, 3 pages.
Extended European Search Report issued by the European Patent Office for Application No. 13754254.4, dated Feb. 4, 2016, 15 pages.
Communication issued by the European Patent Office for Application No. 13754254.4, dated Oct. 10, 2014, 3 pages.
Communication pursuant to Rules 161(1) and 162 (EPC) issued by the European Patent Office for Application No. 12708473.9, dated Nov. 25, 2014, 2 pages.
Response to Communication pursuant to Rules 161(1) and 162 (EPC) issued by the European Patent Office for Application No. 12708473.9, dated May 7, 2015, 1 page.
Non-Final Office Action issued by The United States Patent and Trademark Office for U.S. Appl. No. 13/781,662, dated Feb. 1, 2016.
Acceptance Letter for (Grant) for South African Patent Application No. 2014/06319, dated Jan. 8, 2016 (to issue Feb. 24, 2016), 1 page Agent letter.
Colombian Office Action for Application No. 14-190.938, dated Feb. 5, 2016, 10 pages (Agent's English translation).
Mexican Application No. MX/a/2013/002323, Office Action dated Feb. 24, 2016, 4 pages (and 6 page English translation).
Response to Second Office Action issued by the Eurasian patent Office for Application No. 201390146/28, dated Mar. 3, 2016, 20 pages (includes Engl claims).
Office Action Notice from Agent received Mar. 7, 2016 for Thai Patent Application No. 1401005043 (e-mail—3 pages and one page English document).
Communication pursuant to Rules 70(2) and 70a(2) EPC issued by the European Patent Office for Application No. 13754254.4, dated Feb. 23, 2016, 1 page.
Arguments filed on Mar. 14, 2016 for Japanese Application No. 2014-559872, 15 pages.
Office Action—Notification Prior to Exam issued by the Israeli Patent Office for Application No. 234263, dated Jan. 24, 2016, 3 pages
Office Action issued by the China State Intellectual Property Office for Application No. 201280072749.6, dated Mar. 2, 2016, 13 pages includes English translation (received May 16, 2016).
Office Action issued by the Colombian Patent Office for Application No. 14-190.938, dated Apr. 28, 2016, 21 pages (includes Agent's letter).
Office Action—94(3) communication—issued by the European Patent Office for Application No. 11820759.6 on May 17, 2016, 5 pages.
First Office Action issued by the Eurasian Patent Office for Application No. 201491575, received Jun. 28, 2016, 5 pages includes English translation.
Office Action (First) issued by the Ukrainian Patent Office for Application No. a201410545, received Jul. 15, 2016, four pages and 4 pages English translation.
Office Action (Second) issued by the China Patent Office for Application No. 201380022489.6, dated Apr. 21, 2016, 5 pages (English translation).
Office Action issued by Chilean Patent Office for Application No. 2258-2014, dated May 31, 2016 (17 pages) and (26 pages of English translations of Sections of Exam Report).
Office Action issued by the European Patent Office for Application No. 12708473.9, dated Jul. 12, 2016, 3 pages.
Office Action issued by the Philippines Patent Office for Application No. 1-2013-500347, dated Jun. 28, 2016, 3 pages.
Notice of Allowance issued by the Mexican Patent Office for Application No. MX/a/2013/002323, dated Jul. 12, 2016, 1 page non-English and one page Engl. translation.
Office action issued by the United States Patent and Trademark Office for U.S. Appl. No. 14/992,678, dated Aug. 2, 2016, 9 pages.
Office Action—Restriction Requirement—issued by the United States Patent and Trademark Office for U.S. Appl. No. 14/382,301, dated May 23, 2016, 8 pages.
Office Action Report for Chilean Patent Application No. 2282-2014, dated May 31, 2016, 17 pages Agent Summary in English.
Office Action—Notice of Ground for Rejection issued by the Japanese Patent Office for Application No. 2015-208653, dated Aug. 2, 2016, 5 pages Non-English and 4 pages English translation.

(56) References Cited

OTHER PUBLICATIONS

Office Action—Notice of Final Rejection issued by the Japanese Patent Office for Application No. 2014-559872, dated Jul. 25, 2016, 3 pages Non-English and 6 page English translation.
Office Action issued by the Thai Patent Office (Formalities Only) for Application 1401005043, 15 pages (Notice of Action only from Agent dated May 18, 2016 and Response Attached).
First Examination Report issued by the New Zealand Patent Office for Application No. 723630, dated Sep. 14, 2016, 2 pages.
Acceptance Notice from Agent re South African Patent Application No. 201406318, accepted on May 9, 2016 and Expected Advertisement Date : Jul. 27, 2016, dated Jun. 22, 2016, received Nov. 11, 2016.
Notice of Eligibility for Grant issued by the Intellectual Property Office of Singapore for Patent Application No. 11201405273Y, dated Oct. 21, 2016, 7 pages include allowed claims.
Office Action Notice of Preliminary Rejection (Non-Final) issued by the Korean Intellectual Property Office (KIPO), for Application No. 10-2014-7035325, dated Nov. 9, 2016, 12 pages includes English translation.
Office Action—Notice of Reasons for Rejection issued by the Japanese Patent Office for Application No. 2015-208653, dated Nov. 15, 2016, 7 pages including English translation.
Office Action issued by the Eurasian Patent Organization for Application No. 201491599/28, received Dec. 15, 2016, 1 page Non-English, 1 page English translation, and 5 pages of claims in English.
Office Action issued by the Intellectual Property Office of Singapore for Application No. 11201405305P, dated Nov. 29, 2016, 2 pages and 2 pages of claims.
Office Action—Further Examination Report—issued by the New Zealand Patent Office for Application No. 629888, dated Dec. 16, 2016, 2 pages.
Office Action issued for Israeli Patent Application No. 224614 dated Nov. 29, 2016, 2 pages, and 3 page Agent summary.
Office Action—Notice of Reasons for Rejection- ssued by the Japanese Patent Office for Application No. 2016-49456, dated Dec. 15, 2016, 13 pages (includes translation).
Office action issued by the United States Patent and Trademark Office for U.S. Appl. No. 14/839,503, dated Nov. 21, 2016, 7 pages.
Office Action issued by the Brazilian Patent Office for Application No. BR 11 2013 004579 5 dated Nov. 30, 2016, 11 pages and 2 page Agent summary.
Office Action—Examination Report—issued by the New Zealand Patent Office for Application No. 726487, dated Dec. 16, 2016, 4 pages.
Office Action—Acceptance-issued by the Australian Patent Office for Application No. 2015201367, dated Dec. 6, 2016, 3 pages.
Office Action issued by the Japanese Patent Office for Application No. 2014-560065, dated Jan. 26, 2017, 5 pages and 8 pages English translation.
Notice of Acceptance issued by the New Zealand Patent Office for Application No. 629888, dated Feb. 2, 2017, 1 page.
Office Action issued by the Philippines Patent Office for Application No. 1-2013-500347, dated Dec. 15, 2016, 2 pages.
Colby, D.W., et al., "Development of a Human Light Chain Variable Domain (VL) Intracellular Antibody Specific for the Amino Terminus of Huntingtin via Yeast Surface Display," J. Mol. Biol. 342:901-912 (2004).
Masat, L., et al., "A Simpler Sort of Antibody (Light Chain Monomer/Nevus Antigen/Melanoma)," Proc. Natl. Acad. Sci. Usa 91:893-896 (1994).
Second Office Action issued by the Eurasian patent Office for Application No. 201491575/ 28, received Feb. 24, 2017, 1 page non-English, 4 pages Engl translation and claims.
Communication pursuant to Article 94(3) EPC issued by the European Patent Office for Application No. 12708473.9, dated Feb. 2, 2017, 3 pages.
Office Action issued by the China State Intellectual Property Office for Application No. 201410816632.5 , dated Feb. 24, 2017, 8 pages (English translation).
Office Action issued by the Israeli Patent Office for Application No. 234263, dated Apr. 9, 2017, 17 pages including partial English translation (3 pages), Agent's Summary (5 pages), and 9 pages English claims.

\* cited by examiner

FIGURE 1

Anti-MMP9 humanized heavy chains

```
AB0041  QVQLKESGPG LVAPSQSLSI TCTVSGFSLL SYGVHWVRQP PGKGLEWLGV
VH1     QVQLQESGPG LVKPSETLSL TCTVSGFSLL SYGVHWVRQP PGKGLEWLGV
VH2     QVQLQESGPG LVKPSETLSL TCTVSGFSLL SYGVHWVRQP PGKGLEWLGV
VH3     QVQLQESGPG LVKPSETLSL TCTVSGFSLL SYGVHWVRQP PGKGLEWLGV
VH4     QVQLQESGPG LVKPSETLSL TCTVSGFSLL SYGVHWVRQP PGKGLEWLGV

AB0041  IWTGGTTNYN SALMSRLSIS KDDSKSQVFL KMNSLQIDDT AIYYCARYYY
VH1     IWTGGTTNYN SALMSRLTIS KDDSKSTVYL KMNSLKTEDT AIYYCARYYY
VH2     IWTGGTTNYN SALMSRLTIS KDDSKNTVYL KMNSLKTEDT AIYYCARYYY
VH3     IWTGGTTNYN SALMSRFTIS KDDSKNTVYL KMNSLKTEDT AIYYCARYYY
VH4     IWTGGTTNYN SALMSRFTIS KDDSKNTLYL KMNSLKTEDT AIYYCARYYY

AB0041  GMDYWGQGTS VTVSS  (SEQ ID NO:3)
VH1     GMDYWGQGTS VTVSS  (SEQ ID NO:5)
VH2     GMDYWGQGTL VTVSS  (SEQ ID NO:6)
VH3     GMDYWGQGTL VTVSS  (SEQ ID NO:7)
VH4     GMDYWGQGTL VTVSS  (SEQ ID NO:8)
```

FIGURE 2

Anti-MMP9 humanized light chains

```
AB0041  DIVMTQSHKF MSTSVGDRVS ITCKASQDVR NTVAWYQQKT GQSPKLLIYS
Vk1     DIVMTQSPSF LSASVGDRVT ITCKASQDVR NTVAWYQQKT GKAPKLLIYS
Vk2     DIVMTQSPSS LSASVGDRVT ITCKASQDVR NTVAWYQQKP GKAPKLLIYS
Vk3     DIQMTQSPSS LSASVGDRVT ITCKASQDVR NTVAWYQQKP GKAPKLLIYS
Vk4     DIQMTQSPSS LSASVGDRVT ITCKASQDVR NTVAWYQQKP GKAPKLLIYS

AB0041  SSYRNTGVPD RFTGSGSGTD FTFTISSVQA EDLAVYFCQQ HYITPYTFGG
Vk1     SSYRNTGVPD RFTGSGSGTD FTLTISSLQA EDVAVYFCQQ HYITPYTFGG
Vk2     SSYRNTGVPD RFTGSGSGTD FTLTISSLQA EDVAVYFCQQ HYITPYTFGG
Vk3     SSYRNTGVPD RFSGSGSGTD FTLTISSLQA EDVAVYFCQQ HYITPYTFGG
Vk4     SSYRNTGVPD RFSGSGSGTD FTLTISSLQA EDVAVYYCQQ HYITPYTFGG

AB0041  GTKLEIK  (SEQ ID NO:4)
Vk1     GTKVEIK  (SEQ ID NO:9)
Vk2     GTKVEIK  (SEQ ID NO:10)
Vk3     GTKVEIK  (SEQ ID NO:11)
Vk4     GTKVEIK  (SEQ ID NO:12)
```

Figure 4: Comparison between AB0041, M4, and M12 heavy and light chains

Light chains

Signal Peptide | CDRL1 | CDRL2
M4      MESQIQVFVFVFLWLSGVDGDIVMTQSHKFMSTSVGDRVSITCKASQDVRNTVAWQQKTGQSPKLLIYSASYRNTGVPD
AB0041  MESQIQVFVFVFLWLSGVDGDIVMTQSHKFMSTSVGDRVSITCKASQDVRNTVAWQQKTGQSPKLLIYSSSYRNTGVPD
M12         QVFVIMLLWLSGVDGDIVMTQSHKFMSTSVGDRVSYTCKASQNGTNNVAWQQKPGQSPKALIYSASYRFSGVPD CDRL3            kappa constant
M4      RFTGSISGTDFTFTISSVQAEDLALYYCQQHYSTPYTFGGGTKLEYKRADAAPTVSIFPPSTRDPRAN
AB0041  RFTGSGSGTDFTFTISSVQAEDLAVYFCQQHYITPYTFGGGTKLEIKRADAAPTVSIFPPSTRDPRAN
M12     RFTGSGSGTDFTLTISNVQSEDLAEYFCQQYNSYPYTFGQGTKLEIKRADAAPTVSIFPPSTRDPRAN Light chains Signal Peptide                           CDRL1
M4      MAVLVLFLCLVAFPSCVLSQVQLKESGPGLVAPSQSLSITCTVSGFSLLSYGVHWVRQPPGKGLEWLGVIWTGGSTNYNS
AB0041  MAVLVLFLCLVAFPSCVLSQVQLKESGPGLVAPSQSLSITCTVSGFSLLSYGVHWVRQPPGKGLEWLGVIWTGGSTNYNS CDRL3                           CDRL2
M4      ALMSRLSISKDDSKSQVFLKMNSLQTDDTAMYYCARYYYAMDYWGQGTSVTVSSAKTTPPSVYPLAPGCGDTTGSSVTLG
AB0041  ALMSRLSISKDDSKSQVFLKMNSLQTDDTAIYYCARYYGMDYWGQGTSVTVSSAKTTPPSVYPLAPGCGDTTGSSVTLG IgG2b constant
M4      CLVKGYFPESVTVTWNSGSL
AB0041  CLVKGYFPESVTVTWNSGSL

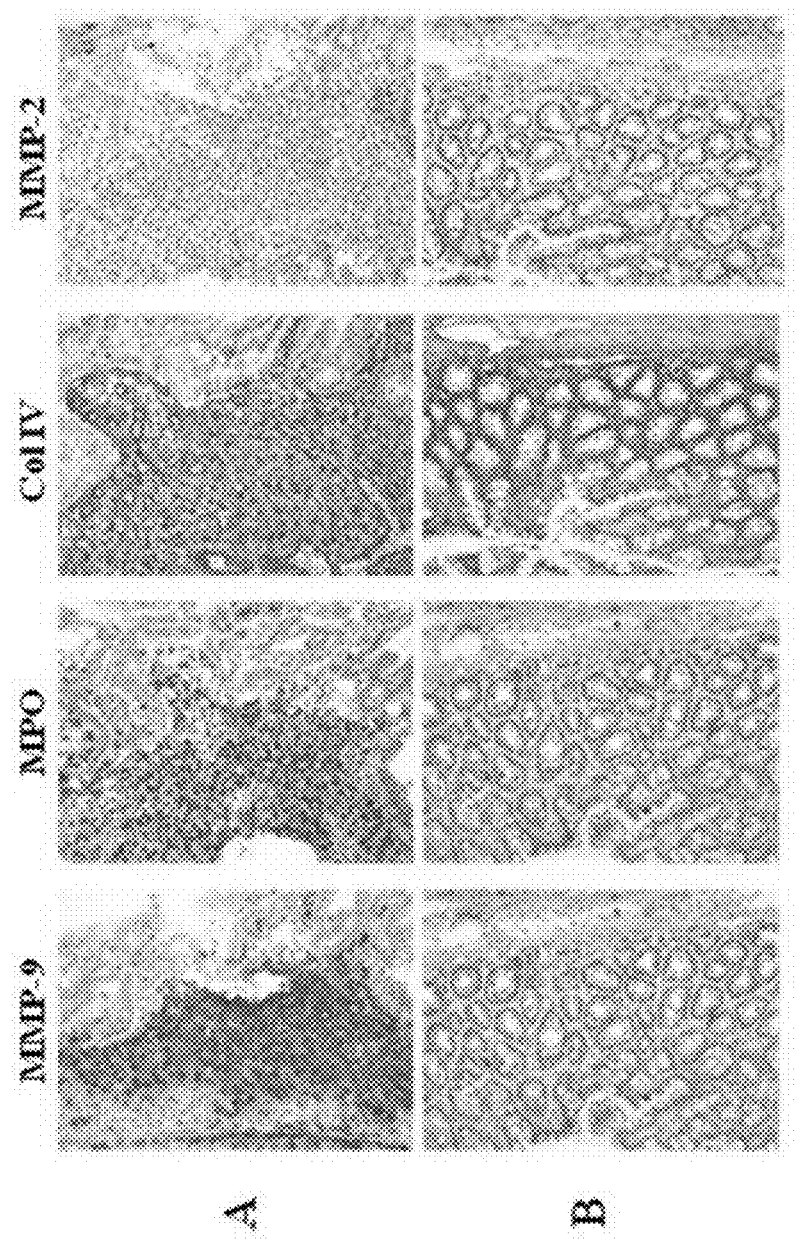
Figure 5: Association of MMP9 induction with inflammation and destruction of tissue architecture in DSS colitis

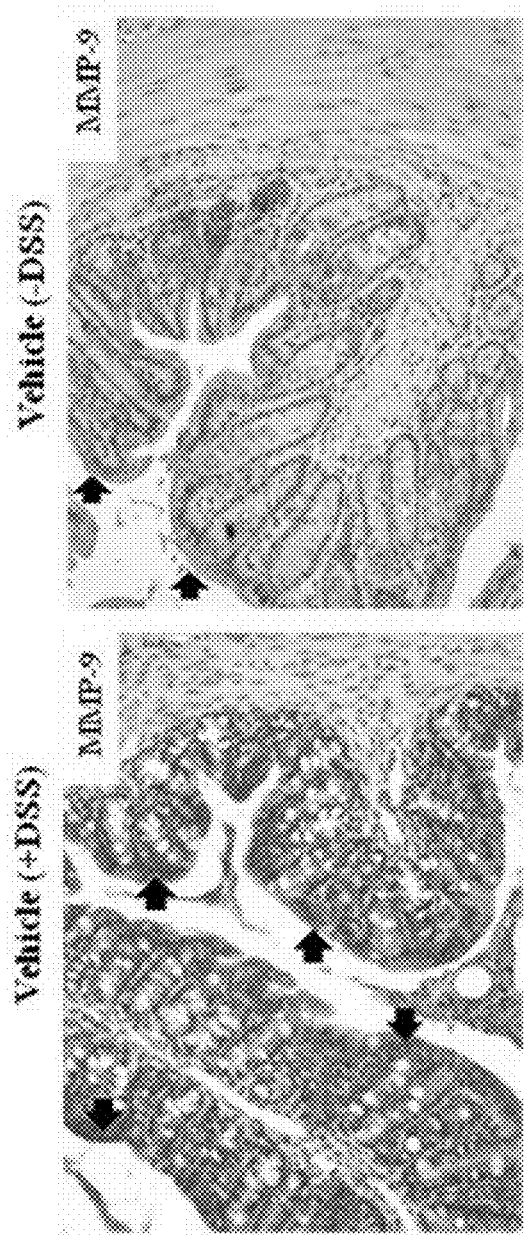
Figure 6: MMP9 induction in colonic epithelial cells in DSS colitis

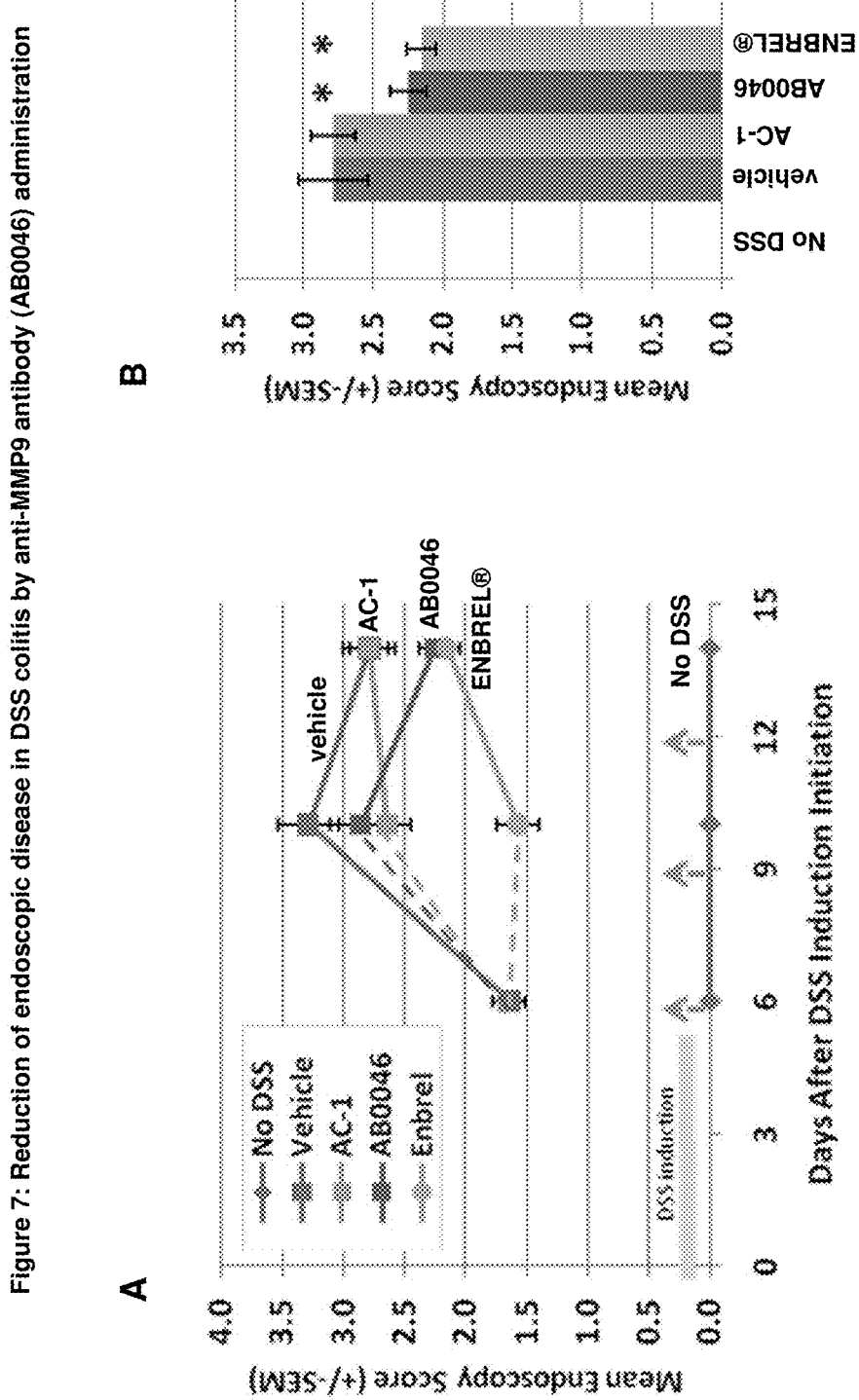
Figure 7: Reduction of endoscopic disease in DSS colitis by anti-MMP9 antibody (AB0046) administration

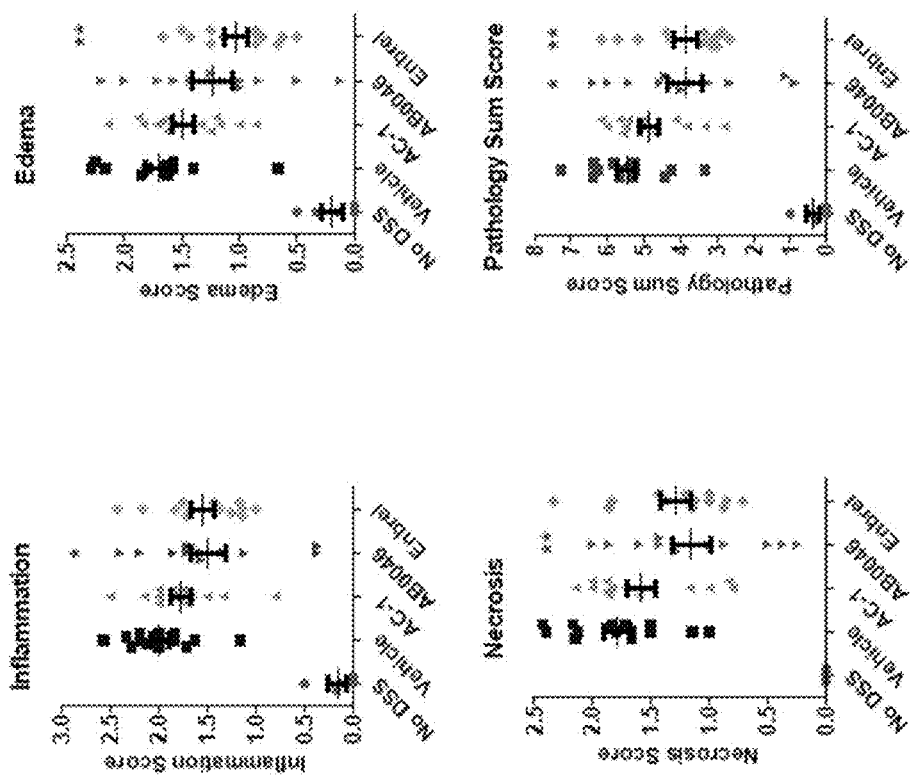
Figure 8: Reduction of histological disease in DSS colitis by anti-MMP9 antibody (AB0046) administration

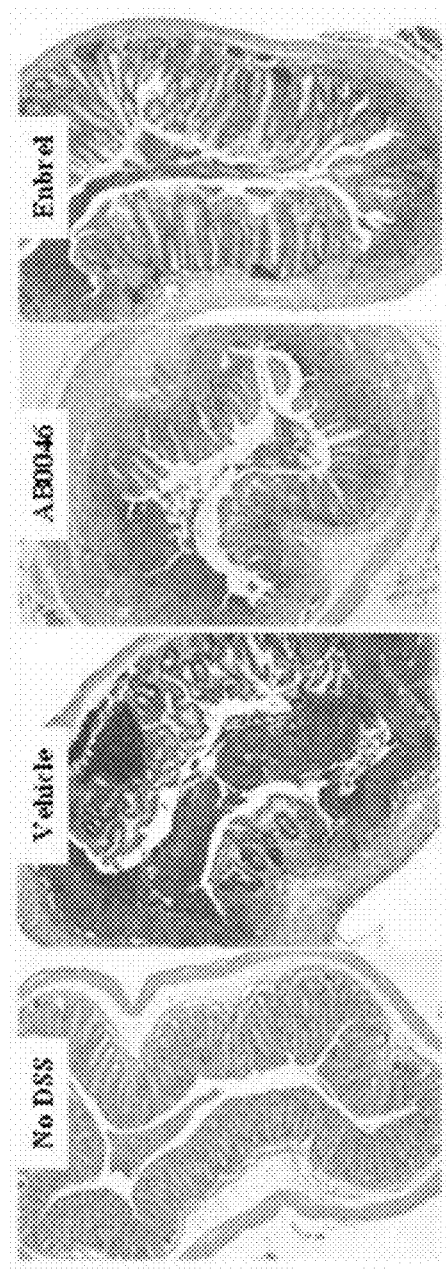
Figure 9: Reduction of MMP9 expression resulting from anti-MMP9 antibody (AB0046) treatment in DSS colitis model, correlating with reduced disease Figure 10: Protection against body weight loss and the incidence of diarrhea in DSS colitis by anti-MMP9 antibody (AB0046)
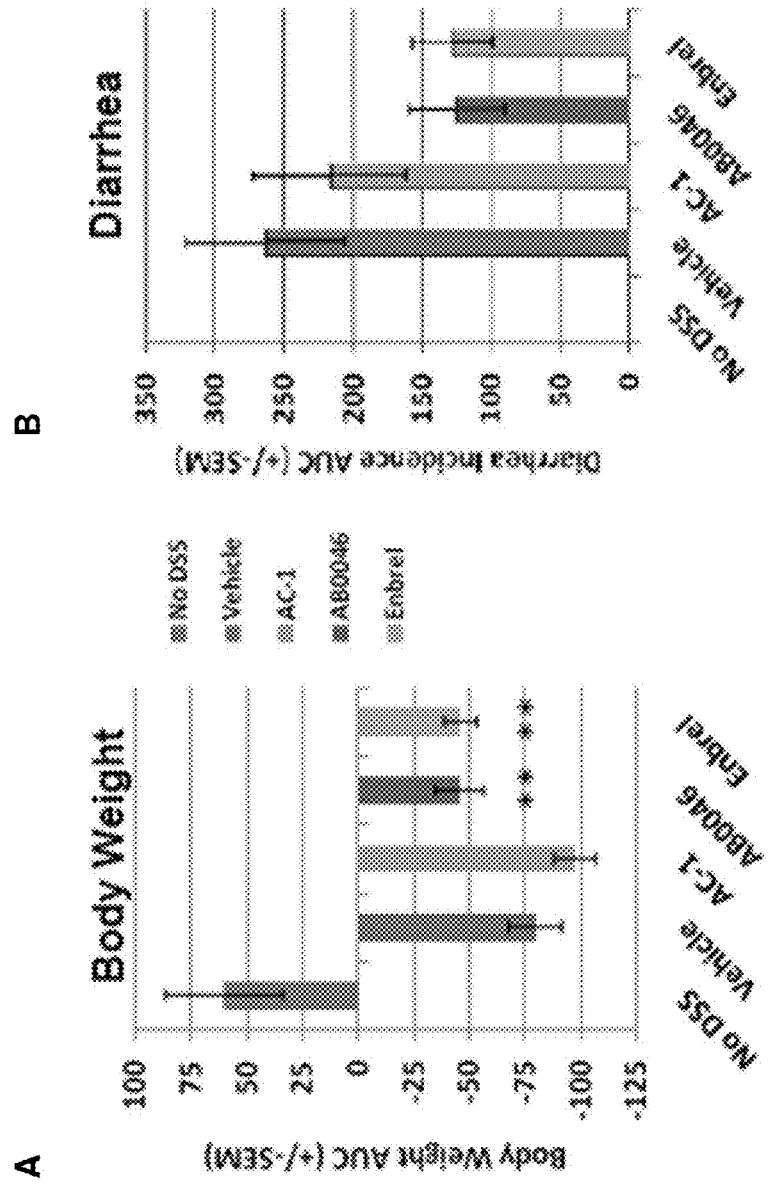

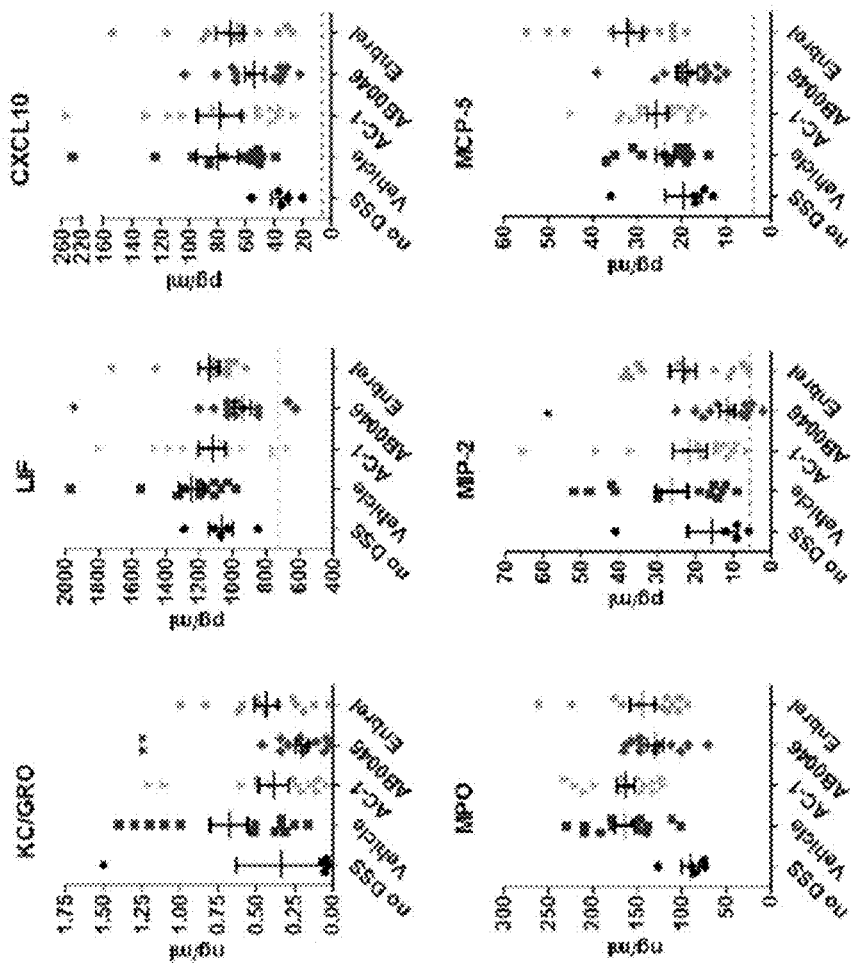
Figure 11A: Reduction in systemic markers of inflammation in DSS colitis by treatment with anti-MMP9 antibody AB0046

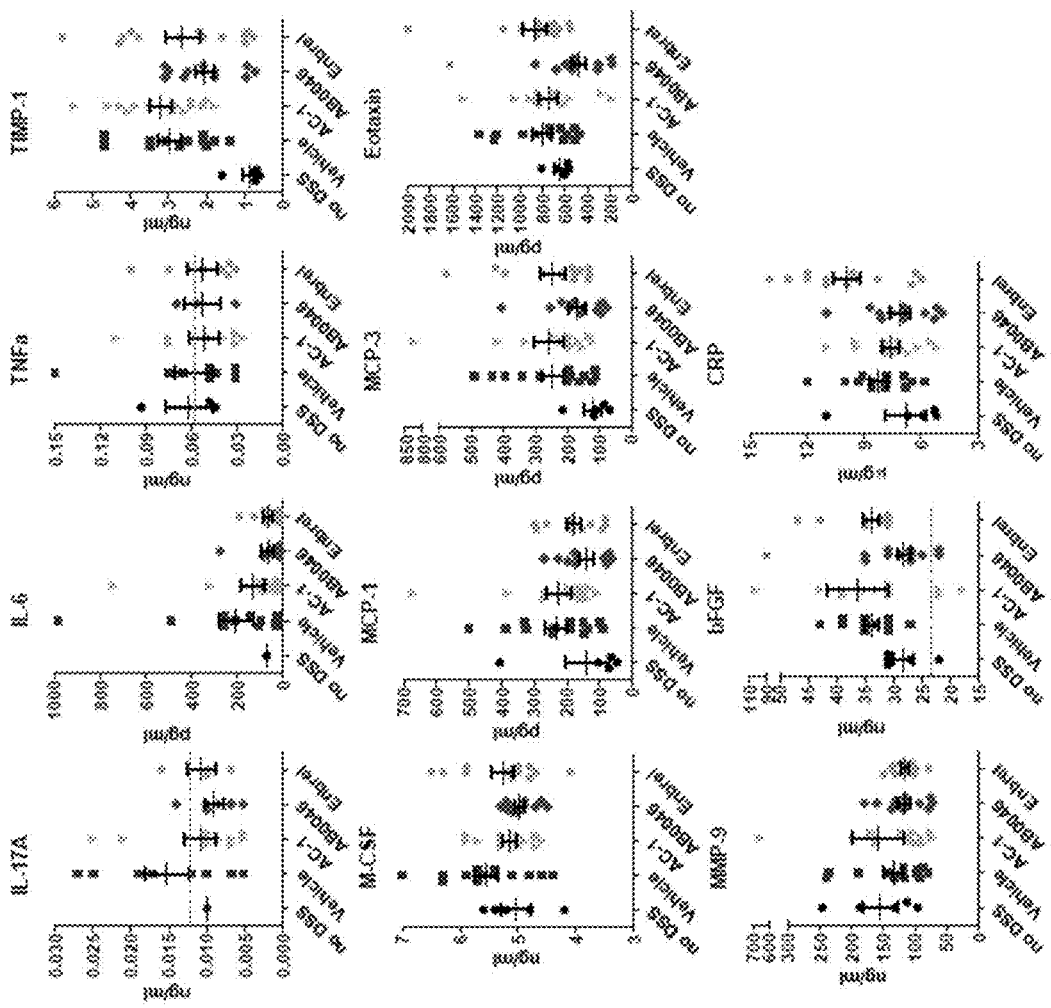
Figure 11B: Additional serum marker data for murine DSS colitis treatment study

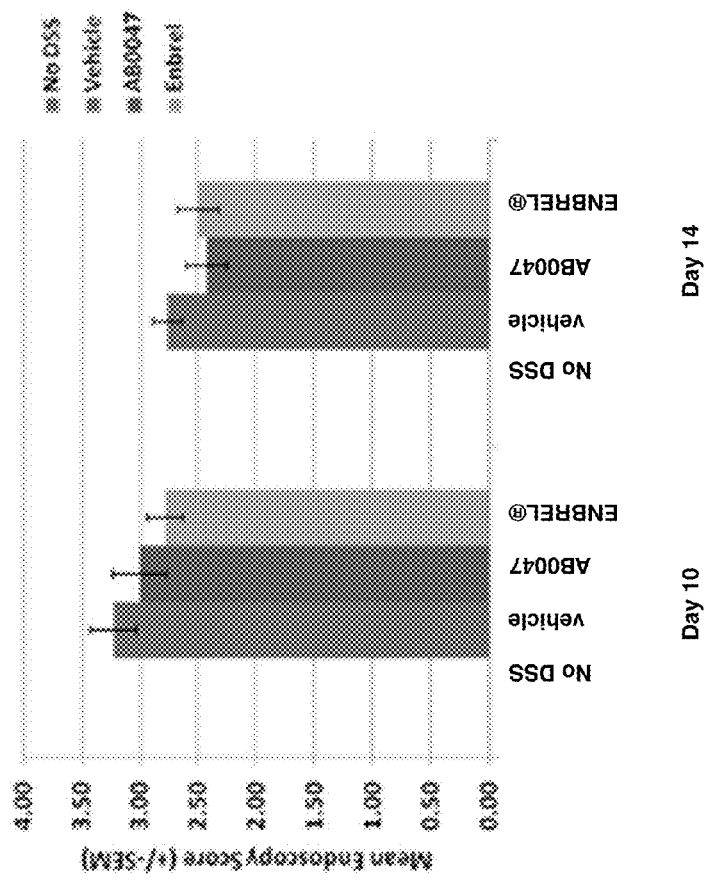
Figure 12A: Reduction of endoscopic disease by anti-MMP9 antibody (AB0047) treatment in DSS colitis model

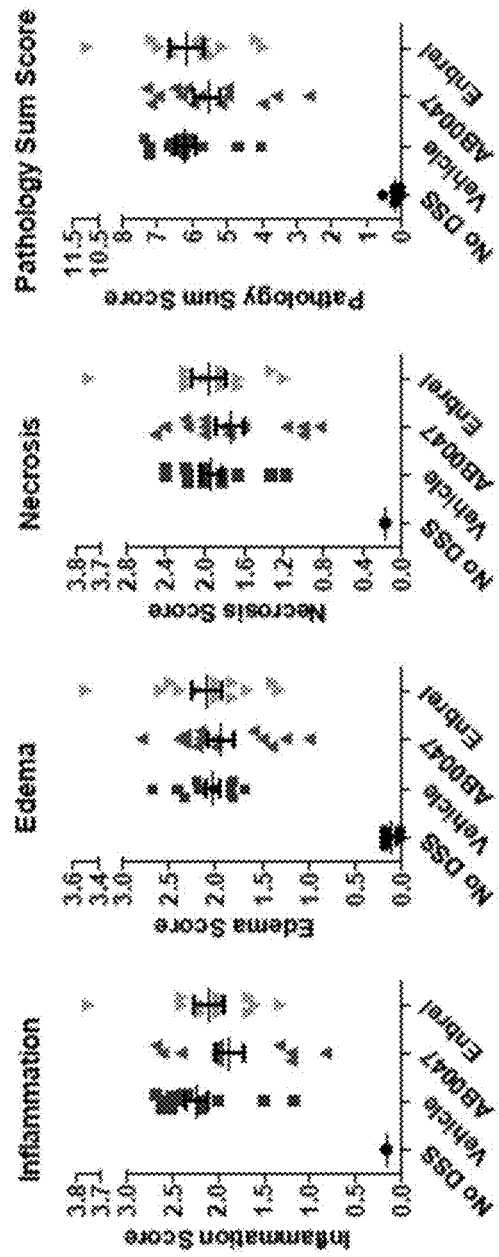
Figure 12B: Reduction in histological disease by anti-MMP9 antibody (AB0047) treatment in DSS colitis model

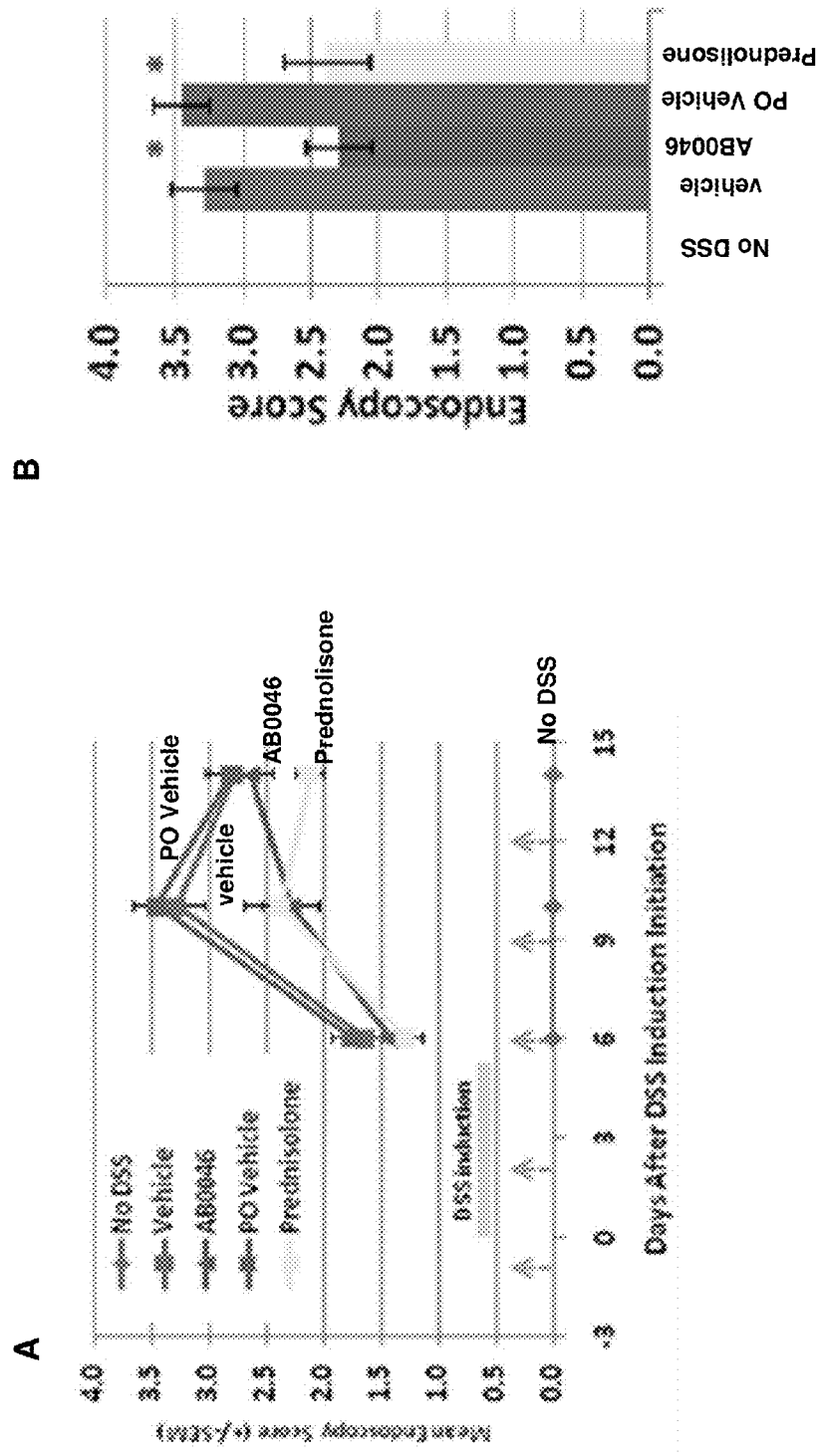
Figure 13: Reduction in endoscopic disease by anti-MMP9 antibody (AB0046) prophylactic treatment in DSS colitis model

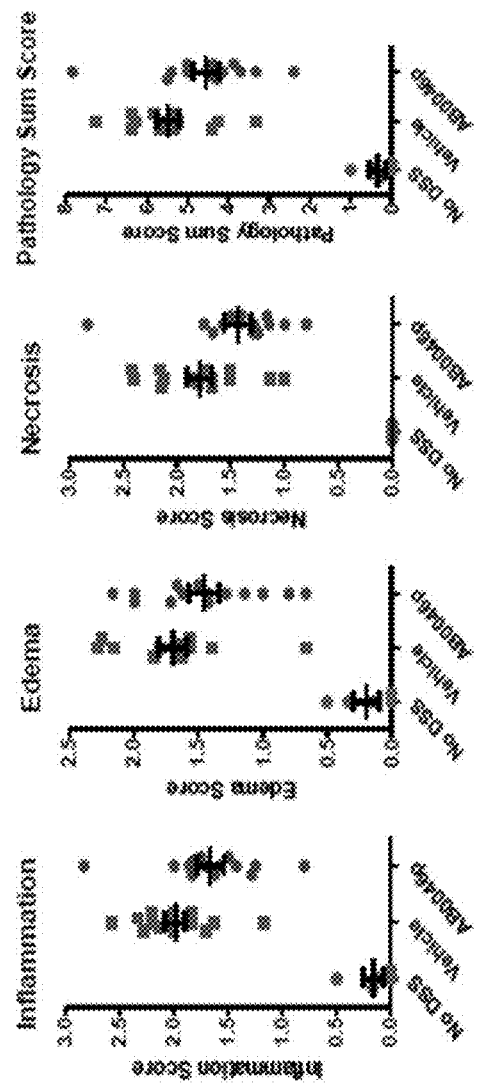
Figure 14: Reduction in histological disease by anti-MMP9 antibody (AB0046) prophylactic treatment in DSS colitis model

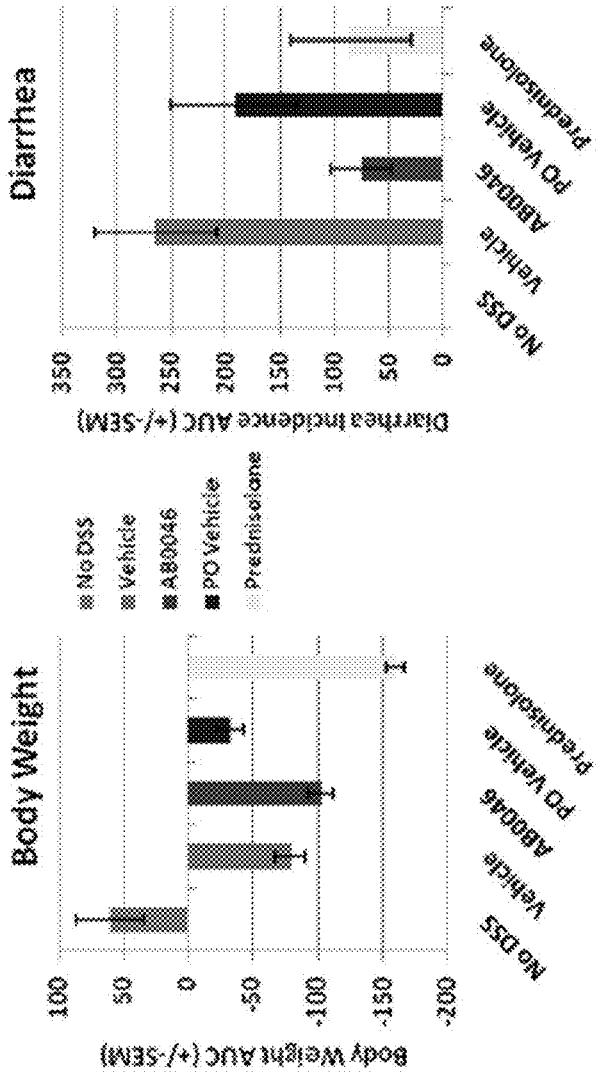
Figure 15: Protection against incidence of diarrhea in DSS colitis by prophylactic administration of anti-MMP9 antibody (AB0046)

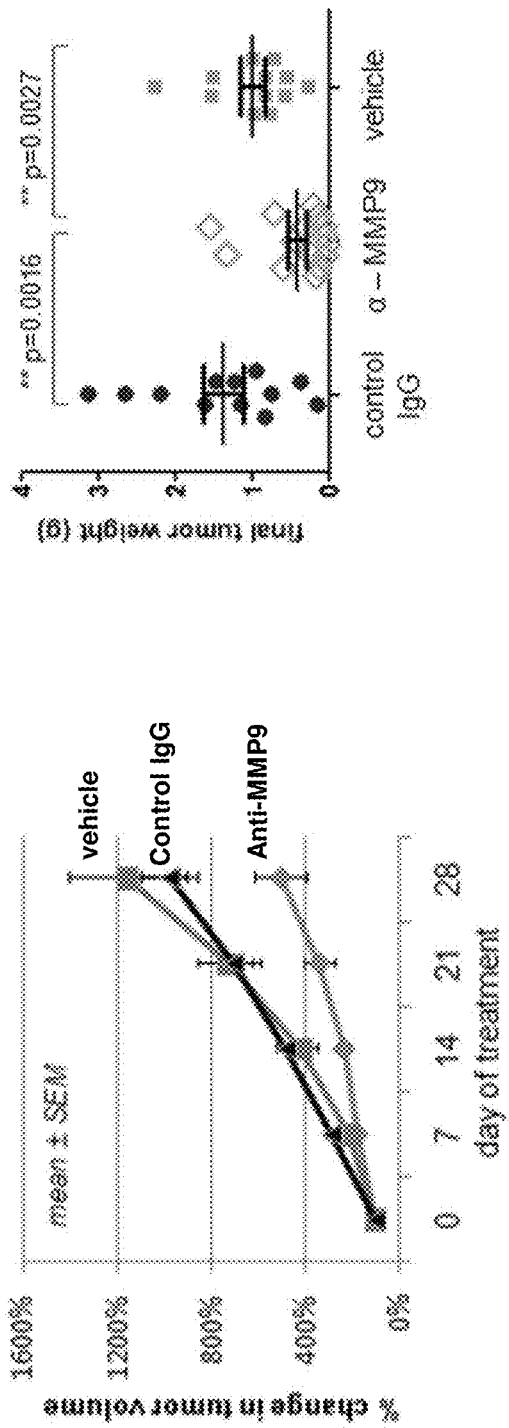
Figure 16: Decrease in primary tumor growth in established colorectal cancer tumorigenesis model with anti-MMP9 antibody treatment

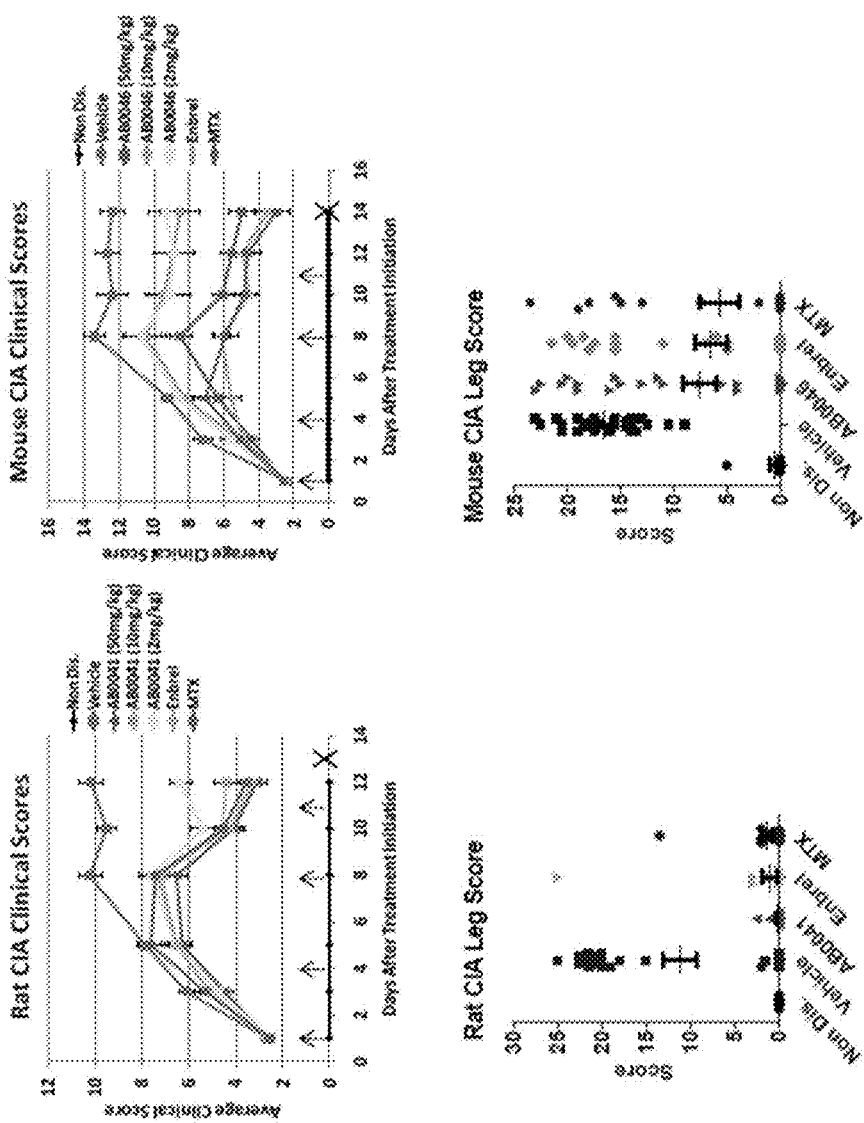
Figure 17A: Efficacy of murine surrogate anti-MMP9 (AB0046) and anti-human MMP9 (AB0041) antibodies in mouse and rat CIA models of rheumatoid arthritis

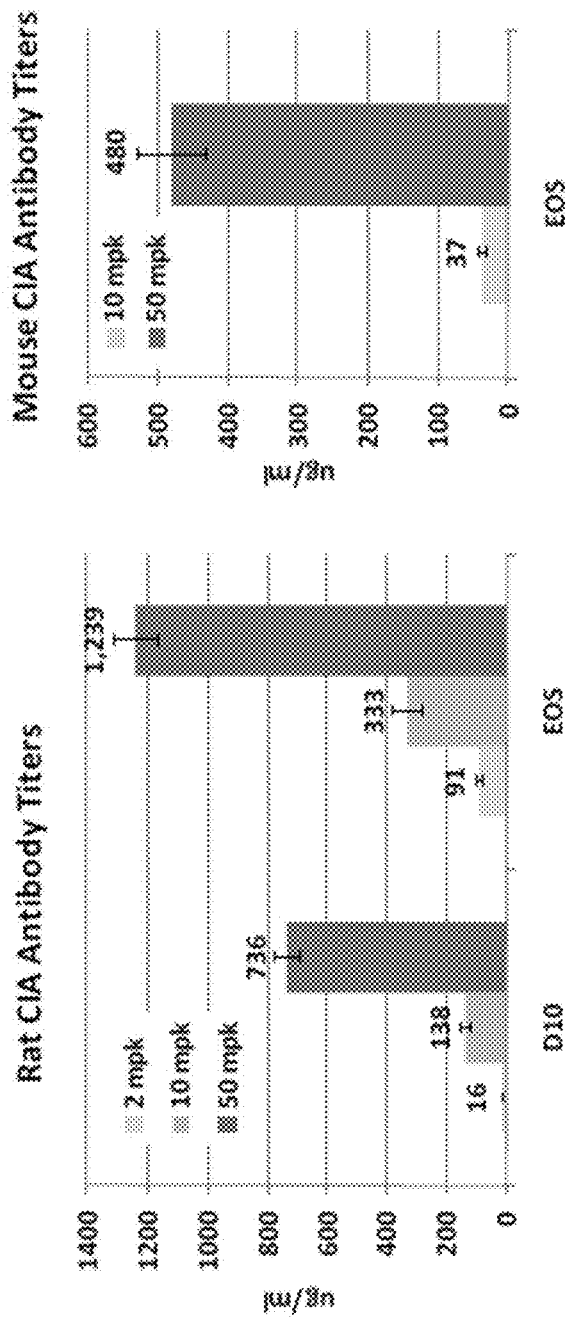
Figure 17B: Titers of murine surrogate anti-MMP9 (AB0046) and anti-human MMP9 (AB0041) antibodies in mouse and rat CIA models of rheumatoid arthritis

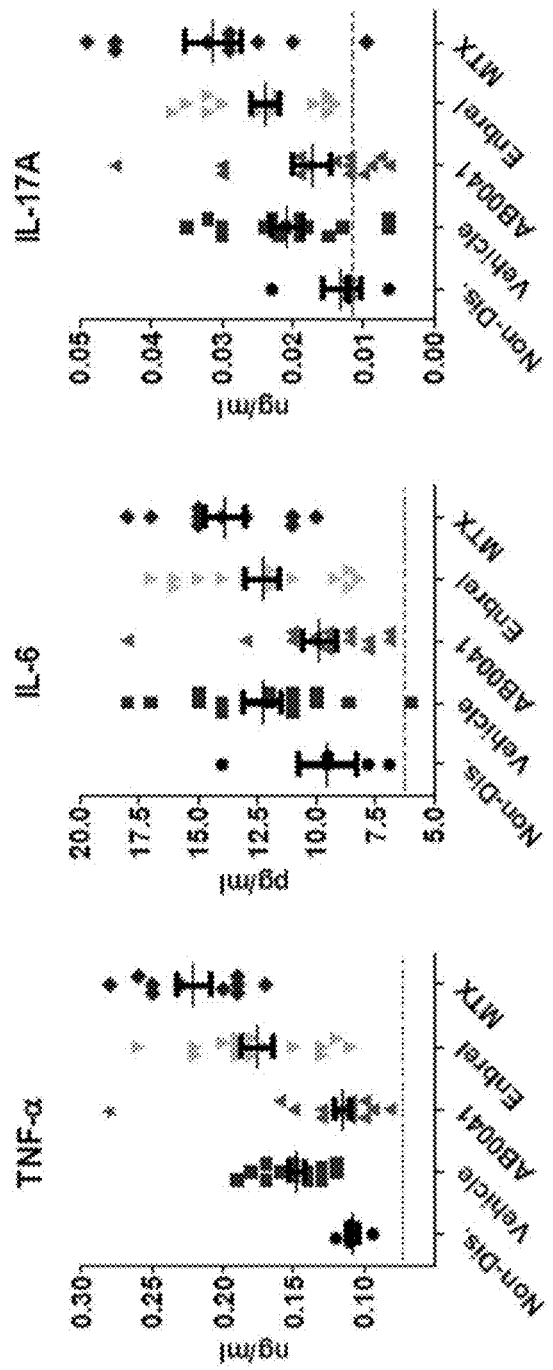
Figure 18A: End-of-study serum levels of inflammatory cytokines in CIA model of rheumatoid arthritis in the rat

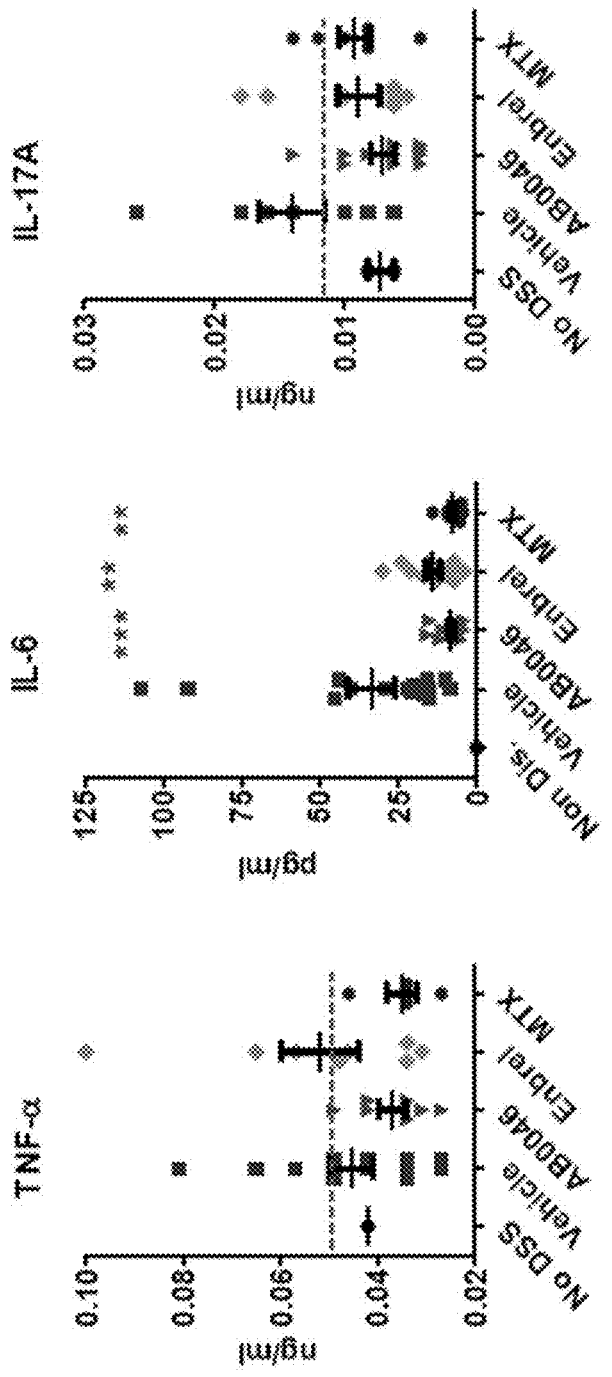
Figure 18B: End-of-study serum levels of inflammatory cytokines in CIA model of rheumatoid arthritis in the mouse

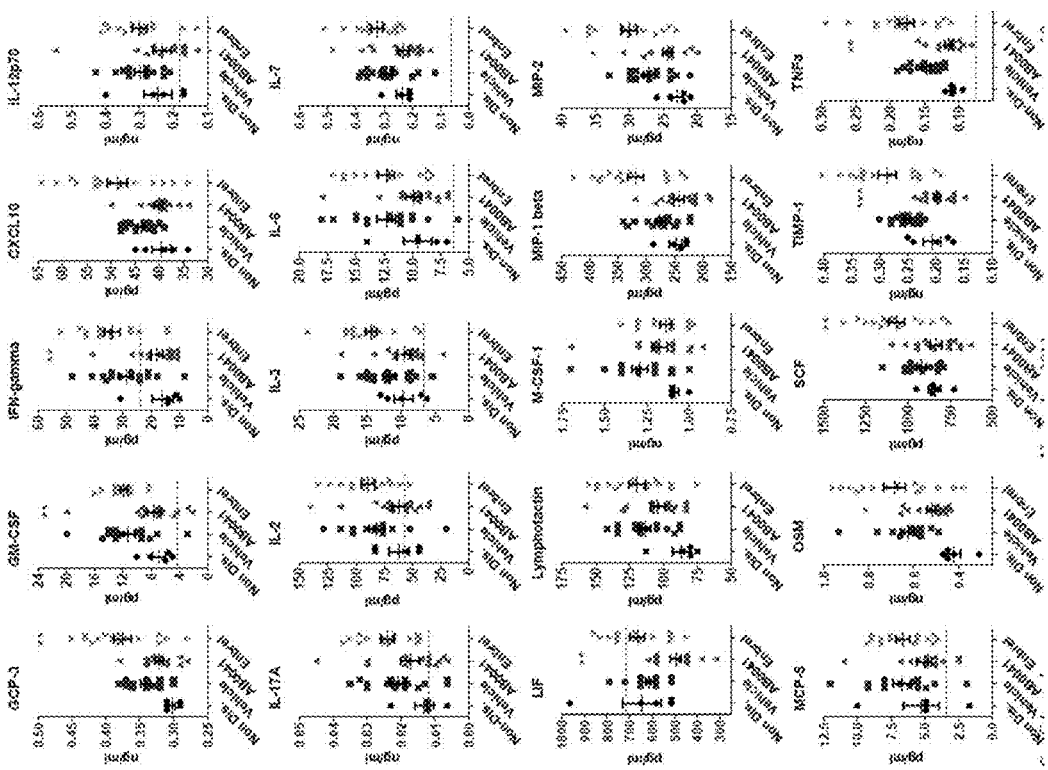
Figure 19A: Additional serum marker data for rat CIA treatment study (AB0041)

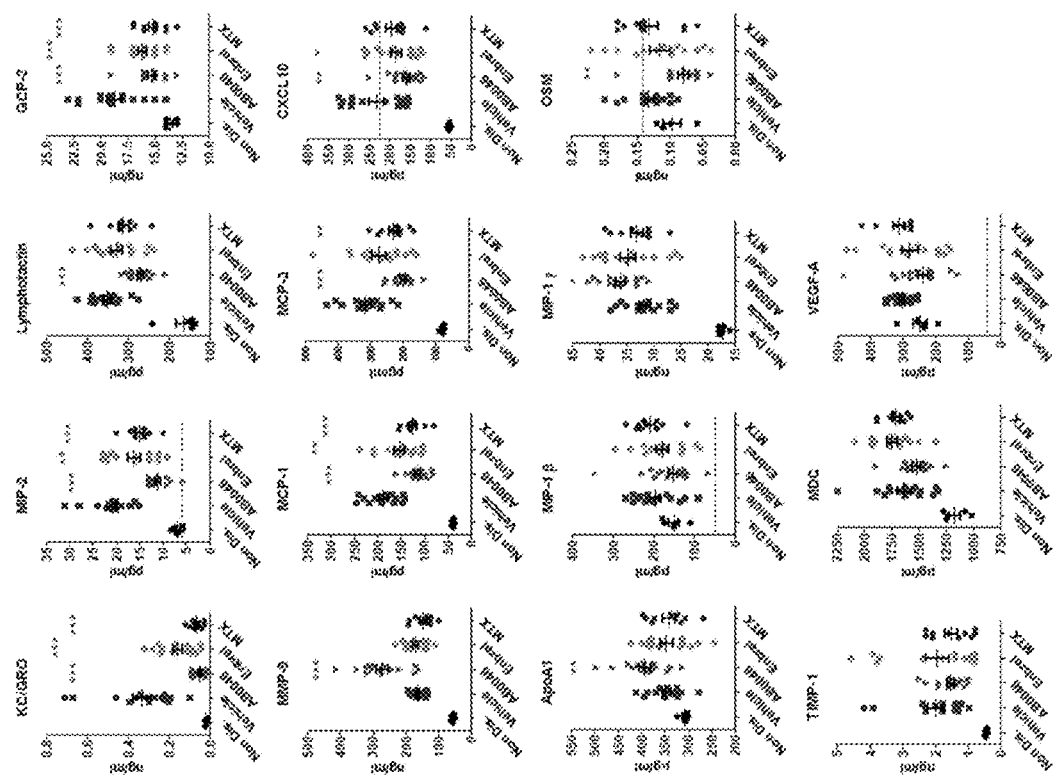
Figure 19B: Additional serum marker data for mouse CIA treatment study (AB0046)

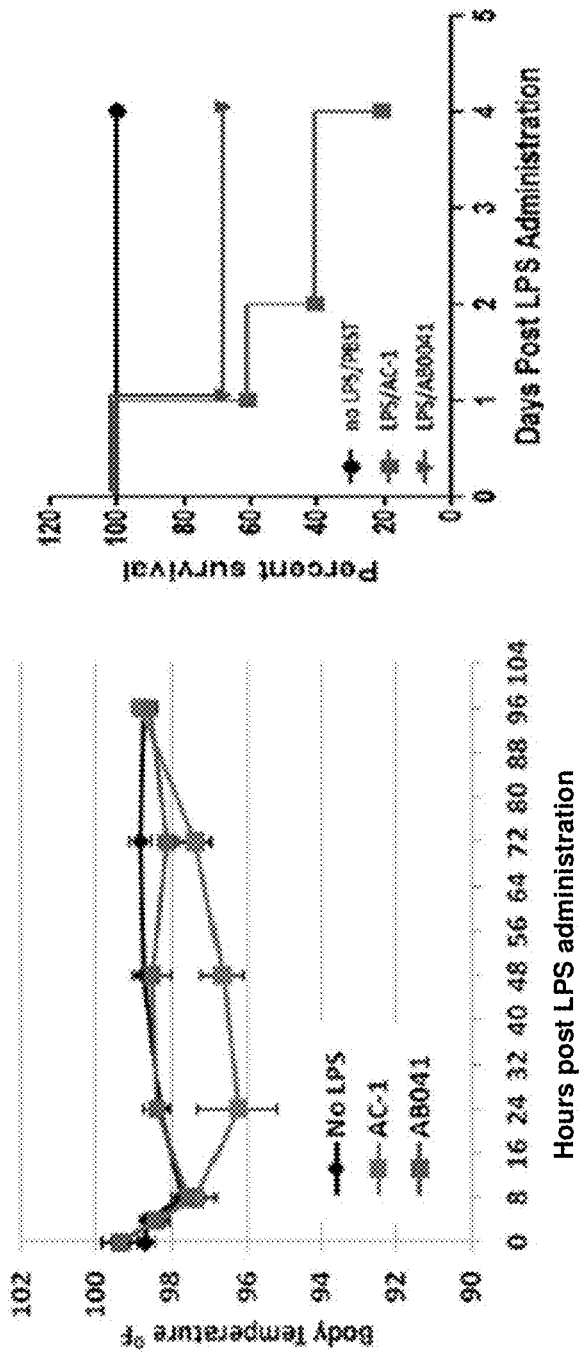

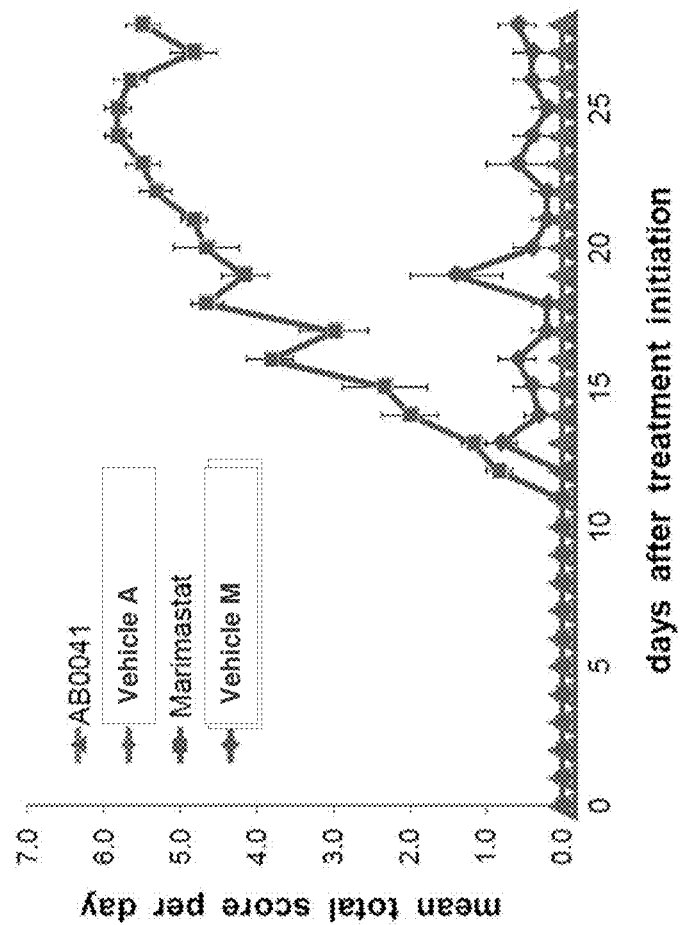
Figure 21: MSS Scores for AB0041-treated, Marimastat-treated, and control animals

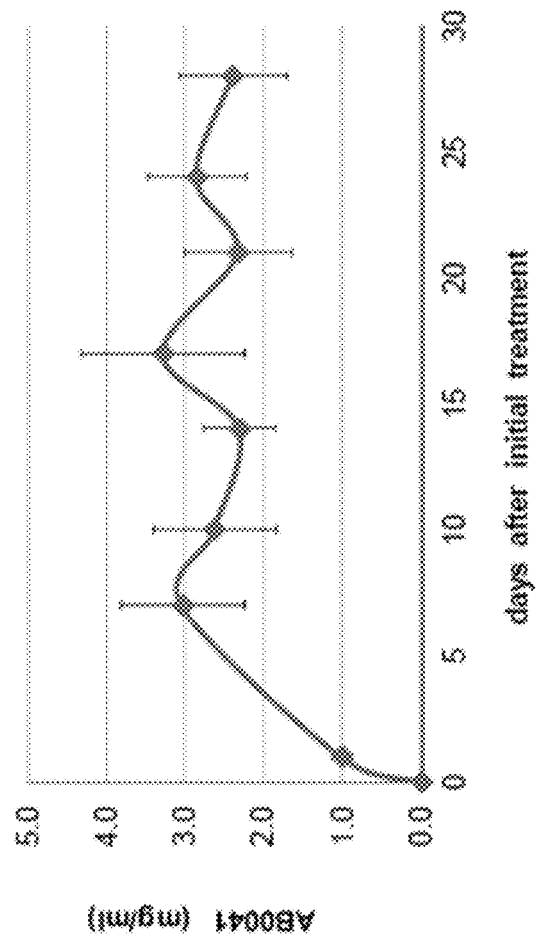
Figure 22: Serum Titer Analysis of AB0041 Levels

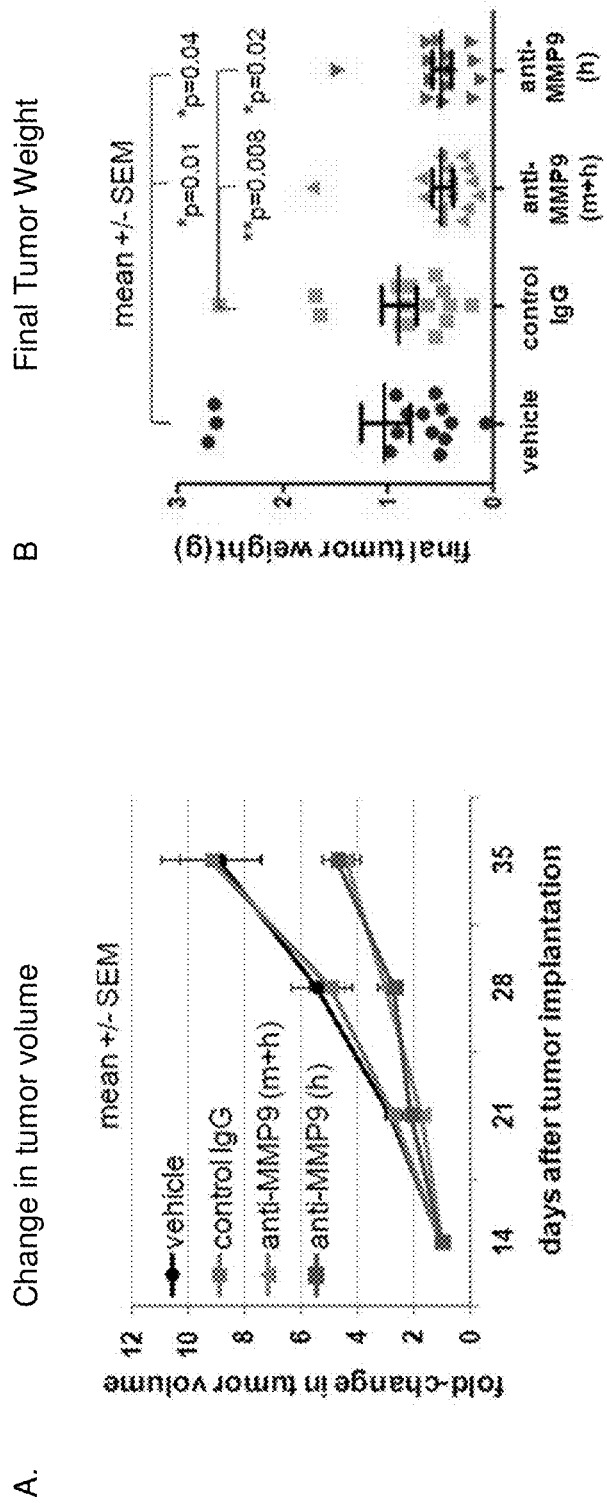
Figure 23: Tumor Growth and Metastases in Mouse Colorectal Cancer Model after anti-MMP9 Treatment

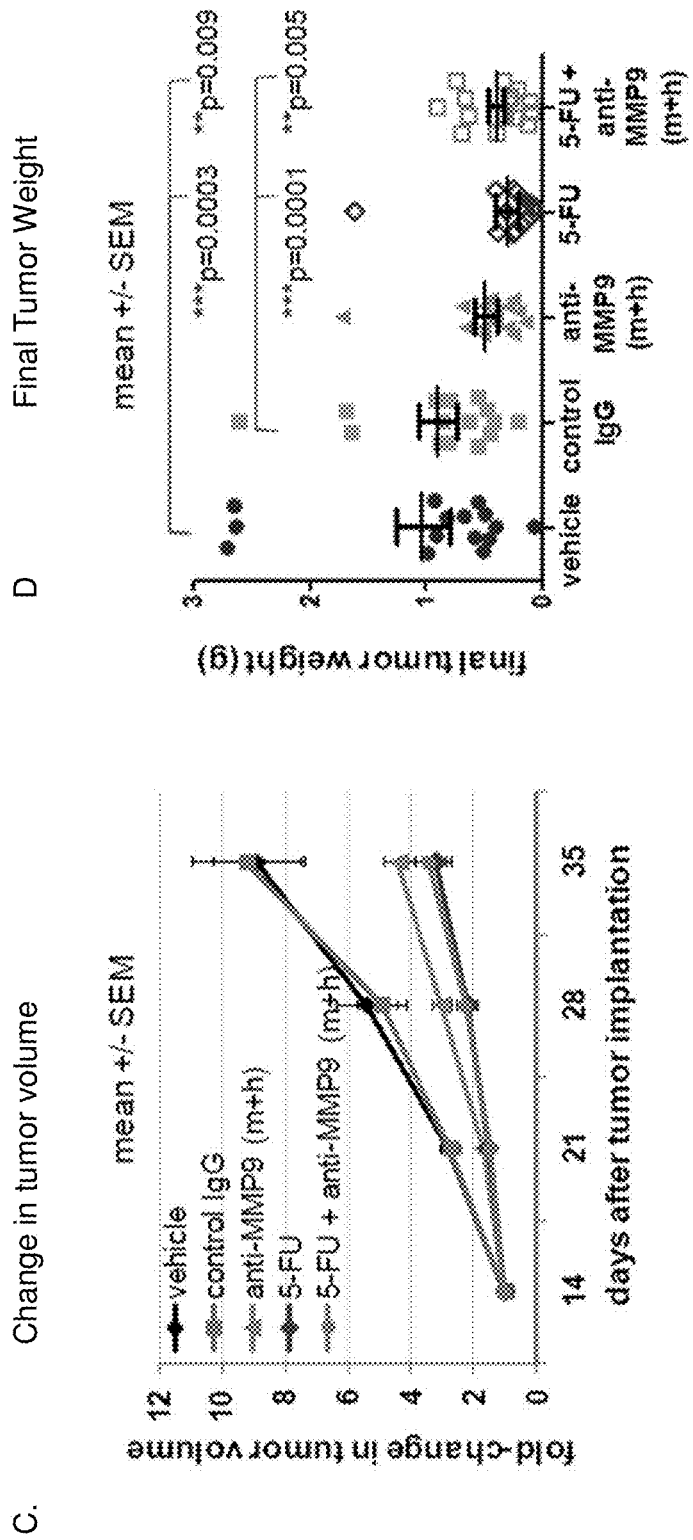
Figure 23, cont.: Tumor Growth and Metastases in Mouse Colorectal Cancer Model after anti-MMP9 Treatment

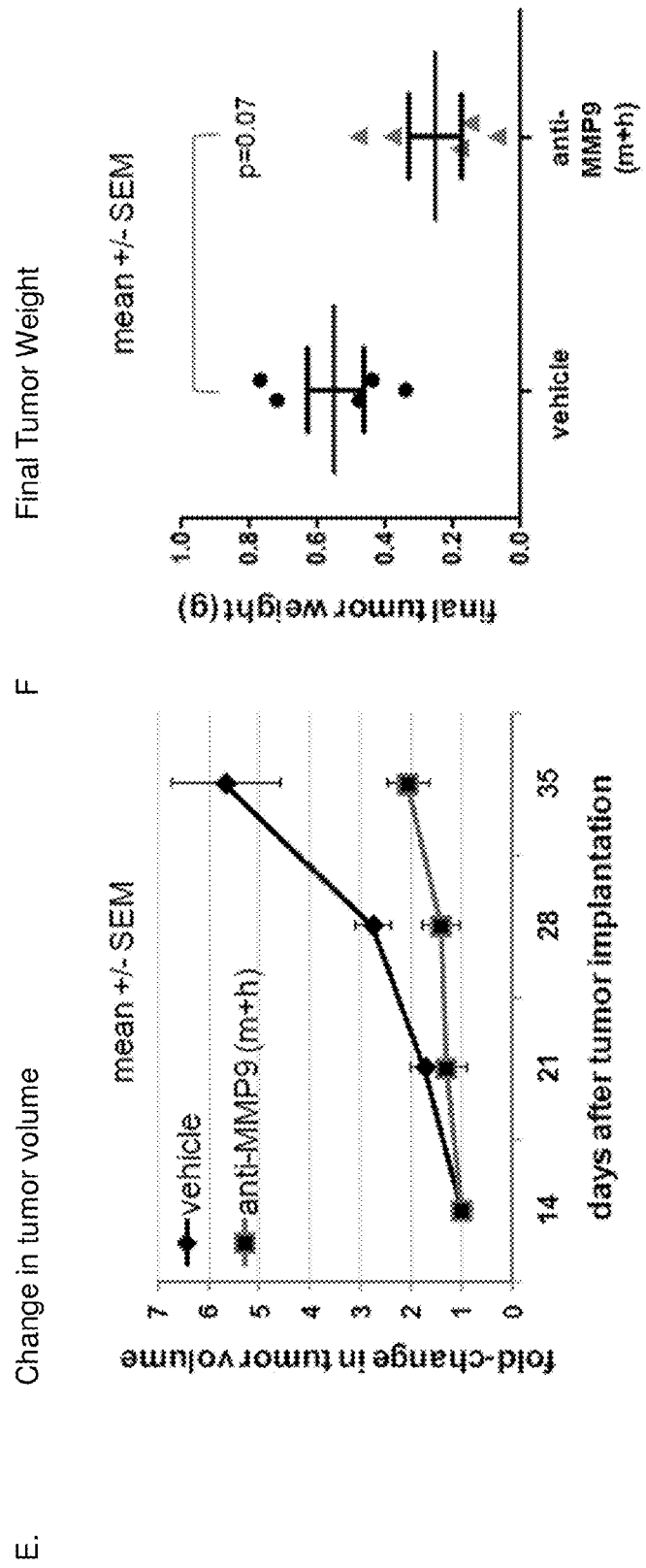
Figure 23, cont.: Tumor Growth and Metastases in Mouse Colorectal Cancer Model after anti-MMP9 Treatment

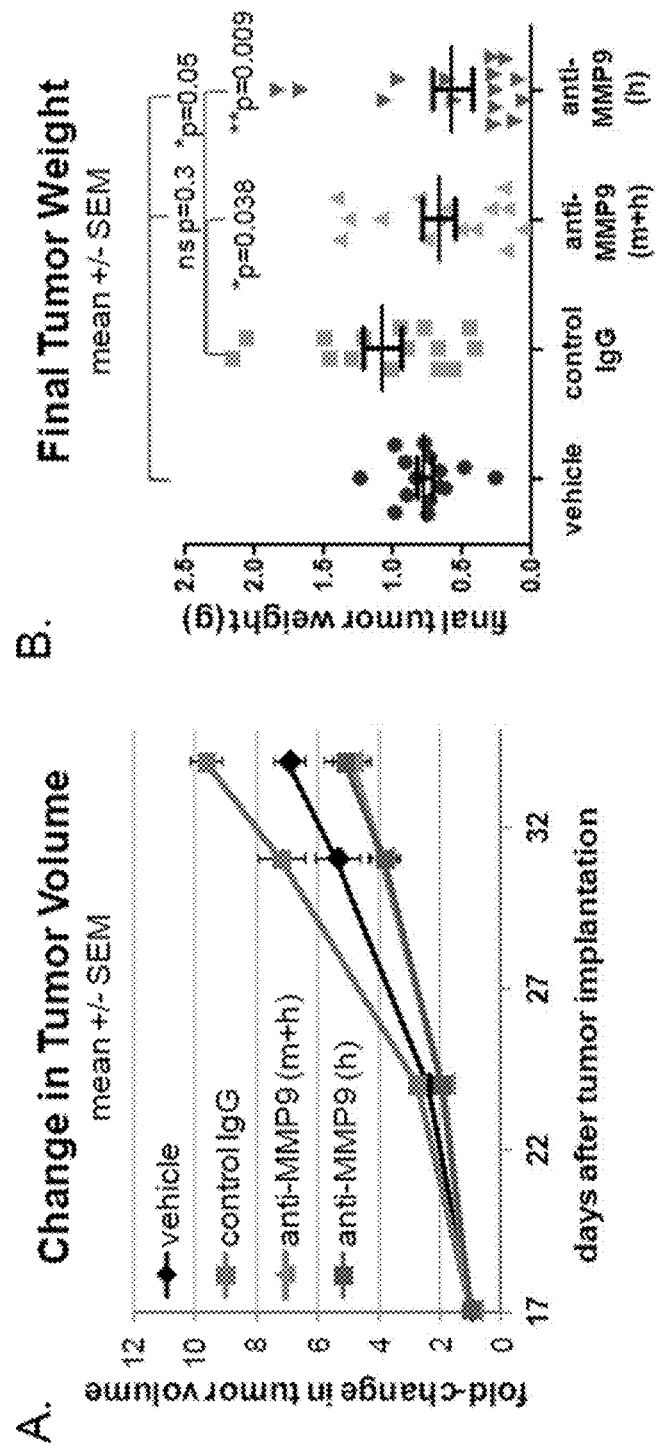
Figure 24: Tumor Growth and Metastases in Mouse Colorectal Cancer Model after anti-MMP9 Treatment

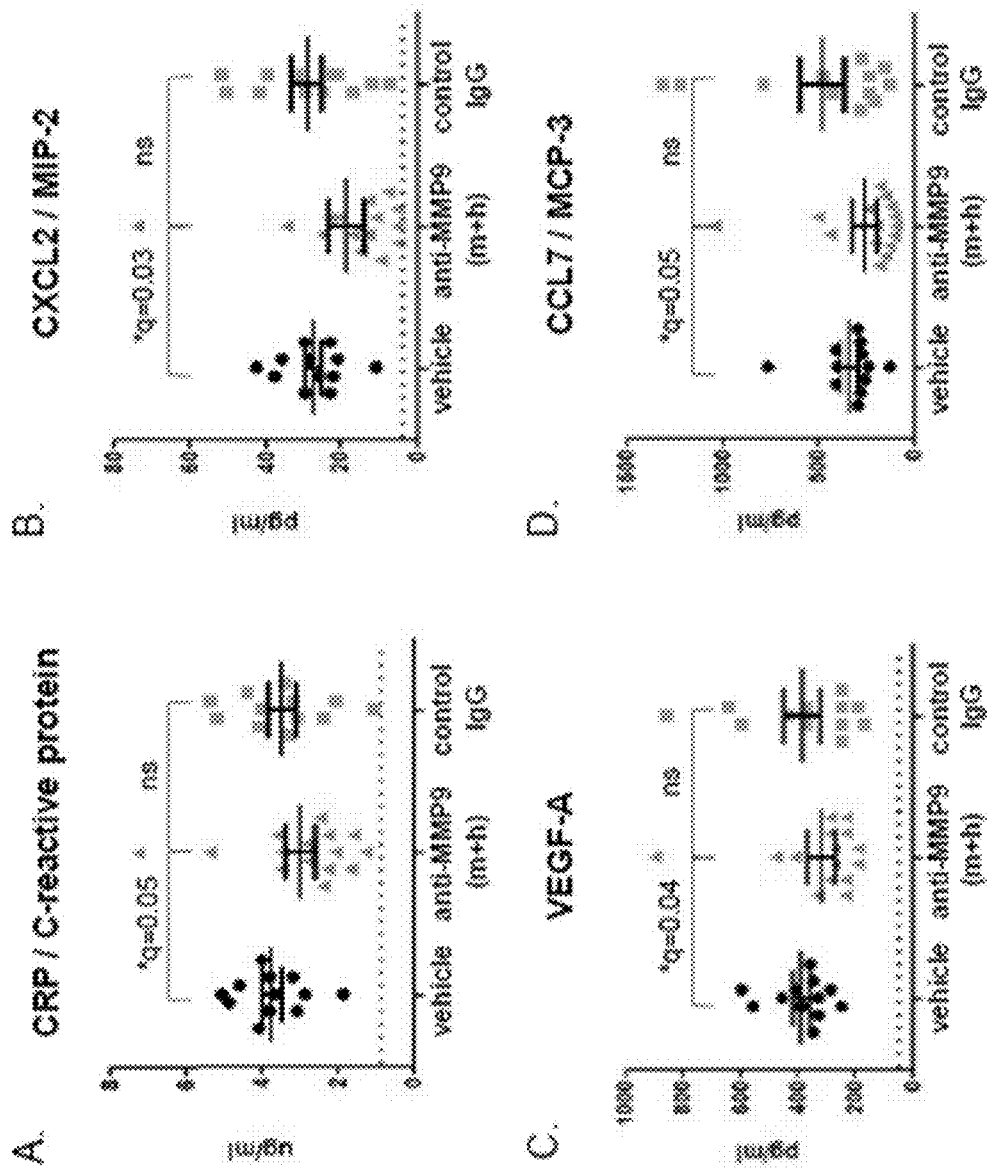
Figure 25: Levels of serum proteins following control and anti-MMP-9 treatment

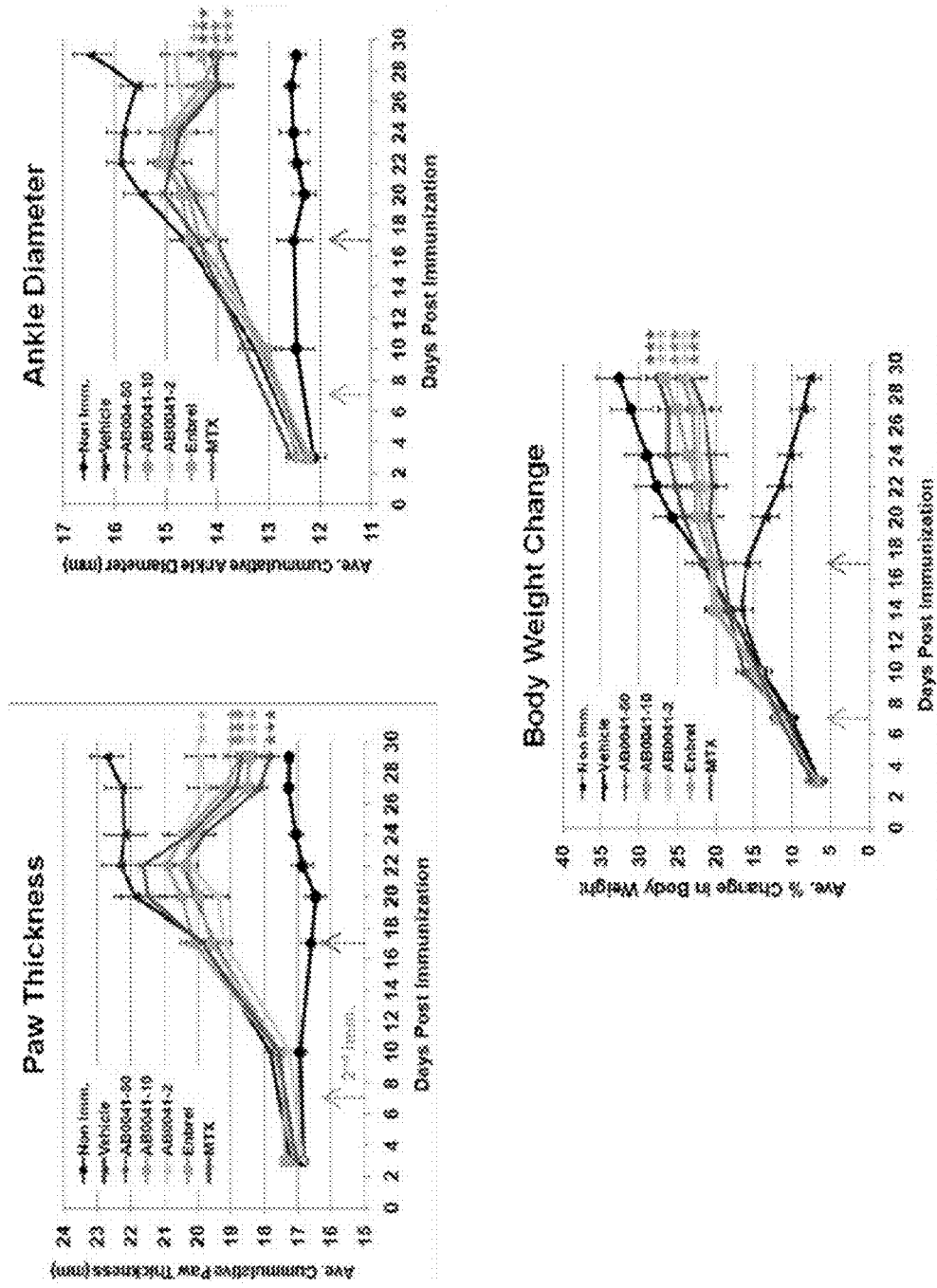
Figure 26: Anti-MMP9 Antibody in Rat CIA Model of Rheumatoid Arthritis

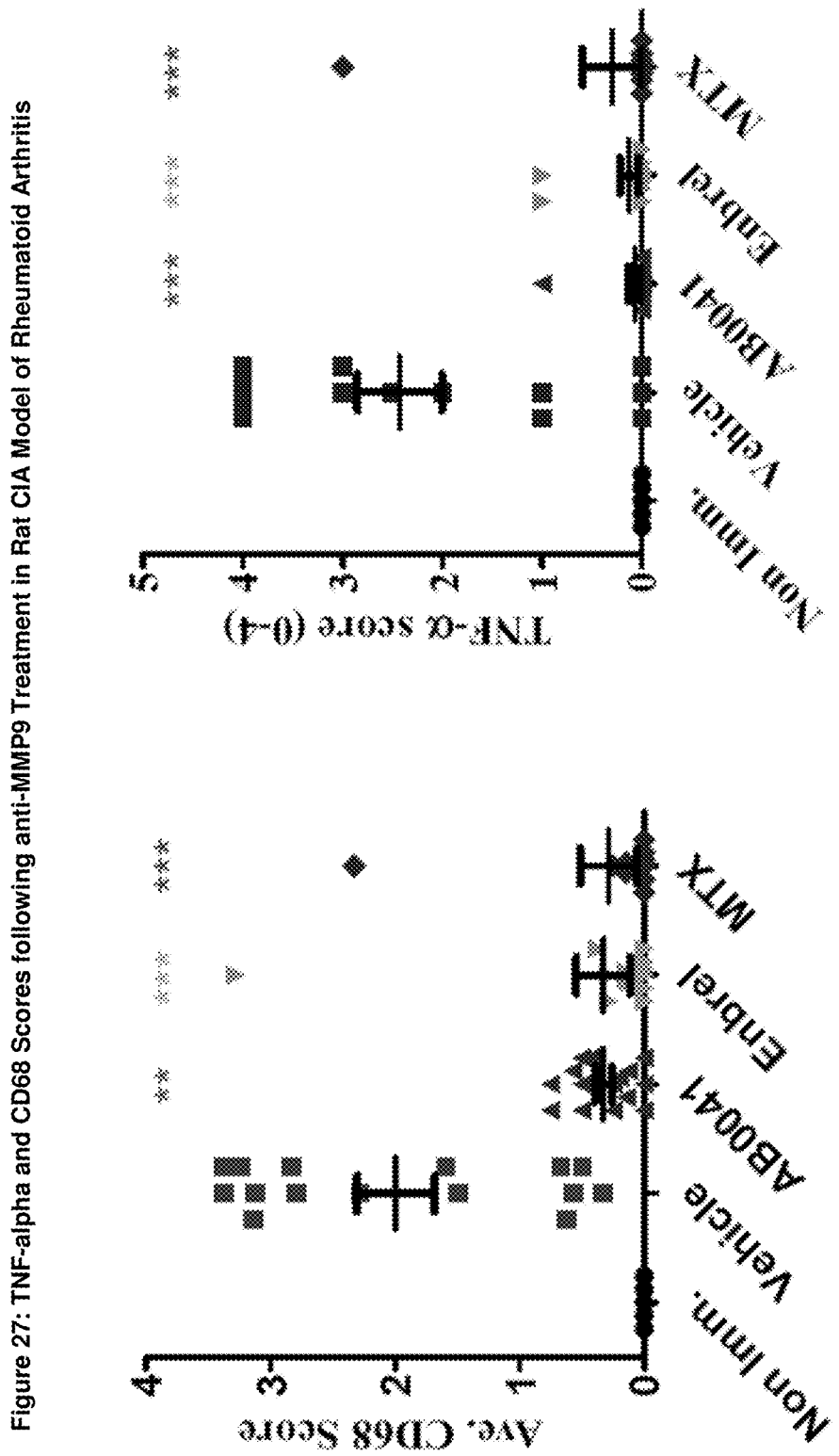
Figure 27: TNF-alpha and CD68 Scores following anti-MMP9 Treatment in Rat CIA Model of Rheumatoid Arthritis

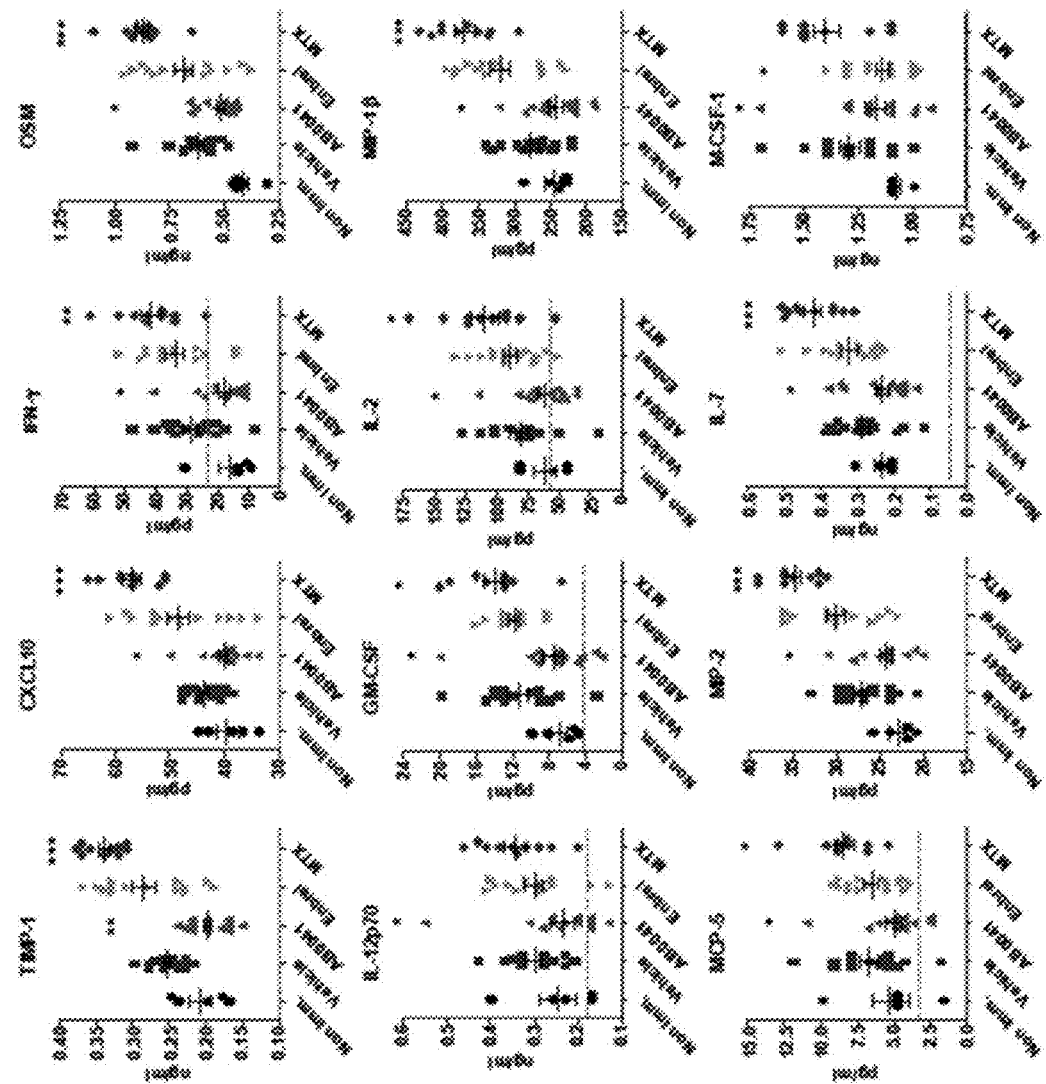
Figure 28: Serum Markers Following anti-MMP9 Treatment in Rat CIA Model of Rheumatoid Arthritis

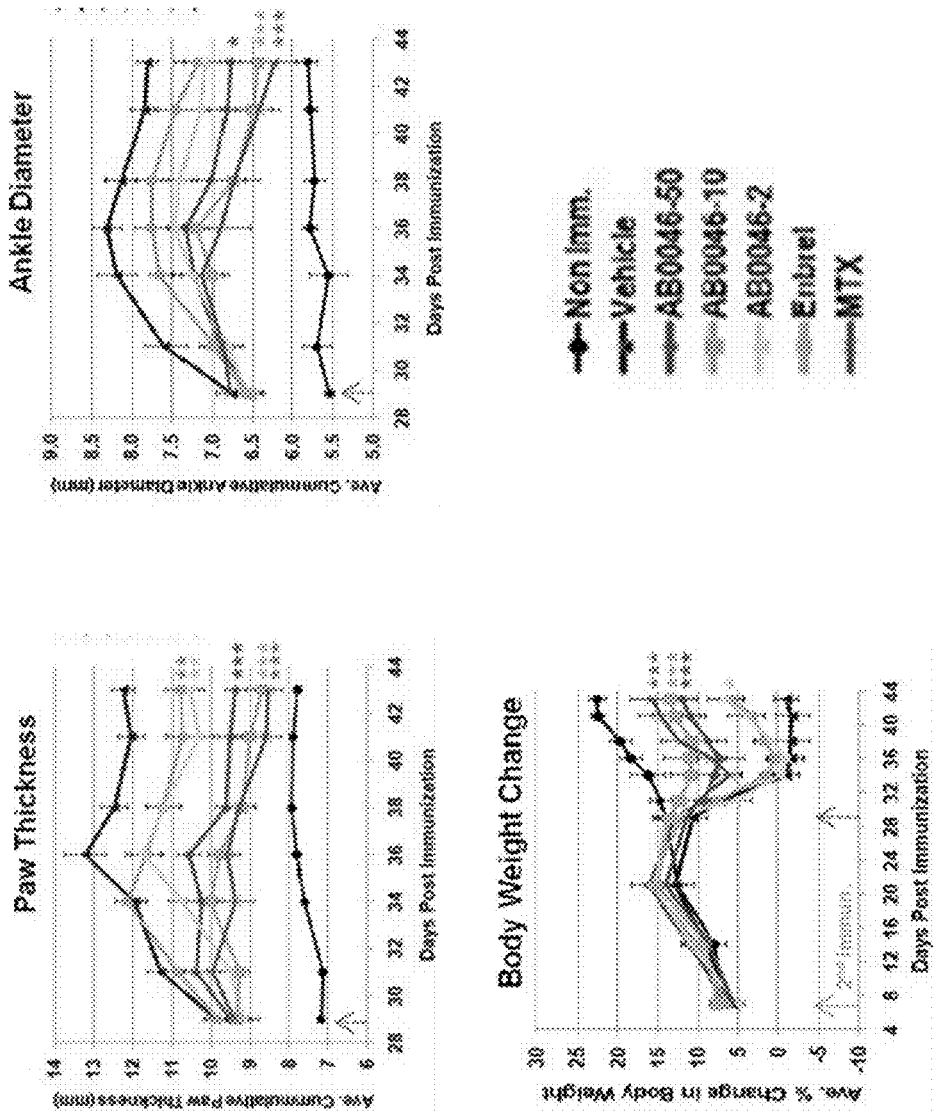
Figure 29: Anti-MMP9 Antibody in Mouse CIA Model of Rheumatoid Arthritis

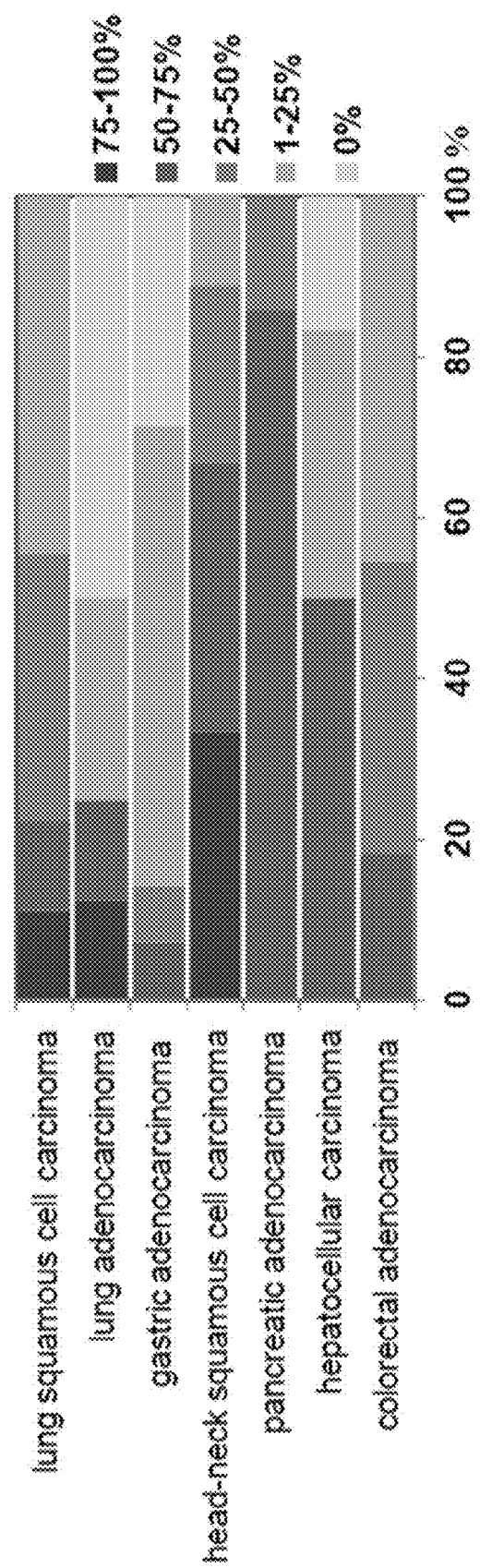
Figure 30: IHC analysis of MMP9-positivity in tumor epithelia

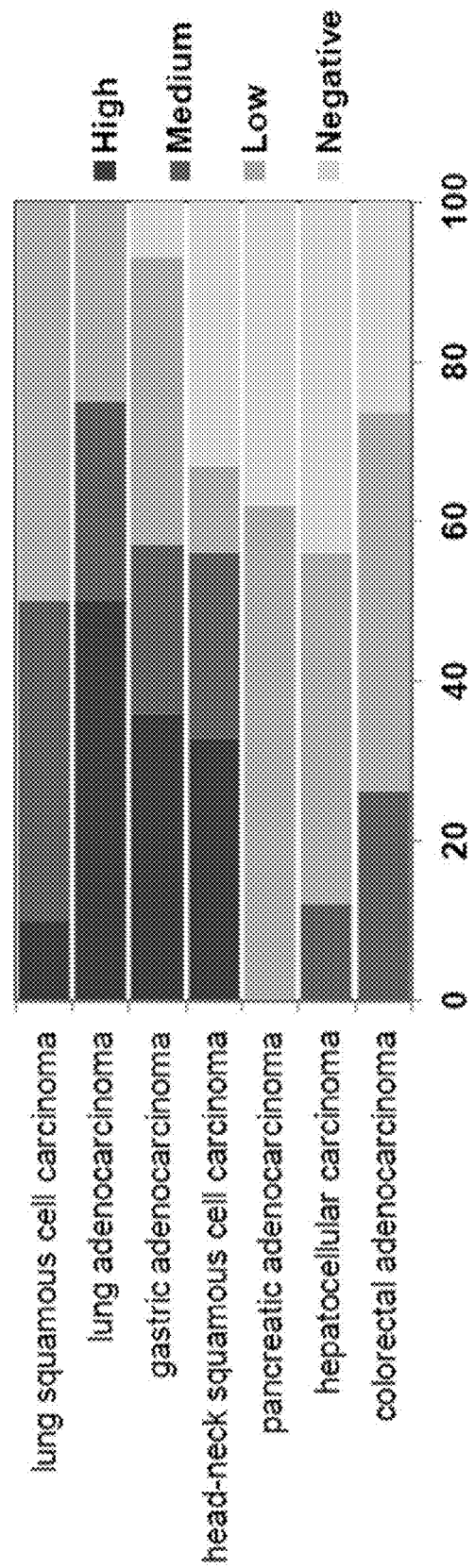
Figure 31: CISH analysis of MMP9-positivity in tumor epithelia

METHODS OF TREATING RHEUMATOID ARTHRITIS USING ANTIBODIES TO MATRIX METALLOPROTEINASE 9

CROSS-REFERENCE TO RELATED APPLICATIONS

This application claims priority from U.S. provisional application 61/605,181, filed Feb. 29, 2012, U.S. provisional application 61/755,444, filed Jan. 22, 2013, and PCT Application No. PCT/US2012/027160, filed on Feb. 29, 2012. The contents of these documents are incorporated herein by reference in their entirety.

STATEMENT OF RIGHTS TO INVENTIONS MADE UNDER FEDERALLY SPONSORED RESEARCH

Not applicable.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 246102008400SeqList.txt, date recorded: Feb. 28, 2013, size: 65,252 bytes).

FIELD

This disclosure is in the field of extracellular enzymes, extracellular matrix enzymes, proteases and immunology.

BACKGROUND

Matrix metalloproteinases (MMPs) belong to a family of extracellular enzymes involved in forming and remodeling the extracellular matrix. These enzymes contain a conserved catalytic domain in which a zinc atom is coordinated by three histidine residues. Over 20 members of this family are known, organized into a number of groups including collagenases, gelatinases, stromelysins, matrilysins, enamelysins and membrane MMPs.

MMP2 and MMP9 belong to the gelatinase group of matrix metalloproteinases. Besides containing signal peptide, propeptide, catalytic, zinc-binding and heamopexin-like domains common to most MMPs, the gelatinases also contain a plurality of fibronectin-like domains and an O-glycosylated domain.

MMPs are involved in a number of diseases. Inhibitors of MMPs have not been entirely satisfactory, in part related to specificity and efficacy. Thus, there is a need for specific and effective MMP inhibitors. Treatment of cancers and inflammatory and autoimmune diseases, such as colorectal cancer, IBD (including Crohn's disease (CD), ulcerative colitis (UC), and indeterminate colitis), rheumatoid arthritis (RA), and others, have not been entirely satisfactory. Thus, there is a need for treatments effective in such diseases, particularly for subjects in which available therapeutics have been ineffective.

SUMMARY

The present disclosure provides compositions and methods of use involving binding proteins, e.g., antibodies and antigen-binding fragments thereof, that bind to matrix metalloproteinase-9 (MMP9) protein (also known as gelatinase-B). The binding proteins typically are antibodies or fragments (e.g., antigen-binding fragments) thereof and typically contain an immunoglobulin (Ig) heavy chain (or functional fragment thereof) and an Ig light chain (or functional fragment thereof). The heavy chain is typically an IgG, such as an IgG1 or IgG4, or modified version thereof. The light chain typically is a kappa chain.

Among the MMP9 binding proteins, e.g., antibodies, are those that bind specifically to MMP9 and not to other, related matrix metalloproteinases. Such MMP9 binding proteins find use in applications in which it is necessary or desirable to obtain specific modulation (e.g., inhibition) of MMP9, e.g., without directly affecting the activity of other matrix metalloproteinases. Thus, in certain embodiments of the present disclosure an anti-MMP9 antibody or fragment thereof is a specific inhibitor of the activity of MMP9. In some aspects, the MMP9 binding proteins disclosed herein will be useful for inhibition of MMP9 while allowing normal function of other, related matrix metalloproteinases.

The antibodies and fragments can be described with reference to their amino acid sequences or portions thereof, and/or various functions such as binding specificity to MMP9 or particular epitopes thereof or the ability to compete for binding with particular antibodies, and/or activity, such as the ability to inhibit MMP9, e.g., non-competitively.

The antibodies and fragments can be part of a pharmaceutical composition, wherein the antibodies and fragments thereof that bind to Matrix Metalloproteinase 9 comprise a heavy chain variable (VH) region having a heavy chain complementary determining region (CDR) with an amino acid sequence of SEQ ID NO: 15 and a pharmaceutically acceptable excipient. The VH region may further comprise CDR with the amino acid sequence of SEQ ID NOs: 13 and/or 14. The VH region may also comprise the amino acid sequence as set forth in SEQ ID NOs: 3, 5, 6, 7, or 8. The VH region may also comprise the amino acid sequence that has a 95% sequence identify to the amino acid sequence as set forth in SEQ ID NOs: 3, 5, 6, 7, or 8.

In another embodiment, the disclosed pharmaceutical composition comprising an antibodies and antigen-binding fragments thereof that bind to Matrix Metalloproteinase 9 comprise a light chain variable (VL) region having a light chain complementary determining region (CDR) with an amino acid sequence of SEQ ID NO: 18 and a pharmaceutically acceptable excipient. The VL region may further comprises with the amino acid sequence of SEQ ID NOs: 16 and/or 17. The VL region may also comprise the amino acid sequence as set forth in SEQ ID NOs: 4, 9, 10, 11, or 12. The VL region may also comprise the amino acid sequence that have a 95% sequence identify to the amino acid sequence as set forth in SEQ ID NOs: 4, 9, 10, 11, or 12. In one embodiment, the VH region has the amino acid sequence set forth in SEQ ID NO: 7 and the VL region has the amino acid sequence set forth in SEQ ID NO: 12.

In another embodiment, the MMP9 binding protein comprises a VH region comprising a CDR with an amino acid sequence selected from the group consisting of SEQ ID NOs: 13, 14, 15, 34, 35, 36 and 47; and a VL region having a CDR with an amino acid sequence selected from the group consisting of SEQ ID NOs: 16, 17, 18, 37, 38, 39, 42, 43, 44, and 48. Also, the MMP9 binding protein may comprise a VH region has the amino acid sequence selected from the group consisting of SEQ ID NOs: 1, 3, 5, 6, 7, 8, 34, 35, 36, and 46; and a VL region has the amino acid sequence selected from the group consisting of SEQ ID NOs: 2, 4, 9, 10, 11, 12, 37, 38, 39, 42, 43, 44, and 45. In addition, the MMP9 binding protein may comprise the VH region has a 95% sequence identify to the amino acid sequence selected from the group consisting of SEQ ID NOs: 30, 32, 46, and 47; and the VL region has a 95% sequence identify to the amino acid sequence selected from the group consisting of SEQ ID NOs: 31, 33, 41, 45, and 48. Moreover, the MMP9 binding protein may comprise a VH region has the amino acid sequence selected from the group consisting of SEQ ID NOs: 30, 32, 46, and 47; and the VL region has the amino acid sequence selected from the group consisting of SEQ ID NOs: 31, 33, 41, 45, and 48.

Another embodiment of the invention relates to a pharmaceutical composition, comprising an isolated antibody or fragment thereof that specifically binds to an epitope of MMP9, wherein the epitope comprises an amino acid residue within a region of MMP9, the region consisting of residues 104-119, residues 159-166, or residues 191-202 of SEQ ID NO: 27; and a pharmaceutically acceptable excipient. In one aspect, the epitope comprises E111, D113, R162, or I198 of SEQ ID NO: 27.

In another embodiment, the disclosed pharmaceutical compositions further comprising one or more therapeutic agents selected from the group consisting of an anti-inflammatory agent, an immunotherapeutic agent, a chemotherapeutic agent, an anti-cancer agent, an anti-fibrotic agent, or a combination thereof. Examples of a therapeutic agent include but are not limited to nab-paclitaxel, mFOLFOX6, FOLFIRI, carboplatin, paclitaxel, pemetrexed, bevacizumab, anti-lysyl oxidase-like 2 (LOXL2) antibodies, an anti-discoidin domain receptor 1 (DDR1) antibodies, or a combination thereof.

Also provided are methods of inhibiting MMP9 activity in a subject and/or treating a disease or condition in the subject, for example, using an agent that non-competitively inhibits MMP9, and agents (such as any of the above-described anti-MMP9 antibodies and other MMP9 binding proteins) for use in such methods. The methods generally are carried out by administering to the subject an MMP9 binding protein, such as an MMP9-binding antibody or fragment thereof as provided herein, such as any of those described above, e.g., in an effective amount. The antibody or fragment generally specifically binds to and non-competitively inhibits MMP9, typically such that MMP9 activity is inhibited in the subject. In some cases, the antibody or fragment is one that binds MMP9 outside the catalytic domain, such as in one of the epitopes described above. In some cases, the antibody or fragment does not substantially bind to an MMP protein other than MMP9 and/or does not substantially bind to MMP2. Further provided are methods of detecting or monitoring MMP9 activity comprising contacting a sample with MMP9 binding protein, and assessing the presence or absence of MMP9 binding protein-MMP9 complex; wherein the absence of the MMP9 binding protein-MMP9 complex indicates the sample does not have the MMP9 activity, and the presence of the MMP9 binding protein-MMP9 complex indicates the sample has the MMP9 activity. The MMP9 activity may be detected by using any of the MMP9 binding protein disclosed herein.

Also provided are methods and uses of the pharmaceutical compositions disclosed here, where a subject in need thereof that has an MMP-9-associated disease or condition is administered an effective amount of the disclosed antibodies or fragments thereof or the pharmaceutical composition comprising the disclosed antibodies or fragments thereof that is effective to inhibit MMP9 activity in the subject. Examples of MMP9-associated diseases or conditions include but are not limited to cancers, autoimmune, inflammatory, or fibrotic diseases or conditions. Examples of MMP9-associated cancers include but are not limited to pancreatic cancer, esophagogastric adenocarcinoma, non-small cell lung cancer, lung squamous cell carcinoma, lung adenocarcinoma, gastric adenocarcinoma, colorectal carcinoma, pancreatic adenocarcinoma, head and neck squamous cell carcinoma, hepatocellular carcinomacolorectal cancer, colorectal adenocarcinoma, or hepatocellular carcinoma. Examples of MMP9-associated autoimmune or inflammatory disease or condition is rheumatoid arthritis, an inflammatory bowel disease (IBD), septicemia, multiple sclerosis, muscular dystrophy, lupus, allergy, or asthma. Examples of IBD include but are not limited to ulcerative colitis (UC), Crohn's disease (CD), or indeterminate colitis.

In some examples, the antibody or the pharmaceutical composition thereof is administered at a dose from about 1 mg/kg to about 28 mg/kg. In some examples, the antibody or the pharmaceutical composition thereof is administered at a dosage of between at or about 100 and at or about 1800 mg/Kg body weight.

In some examples, the antibody or the pharmaceutical composition thereof is administered at a dosage at or about 100, 300, 400, 500, 600, 700, 800, 900, 1000, 1100, 1200, 1300, 1400, 1500, 1600, 1700, or 1800 mg/Kg body weight. In some examples, the antibody is administered the interval of one, two or three weeks, or once every one, two, or three weeks. In some examples, the antibody or fragment thereof is administered intravenously or subcutaneously.

In some embodiments, the antibody or the pharmaceutical composition thereof is administered alone, as a monotherapy. In other embodiments, the antibody or the pharmaceutical composition thereof is administered as part of a combination therapy with one or more other therapeutic agents. The therapeutic agents include but not limited to anti-sd-inflammatory agent, an immunotherapeutic agent, a chemotherapeutic agent, an anti-cancer agent, an anti-fibrotic agent, or a combination thereof. The one or more other therapeutic agents can be administered concurrently or sequentially with the antibody or fragments thereof.

BRIEF DESCRIPTION OF THE DRAWINGS

FIG. 1 shows the amino acid sequence of the heavy chain variable region of a mouse monoclonal anti-MMP9 antibody (AB0041), along with the amino acid sequences of humanized variants of heavy chain (VH1-VH4), aligned to show differences in framework amino acid sequence resulting from humanization. CDRs are shown in italics, and amino acids that are different in the humanized variants, compared to the parent mouse monoclonal, are underlined.

FIG. 2 shows the amino acid sequence of the light chain variable region of a mouse monoclonal anti-MMP9 antibody (AB0041), along with the amino acid sequences of humanized variants of this light chain (VH1-VH4), aligned to show differences in framework amino acid sequence resulting from humanization. CDRs are shown in italics, and amino acids that are different in the humanized variants, compared to the parent mouse monoclonal, are underlined.

FIG. 4 shows a comparison between the amino acid sequences of the heavy and light chains of antibodies designated AB0041, M4, and M12.

FIG. 5 shows results from immunohistochemistry (IHC) performed on frozen serial sections of colons from Vehicle-treated (A) and AB0046-treated (B) mice as described in Example 4, highlighting inflammation and tissue destruction observed in DSS-induced colitis. MMP9 expression was observed in infiltrating neutrophils (indicated by MPO signal) and macrophages and co-localized with basement membrane collagen IV (labeled "CoIIV" in the figure), and MMP9 substrate. Diseased colons (A) exhibit destruction of the mucosal epithelium and submucosal crypts and a robust inflammatory cell infiltrate. Little evidence of MMP2 expression was observed in diseased tissue (A).

FIG. 6 shows representative images from MMP9 immunohistochemistry (IHC) on formalin-fixed, paraffin-embedded (FFPE) sections taken from colons as described in Example 4. As shown, epithelial cell MMP9 expression (arrows) was minimal in normal colons (−DSS) and highly induced after DSS administration (+DSS).

FIG. 7 shows the results of endoscopic evaluation, performed on all groups of animals on study days 10 and 14 (day of termination) in the study described in Example 4. Panel A shows mean endoscopy score (+/−SEM) at days 6-14, with arrows indicating days of AB0046 (or other treatment) administration. Panel B shows mean endoscopy score (+/−SEM) at day 14 for each group, with asterisks indicating significant reduction in disease (which was observed for AB0046 and ENBREL® treatment groups at Day 14). Endoscopic score reflects the most severe lesion observed for each animal.

FIG. 8 shows the results of histopathological analysis, performed on colons excised at termination of the study described in Example 4. The degree of inflammation, edema, and necrosis was assessed and a sum score calculated by adding the mean colon score from each animal for each parameter assessed. Anti-MMP9 (AB0046) treatment significantly reduced histopathological disease to an extent similar to ENBREL®.

FIG. 9 shows representative images of MMP9 IHC on FFPE sections of colons from the study described in Example 4. MMP9 expression was minimal in normal colons (No DSS) and was highly induced after DSS administration (Vehicle). Reduction of MMP9 expression in AB0046 and ENBREL® treatment groups correlated with reduction in overall disease.

FIG. 10 shows body weight and diarrhea results for the study described in Example 4. The area under the curve (AUC) was calculated for body weight changes and diarrhea incidence by the trapezoidal rule method. Treatment with anti-MMP9 antibody (AB0046) was protective against body weight loss due to DSS-induced colitis and comparable to the effect of ENBREL® treatment. The incidence of diarrhea was similarly reduced with AB0046 and ENBREL® treatment.

FIG. 11A shows results of a multi-analyte ELISA analysis performed as described in Example 4 on terminal serum samples in a DSS colitis model following treatment with anti-MMP9 antibody (AB0046) and other treatments. The results revealed a broad systemic downregulation of disease-induced inflammatory cytokines and growth factors with AB0046 treatment. FIG. 11B shows additional serum marker data from the same study.

FIG. 12A shows a reduction of endoscopic disease by anti-MMP9 antibody (AB0047) treatment in the DSS colitis model in the study described in Example 4. FIG. 12B shows a Reduction in histological disease by anti-MMP9 antibody (AB0047) treatment in the DSS colitis model in the study described in Example 4.

FIG. 13 shows the results of endoscopic evaluation, performed on all groups of animals on indicated days in the prophylactic treatment study described in Example 5. Panel A shows mean endoscopy score (+/−SEM) at days 6-14, with arrows indicating days of AB0046 (or other treatment) administration. Panel B shows mean endoscopy score (+/−SEM) at day 10 for each group, with asterisks indicating significant reduction in disease (which was observed for AB0046 and ENBREL® treatment groups at Day 14). Endoscopic score reflects the most severe lesion observed for each animal.

FIG. 14 shows the results of histopathological analysis, performed on colons excised at termination of the study described in Example 5. The degree of inflammation, edema, and necrosis was assessed and a sum score calculated by adding the mean colon score from each animal for each parameter assessed.

FIG. 15 shows body weight and diarrhea results for the study described in Example 5. The area under the curve (AUC) was calculated for body weight changes and diarrhea incidence by the trapezoidal rule method. Prophylactic treatment with anti-MMP9 antibody (AB0046) was protective against incidence of diarrhea.

FIG. 16 shows decrease in primary tumor growth in an established colorectal tumorigenesis model (HCT116) in the study described in Example 6. The left panel shows decreased change in tumor volume; the right panel shows decreased final tumor weight at day 32 after initiation of treatment (with p-values derived from Mann-Whitney test and bars representing group mean±SEM).

FIG. 17A shows clinical and leg score results from the study described in Example 7, showing efficacy of murine surrogate anti-MMP9 (AB0046) and anti-human MMP9 (AB0041) antibodies in mouse and rat CIA models of rheumatoid arthritis. FIG. 17B shows anti-MMP9 antibody titers from the same study. MTX=methotrexate; Non Dis.=non-diseased.

FIG. 18A shows end-of-study serum levels of inflammatory cytokines in the rat CIA study described in Example 7; FIG. 18B shows end-of-study levels of serum inflammatory cytokines in the mouse CIA study described in Example 7. MTX=methotrexate; Non Dis.=non-diseased.

FIG. 19A shows additional serum markers in the rat CIA study described in Example 7; FIG. 19B shows additional serum markers in the mouse CIA study described in Example 7. MTX=methotrexate; Non Dis.=non-diseased.

FIG. 20 shows protection against death and body temperature loss following anti-MMP9 administration in an LPS septicemia rat model as described in Example 8. The lower line in each graph represents the AC-1-treated group and the two upper lines represent the group receiving no LPS (diamonds in left panel; circles in right panel) and the anti-MMP9-treated group (squares in left panel and triangles in right panel).

FIG. 21 shows mean daily musculoskeletal syndrome (MSS) scores±standard deviation for AB0041-, Marimastat-, and control-treated rats.

FIG. 22 shows AB0041 serum levels (serum titers) as measured by ELISA in AB0041-treated rats at days 1, 7, 10, 14, 17, 21, 24, and 28. Data are presented as mean value±standard deviation.

FIG. 23 shows change in tumor volume (FIGS. 23A, 23C, 23E) and weight (FIGS. 23B, 23D, 23F) following the indicated treatments in a mouse xenograft model of colorectal cancer.

FIG. 24 shows change in tumor volume (FIG. 24A) and weight (FIG. 24B) following the indicated treatments in a mouse xenograft model of colorectal cancer.

FIG. 25 shows levels of serum proteins following control and anti-MMP9 treatment in a mouse xenograft model of colorectal cancer.

FIG. 26 shows changes in paw thickness, ankle diameter, and body weight in a rat CIA model of rheumatoid arthritis after the indicated treatment.

FIG. 27 shows TNF-alpha and CD68 Scores following the indicated treatment in a rat CIA model of rheumatoid arthritis, as measured by immunohistochemistry.

FIG. 28 shows end-of-study serum levels of inflammatory cytokines in a rat CIA study.

FIG. 29 shows changes in paw thickness, ankle diameter, and body weight in a mouse CIA model of rheumatoid arthritis after the indicated treatment.

FIG. 30 shows results from IHC analysis of tumor epithelial-associated MMP9 protein.

FIG. 31 shows results from CISH analysis of tumor epithelial-associated MMP9 mRNA:

DETAILED DESCRIPTION

Figure 3:
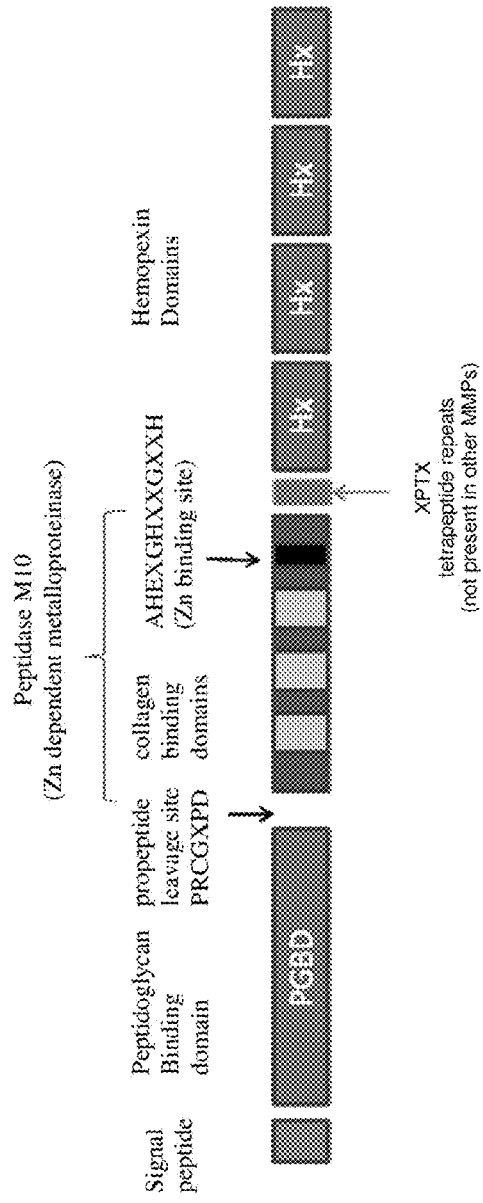
FIG. 3 shows a schematic diagram of the MMP9 protein.

Practice of the present disclosure employs, unless otherwise indicated, standard methods and conventional techniques in the fields of cell biology, toxicology, molecular biology, biochemistry, cell culture, immunology, oncology, recombinant DNA and related fields as are within the skill of the art. Such techniques are described in the literature and thereby available to those of skill in the art. See, for example, Alberts, B. et al., "Molecular Biology of the Cell," 5th edition, Garland Science, New York, N.Y., 2008; Voet, D. et al. "Fundamentals of Biochemistry: Life at the Molecular Level," $3^{rd}$ edition, John Wiley & Sons, Hoboken, N.J., 2008; Sambrook, J. et al., "Molecular Cloning: A Laboratory Manual," $3^{rd}$ edition, Cold Spring Harbor Laboratory Press, 2001; Ausubel, F. et al., "Current Protocols in Molecular Biology," John Wiley & Sons, New York, 1987 and periodic updates; Freshney, R. I., "Culture of Animal Cells: A Manual of Basic Technique," $4^{th}$ edition, John Wiley & Sons, Somerset, N.J., 2000; and the series "Methods in Enzymology," Academic Press, San Diego, Calif. See also, for example, "Current Protocols in Immunology," (R. Coico, series editor), Wiley, last updated August 2010.

Abnormal activity of certain MMPs plays a role in tumor growth, metastasis, inflammation, autoimmunity, and vascular disease. See, for example, Hu et al. (2007) *Nature Reviews: Drug Discovery* 6:480-498. One notable source of MMP9 is tumor-associated macrophages (TAMs), which support metastasis and invasion in a complex co-activation loop via paracrine interaction with the primary tumor cells. This combination of the proteolytic breakdown of physical barriers to cell invasion plus liberation of factors that activate growth and angiogenesis paves the way for tumor expansion, with the accompanying development of neovascularization to support tumor outgrowth.

MMP9 is a target of oncogenic signaling pathways such as RAS/RAF, PI3K/AKT/NFkB, and WNT/beta-catenin and functions as an upstream regulator of these pathways via modulation of integrin and receptor tyrosine kinase function. MMP9 is elevated in a wide variety of tumor types and MMP9 levels are correlated with poor prognosis in many cancers, including gastric, lung, and colorectal cancer. MP9 is also implicated in chemoresistance and is upregulated upon loss of several tumor suppressors. MMP9 is upregulated in many diverse tumor types and can promote primary growth and distal invasion of cancerous cells.

It can be desirable to inhibit the activity of one or more MMPs in certain therapeutic settings. However, the activity of certain other MMPs, e.g., MMP2, is often required for normal function and/or is protective against disease. Since most MMP inhibitors are targeted to the conserved catalytic domain and, as a result, inhibit a number of different MMPS, use of available MMP inhibitors has caused side effects due to the inhibition of essential, non-pathogenically-related MMPs.

Challenges associated with developing inhibitors specific to a particular MMP or select MMPs relate to the fact that inhibition of enzymatic activity generally requires that the inhibitor be targeted to the catalytic domain. Homologies in MMP catalytic domains can cause inhibitors to react with more than one MMP. Among the provided embodiments are agents, including therapeutic reagents, such as antibodies and antigen-binding fragments thereof, that specifically inhibit the catalytic activity of a single MMP or a select plurality of MMPs, such as MMP9 and that do not react with or inhibit certain other MMPs or any other MMPs. Also among the provided embodiments are methods and uses of the same for treatment of various diseases, including cancers and autoimmune and inflammatory diseases.

MMP9 Binding Proteins

MMP9 degrades basement membrane collagen and other extracellular matrix (ECM) components. Kessenbrock K, et al., "Matrix metalloproteinases: regulators of the tumor microenvironment." Cell 2010; 141 (1):52-67. Matrix degradation contributes to pathology in multiple diseases, including arthritis, cancer, and ulcerative colitis. Roy R, et al., "Matrix metalloproteinases as novel biomarkers and potential therapeutic targets in human cancer." J Clin Oncol 2009; 27 (31):5287-97. Broad-spectrum matrix metalloproteinase inhibitors such as Marimastat are efficacious in animal models of inflammation and cancer (Watson S A, et al., "Inhibition of tumour growth by marimastat in a human xenograft model of gastric cancer: relationship with levels of circulating CEA." Br J Cancer 1999; 81 (1):19-23; Sykes A P, et al., "The effect of an inhibitor of matrix metalloproteinases on colonic inflammation in a trinitrobenzenesulphonic acid rat model of inflammatory bowel disease." Aliment Pharmacol Ther 1999; 13 (11):1535-42.). Such pan inhibitors, however, can cause musculoskeletal side effects including joint stiffness, inflammation, and pain in the hands, arms, and shoulders, collectively referred to as musculoskeletal syndrome (MSS), typically at or near efficacious dose levels of Marimastat in humans. Peterson J T. "The importance of estimating the therapeutic index in the development of matrix metalloproteinase inhibitors." Cardiovasc Res 2006; 69 (3):677-87; Tierney G M, et al. "A pilot study of the safety and effects of the matrix metalloproteinase inhibitor marimastat in gastric cancer." Eur J Cancer 1999; 35 (4):563-8; Wojtowicz-Praga S, et al. "Phase I trial of Marimastat, a novel matrix metalloproteinase inhibitor, administered orally to patients with advanced lung cancer." J Clin Oncol 1998; 16 (6):2150-6. The symptoms are dose- and time-dependent, and reversible shortly after cessation of treatment with the pan-MMP inhibitor. Wojtowicz-Praga S, 1998; Nemunaitis J, et al., "Combined analysis of studies of the effects of the matrix metalloproteinase inhibitor marimastat on serum tumor markers in advanced cancer: selection of a biologically active and tolerable dose for longer-term studies." Clin Cancer Res 1998; 4 (5):1101-9; Hutchinson J W et al., "Dupuytren's disease and frozen shoulder induced by treatment with a matrix metalloproteinase inhibitor." The Journal of bone and joint surgery. British volume 1998; 80 (5):907-8. Marimastat and other pan-MMP inhibitors of the same class are zinc chelators. Peterson J T, 2006. The homozygous MMP9 knockout mouse displays no MSS-like symptoms or MSS-like tissue changes. Vu T H, et al., "MMP-9/gelatinase B is a key regulator of growth plate angiogenesis and apoptosis of hypertrophic chondrocytes." Cell 1998; 93 (3):411-22.

The present disclosure provides binding proteins, e.g., antibodies and fragments (e.g., antigen-binding fragments) thereof, that bind to the matrix metalloproteinase-9 (MMP9) protein (MMP9 is also known as gelatinase-B), e.g., human MMP9, such as the human MMP9 having an amino acid sequence set forth in SEQ ID NO: 27 or SEQ ID NO: 28. The binding proteins of the present disclosure generally comprise an immunoglobulin (Ig) heavy chain (or functional fragment thereof) and an Ig light chain (or functional fragment thereof).

The disclosure further provides MMP9 binding proteins that bind specifically to MMP9 and not to other matrix metalloproteinases such as MMP1, MMP2, MMP3, MMP7, MMP9, MMP10, MMP12, and MMP13. Such specific MMP9 binding proteins are thus generally not significantly or detectably crossreactive with non-MMP9 matrix metalloproteinases. MMP9 binding proteins that specifically bind MMP9 find use in applications in which it is necessary or desirable to obtain specific modulation (e.g., inhibition) of MMP9, e.g., without directly affecting the activity of other matrix metalloproteinases.

In certain embodiments of the present disclosure an anti-MMP9 antibody is an inhibitor of the activity of MMP9, and can be a specific inhibitor of MMP9. In particular, the MMP9 binding proteins disclosed herein will be useful for inhibition of MMP9 while allowing normal function of other, related matrix metalloproteinases. "An inhibitor of MMP" or "inhibitor of MMP9 activity" can be an antibody or an antigen binding fragment thereof that directly or indirectly inhibits activity of MMP9, including but not limited to enzymatic processing, inhibiting action of MMP9 on it substrate (e.g., by inhibiting substrate binding, substrate cleavage, and the like), and the like.

In some embodiments, as demonstrated in examples herein, whereas treatment with pan-MMP inhibitors, such as small-molecule pan inhibitors such as Marimastat, result in symptoms of musculoskeletal disease, such as musculoskeletal syndrome (MSS), including substantial effects on gait, posture and willingness to move, specific inhibition of MMP9 such as the antibodies or antigen-binding fragments thereof in the present application, does not cause such symptoms and does not induce MSS.

The present disclosure also provides MMP9 binding proteins that specifically bind to non-mouse MMP9, such as human MMP9, Cynomolgus monkey MMP9, and rat MMP9.

The present disclosure also provides MMP9 binding proteins (e.g., anti-MMP9 antibodies and functional fragments thereof) that act as non-competitive inhibitors. A "non-competitive inhibitor" refers to an inhibitor binds at site away from substrate binding site of an enzyme, and thus can bind the enzyme and effect inhibitory activity regardless of whether or not the enzyme is bound to its substrate. Such non-competitive inhibitors can, for example, provide for a level of inhibition that can be substantially independent of substrate concentration.

MMP9 binding proteins (e.g., antibodies and functional fragments thereof) of the present disclosure include those that bind MMP9, particularly human MMP9, and having a heavy chain polypeptide (or functional fragment thereof) that has at least about 80%, 85%, 90%, 95% or more amino acid sequence identity to a heavy chain polypeptide disclosed herein. In some example, MMP9 binding proteins (e.g., antibodies and functional fragments thereof) of the present disclosure include those that bind MMP9, particularly human MMP9, and having a heavy chain polypeptide (or functional fragment thereof) that has at least about 90%, 95%, 97%, 98%, 99% or more amino acid sequence identity to a heavy chain polypeptide disclosed herein.

MMP9 binding proteins (e.g., antibodies and functional fragments thereof) of the present disclosure include those that bind MMP9, particularly human MMP9, and having a light polypeptide (or functional fragment thereof) that has at least about 80%, 85%, 90%, 95% or more amino acid sequence identity to a heavy chain polypeptide disclosed herein.

MMP9 binding proteins (e.g., antibodies and functional fragments thereof) of the present disclosure include those that bind MMP9, particularly human MMP9, and have a heavy chain polypeptide (or functional fragment thereof) having the complementarity determining regions ("CDRs") of heavy chain polypeptide and the CDRs of a light chain polypeptide (or functional fragment thereof) as disclosed herein.

"Homology" or "identity" or "similarity" as used herein in the context of nucleic acids and polypeptides refers to the relationship between two polypeptides or two nucleic acid molecules based on an alignment of the amino acid sequences or nucleic acid sequences, respectively. Homology and identity can each be determined by comparing a position in each sequence which may be aligned for purposes of comparison. When an equivalent position in the compared sequences is occupied by the same base or amino acid, then the molecules are identical at that position; when the equivalent site occupied by the same or a similar amino acid residue (e.g., similar in steric and/or electronic nature), then the molecules can be referred to as homologous (similar) at that position. Expression as a percentage of homology/similarity or identity refers to a function of the number of identical or similar amino acids at positions shared by the compared sequences. In comparing two sequences, the absence of residues (amino acids or nucleic acids) or presence of extra residues also decreases the identity and homology/similarity.

As used herein, "identity" means the percentage of identical nucleotide or amino acid residues at corresponding positions in two or more sequences when the sequences are aligned to maximize sequence matching, i.e., taking into account gaps and insertions. Sequences are generally aligned for maximum correspondence over a designated region, e.g., a region at least about 20, 25, 30, 35, 40, 45, 50, 55, 60, 65 or more amino acids or nucleotides in length, and can be up to the full-length of the reference amino acid or nucleotide. For sequence comparison, typically one sequence acts as a reference sequence, to which test sequences are compared. When using a sequence comparison algorithm, test and reference sequences are input into a computer program, subsequence coordinates are designated, if necessary, and sequence algorithm program parameters are designated. The sequence comparison algorithm then calculates the percent sequence identity for the test sequence(s) relative to the reference sequence, based on the designated program parameters.

Examples of algorithms that are suitable for determining percent sequence identity are the BLAST and BLAST 2.0 algorithms, which are described in Altschul et al. (1990) J. Mol. Biol. 215: 403-410 and Altschul et al. (1977) Nucleic Acids Res. 25: 3389-3402, respectively. Software for performing BLAST analyses is publicly available through the National Center for Biotechnology Information (www.ncbi.nlm.nih.gov). Further exemplary algorithms include ClustalW (Higgins D., et al. (1994) Nucleic Acids Res 22: 4673-4680), available at www.ebi.ac.uk/Tools/clustalw/index.html.

Residue positions which are not identical can differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine.

Sequence identity between two nucleic acids can also be described in terms of hybridization of two molecules to each other under stringent conditions. The hybridization conditions are selected following standard methods in the art (see, for example, Sambrook, et al., Molecular Cloning: A Laboratory Manual, Second Edition, (1989) Cold Spring Harbor, N.Y.). An example of stringent hybridization conditions is hybridization at 50° C. or higher and 0.1×SSC (15 mM sodium chloride/1.5 mM sodium citrate). Another example of stringent hybridization conditions is overnight incubation at 42° C. in a solution: 50% formamide, 5×SSC (150 mM NaCl, 15 mM trisodium citrate), 50 mM sodium phosphate (pH7.6), 5×Denhardt's solution, 10% dextran sulfate, and 20 mg/ml denatured, sheared salmon sperm DNA, followed by washing the filters in 0.1×SSC at about 65° C. Stringent hybridization conditions are hybridization conditions that are at least as stringent as the above representative conditions, where conditions are considered to be at least as stringent if they are at least about 80% as stringent, typically at least 90% as stringent as the above specific stringent conditions.

Accordingly, the present disclosure provides, for example, antibodies or antigen binding fragments thereof, comprising a heavy chain variable region polypeptide having at least 80%, 85%, 90%, 95%, 96%, 97%, 98%, 99% or greater amino acid sequence identity to an amino acid sequence of a heavy chain variable region described herein (e.g., SEQ ID NOS: 1 or 5-8), and a variable light chain polypeptide having at least 80%, 85%, 90%, 95%, 96%, 97%, 98%, 99% or greater amino acid sequence identity to an amino acid sequence of a light chain polypeptide as set forth herein (e.g., SEQ ID NOS: 2 or 9-12).

Examples of anti-MMP9 antibodies of the present disclosure are described in more detail below.

Antibodies

The MMP9 binding proteins include antibodies and functional fragments thereof, such as those that specifically bind to MMP9. As used herein, the term "antibody" means an isolated or recombinant polypeptide binding agent that comprises peptide sequences (e.g., variable region sequences) that specifically bind an antigenic epitope. The term is used in its broadest sense and specifically covers monoclonal antibodies (including full-length monoclonal antibodies), polyclonal antibodies, human antibodies, humanized antibodies, chimeric antibodies, nanobodies, diabodies, multispecific antibodies (e.g., bispecific antibodies), and antibody fragments including but not limited to Fv, scFv, Fab, Fab' F(ab')$_2$ and Fab$_2$, so long as they exhibit the desired biological activity. The term "human antibody" refers to antibodies containing sequences of human origin, except for possible non-human CDR regions, and does not imply that the full structure of an immunoglobulin molecule be present, only that the antibody has minimal immunogenic effect in a human (i.e., does not induce the production of antibodies to itself).

An "antibody fragment" comprises a portion of a full-length antibody, for example, the antigen binding or variable region of a full-length antibody. Such antibody fragments may also be referred to herein as "functional fragments: or "antigen-binding fragments". Examples of antibody fragments include Fab, Fab', F(ab')$_2$, and Fv fragments; diabodies; linear antibodies (Zapata et al. (1995) *Protein Eng.* 8(10):1057-1062); single-chain antibody molecules; and multispecific antibodies formed from antibody fragments. Papain digestion of antibodies produces two identical antigen-binding fragments, called "Fab" fragments, each with a single antigen-binding site, and a residual "Fc" fragment, a designation reflecting the ability to crystallize readily. Pepsin treatment yields an F(ab')$_2$ fragment that has two antigen combining sites and is still capable of cross-linking antigen.

"Fv" is a minimum antibody fragment containing a complete antigen-recognition and -binding site. This region consists of a dimer of one heavy- and one light-chain variable domain in tight, non-covalent association. It is in this configuration that the three complementarity-determining regions (CDRs) of each variable domain interact to define an antigen-binding site on the surface of the $V_H$-$V_L$ dimer. Collectively, the six CDRs confer antigen-binding specificity to the antibody. However, even a single variable domain (or an isolated $V_H$ or $V_L$ region comprising only three of the six CDRs specific for an antigen) has the ability to recognize and bind antigen, although generally at a lower affinity than does the entire $F_v$ fragment.

The "$F_{ab}$" fragment also contains, in addition to heavy and light chain variable regions, the constant domain of the light chain and the first constant domain ($CH_1$) of the heavy chain. Fab fragments were originally observed following papain digestion of an antibody. Fab' fragments differ from Fab fragments in that F(ab') fragments contain several additional residues at the carboxy terminus of the heavy chain $CH_1$ domain, including one or more cysteines from the antibody hinge region. F(ab')$_2$ fragments contain two Fab fragments joined, near the hinge region, by disulfide bonds, and were originally observed following pepsin digestion of an antibody. Fab'-SH is the designation herein for Fab' fragments in which the cysteine residue(s) of the constant domains bear a free thiol group. Other chemical couplings of antibody fragments are also known.

The "light chains" of antibodies (immunoglobulins) from any vertebrate species can be assigned to one of two clearly distinct types, called kappa and lambda, based on the amino acid sequences of their constant domains. Depending on the amino acid sequence of the constant domain of their heavy chains, immunoglobulins can be assigned to five major classes: IgA, IgD, IgE, IgG, and IgM, and several of these may be further divided into subclasses (isotypes), e.g., IgG1, IgG2, IgG3, IgG4, IgA1, and IgA2.

"Single-chain Fv" or "sFv" or "scFv" antibody fragments comprise the $V_H$ and $V_L$ domains of antibody, wherein these domains are present in a single polypeptide chain. In some embodiments, the Fv polypeptide further comprises a polypeptide linker between the $V_H$ and $V_L$ domains, which enables the sFv to form the desired structure for antigen binding. For a review of sFv, see Pluckthun, in *The Pharmacology of Monoclonal Antibodies*, vol. 113 (Rosenburg and Moore eds.) Springer-Verlag, New York, pp. 269-315 (1994).

The term "diabodies" refers to small antibody fragments with two antigen-binding sites, which fragments comprise a heavy-chain variable domain ($V_H$) connected to a light-chain variable domain ($V_L$) in the same polypeptide chain ($V_H$-$V_L$). By using a linker that is too short to allow pairing between the two domains on the same chain, the domains are forced to pair with the complementary domains of another chain, thereby creating two antigen-binding sites. Diabodies are additionally described, for example, in EP 404,097; WO 93/11161 and Hollinger et al. (1993) Proc. Natl. Acad. Sci. USA 90:6444-6448.

An "isolated" antibody is one that has been identified and separated and/or recovered from a component of its natural environment. Components of its natural environment may include enzymes, hormones, and other proteinaceous or nonproteinaceous solutes. In some embodiments, an isolated antibody is purified (1) to greater than 95% by weight of antibody as determined by the Lowry method, for example, more than 99% by weight, (2) to a degree sufficient to obtain at least 15 residues of N-terminal or internal amino acid sequence, e.g., by use of a spinning cup sequenator, or (3) to homogeneity by gel electrophoresis (e.g., SDS-PAGE) under reducing or nonreducing conditions, with detection by Coomassie blue or silver stain. The term "isolated antibody" includes an antibody in situ within recombinant cells, since at least one component of the antibody's natural environment will not be present. In certain embodiments, isolated antibody is prepared by at least one purification step.

As used herein, "immunoreactive" refers to antibodies or fragments thereof that are specific to a sequence of amino acid residues ("binding site" or "epitope"), yet if are cross-reactive to other peptides/proteins, are not toxic at the levels at which they are formulated for administration to human use. "Epitope" refers to that portion of an antigen capable of forming a binding interaction with an antibody or antigen binding fragment thereof. An epitope can be a linear peptide sequence (i.e., "continuous") or can be composed of non-contiguous amino acid sequences (i.e., "conformational" or "discontinuous"). The term "preferentially binds" means that the binding agent binds to the binding site with greater affinity than it binds unrelated amino acid sequences.

Anti-MMP9 antibodies can be described in terms of the CDRs of the heavy and light chains. As used herein, the term "CDR" or "complementarity determining region" is intended to mean the non-contiguous antigen combining sites found within the variable region of both heavy and light chain polypeptides. These particular regions have been described by Kabat et al., J. Biol. Chem. 252:6609-6616 (1977); Kabat et al., U.S. Dept. of Health and Human Services, "Sequences of proteins of immunological interest" (1991); by Chothia et al., J. Mol. Biol. 196:901-917 (1987); and MacCallum et al., J. Mol. Biol. 262:732-745 (1996), where the definitions include overlapping or subsets of amino acid residues when compared against each other. Nevertheless, application of either definition to refer to a CDR of an antibody or grafted antibodies or variants thereof is intended to be within the scope of the term as defined and used herein. The amino acid residues which encompass the CDRs as defined by each of the above cited references are set forth below in Table 1A as a comparison.

TABLE 1A

| CDR Definitions | | | |
|---|---|---|---|
| | Kabat[1] | Chothia[2] | MacCallum[3] |
| $V_H$ CDR1 | 31-35 | 26-32 | 30-35 |
| $V_H$ CDR2 | 50-65 | 53-55 | 47-58 |
| $V_H$ CDR3 | 95-102 | 96-101 | 93-101 |

TABLE 1A-continued

| CDR Definitions | | | |
|---|---|---|---|
| | Kabat[1] | Chothia[2] | MacCallum[3] |
| $V_L$ CDR1 | 24-34 | 26-32 | 30-36 |
| $V_L$ CDR2 | 50-56 | 50-52 | 46-55 |
| $V_L$ CDR3 | 89-97 | 91-96 | 89-96 |

[1]Residue numbering follows the nomenclature of Kabat et al., supra
[2]Residue numbering follows the nomenclature of Chothia et al., supra
[3]Residue numbering follows the nomenclature of MacCallum et al., supra As used herein, the term "framework" when used in reference to an antibody variable region is intended to mean all amino acid residues outside the CDR regions within the variable region of an antibody. A variable region framework is generally a discontinuous amino acid sequence between about 100-120 amino acids in length but is intended to reference only those amino acids outside of the CDRs. As used herein, the term "framework region" is intended to mean each domain of the framework that is separated by the CDRs.

In some embodiments, an antibody is a humanized antibody or a human antibody. Humanized antibodies include human immununoglobulins (recipient antibody) in which residues from a complementary-determining region (CDR) of the recipient are replaced by residues from a CDR of a non-human species (donor antibody) such as mouse, rat or rabbit having the desired specificity, affinity and capacity. Thus, humanized forms of non-human (e.g., murine) antibodies are chimeric immunoglobulins which contain minimal sequence derived from non-human immunoglobulin. The non-human sequences are located primarily in the variable regions, particularly in the complementarity-determining regions (CDRs). In some embodiments, Fv framework residues of the human immunoglobulin are replaced by corresponding non-human residues. Humanized antibodies can also comprise residues that are found neither in the recipient antibody nor in the imported CDR or framework sequences. In certain embodiments, a humanized antibody comprises substantially all of at least one, and typically two, variable domains, in which all or substantially all of the CDRs correspond to those of a non-human immunoglobulin and all or substantially all of the framework regions are those of a human immunoglobulin consensus sequence. For the purposes of the present disclosure, humanized antibodies can also include immunoglobulin fragments, such as Fv, Fab, Fab', F(ab')$_2$ or other antigen-binding subsequences of antibodies.

The humanized antibody can also comprise at least a portion of an immunoglobulin constant region (Fc), typically that of a human immunoglobulin. See, for example, Jones et al. (1986) Nature 321:522-525; Riechmann et al. (1988) Nature 332:323-329; and Presta (1992) Curr. Op. Struct. Biol. 2:593-596.

Methods for humanizing non-human antibodies are known in the art. Generally, a humanized antibody has one or more amino acid residues introduced into it from a source that is non-human. These non-human amino acid residues are often referred to as "import" or "donor" residues, which are typically obtained from an "import" or "donor" variable domain. For example, humanization can be performed essentially according to the method of Winter and co-workers, by substituting rodent CDRs or CDR sequences for the corresponding sequences of a human antibody. See, for example, Jones et al., supra; Riechmann et al., supra and Verhoeyen et al. (1988) Science 239:1534-1536. Accordingly, such "humanized" antibodies include chimeric antibodies (U.S. Pat. No. 4,816,567), wherein substantially less than an intact human variable domain has been substituted by the corresponding sequence from a non-human species. In certain embodiments, humanized antibodies are human antibodies in which some CDR residues and optionally some framework region residues are substituted by residues from analogous sites in rodent antibodies (e.g., murine monoclonal antibodies).

Human antibodies can also be produced, for example, by using phage display libraries. Hoogenboom et al. (1991) *J. Mol. Biol,* 227:381; Marks et al. (1991) *J. Mol. Biol.* 222:581. Other methods for preparing human monoclonal antibodies are described by Cole et al. (1985) "Monoclonal Antibodies and Cancer Therapy," Alan R. Liss, p. 77 and Boerner et al. (1991) *J. Immunol.* 147:86-95.

Human antibodies can be made by introducing human immunoglobulin loci into transgenic animals (e.g., mice) in which the endogenous immunoglobulin genes have been partially or completely inactivated. Upon immunological challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al. (1992) *Bio/Technology* 10:779-783 (1992); Lonberg et al. (1994) *Nature* 368: 856-859; Morrison (1994) *Nature* 368:812-813; Fishwald et al. (1996) *Nature Biotechnology* 14:845-851; Neuberger (1996) *Nature Biotechnology* 14:826; and Lonberg et al. (1995) *Intern. Rev. Immunol.* 13:65-93.

Antibodies can be affinity matured using known selection and/or mutagenesis methods as described above. In some embodiments, affinity matured antibodies have an affinity which is five times or more, ten times or more, twenty times or more, or thirty times or more than that of the starting antibody (generally murine, rabbit, chicken, humanized or human) from which the matured antibody is prepared.

An antibody can also be a bispecific antibody. Bispecific antibodies are monoclonal, and may be human or humanized antibodies that have binding specificities for at least two different antigens. In the present case, the two different binding specificities can be directed to two different MMPs, or to two different epitopes on a single MMP (e.g., MMP9).

An antibody as disclosed herein can also be an immunoconjugate. Such immunoconjugates comprise an antibody (e.g., to MMP9) conjugated to a second molecule, such as a reporter An immunoconjugate can also comprise an antibody conjugated to a cytotoxic agent such as a chemotherapeutic agent, a toxin (e.g., an enzymatically active toxin of bacterial, fungal, plant, or animal origin, or fragments thereof), or a radioactive isotope (i.e., a radioconjugate).

An antibody that "specifically binds to" or is "specific for" a particular polypeptide or an epitope refers to the selective binding of the antibody to the target antigen or epitope; these terms, and methods for determining specific binding, are well understood in the art. An antibody exhibits "specific binding" for a particular target antigen or epitope if it binds with greater affinity, avidity, more readily, and/or with greater duration to that target antigen or epitope than it does with other substances. In some embodiments, the antibody that specifically binds to the polypeptide or epitope is one that binds to that particular polypeptide or epitope without substantially binding to any other polypeptide or polypeptide epitope. In some embodiments, the provided antibodies specifically bind to human MMP9 with a dissociation constant ($K_d$) equal to or lower than 100 nM, optionally lower than 10 nM, optionally lower than 1 nM, optionally lower than 0.5 nM, optionally lower than 0.1 nM, optionally lower than 0.01 nM, or optionally lower than 0.005 nM, in certain examples, between 0.1 and 0.2 nM, or between 0.1 and 10 pM, e.g., between 0.4 and 9 pm, such as between 0.4 and 8.8 pm, in the form of monoclonal antibody, scFv, Fab, or other form of antibody measured at a temperature of about 4° C., 25° C., 37° C. or 42° C.

In certain embodiments, an antibody of the present disclosure binds to one or more processing sites (e.g., sites of proteolytic cleavage) in MMP9, thereby effectively blocking processing of the proenzyme or preproenzyme to the catalytically active enzyme, and thus reducing the proteolytic activity of the MMP9.

In certain embodiments, an antibody according to the present disclosure binds to MMP9 with an affinity at least 2 times, at least 5 times, at least 10 times, at least 25 times, at least 50 times, at least 100 times, at least 500 times, or at least 1000 times greater than its binding affinity for another MMP. Binding affinity can be measured by any method known in the art and can be expressed as, for example, on-rate, off-rate, dissociation constant ($K_d$), equilibrium constant ($K_{eq}$) or any term in the art.

In certain embodiments, an antibody according to the present disclosure is one that inhibits the enzymatic (i.e., catalytic) activity of MMP9, such as a non-competitive inhibitor of the catalytic activity of MMP9. In certain embodiments, an antibody according to the present disclosure binds within the catalytic domain of MMP9. In additional embodiments, an antibody according to the present disclosure binds outside the catalytic domain of MMP9.

Also provided are antibodies or antigen binding fragments thereof that compete with any one or more of the anti-MMP9 antibodies or antigen binding fragments thereof described herein for binding to MMP9. Thus, the present disclosure contemplates anti-MMP9 antibodies, and functional fragments thereof, that compete for binding with, for example, an antibody having a heavy chain polypeptide of any of SEQ ID NOS: 1 or 5-8, a light chain polypeptide of SEQ ID NOS: 2 or 9-12, or combinations thereof. In one embodiment, the anti-MMP9 antibody, or functional fragment thereof, competes for binding to human MMP9 with the antibody described herein as AB0041.

Also provided are antibodies and fragments thereof that bind to the same epitope, e.g., MMP9 epitope as any one or more of the antibodies described herein. Also provided are antibodies and fragments that specifically bind to an epitope of MMP9, where the epitope includes an amino acid residue within a particular region of MMP9 or multiple regions of MMP9. Such regions can include, for example, structural loops and/or other structural domains of MMP9, such as those shown to be important for binding to exemplary antibodies described herein. Typically, the regions are defined according to amino acid residue positions on the full-length MMP9 sequence, e.g., SEQ ID NO: 27. In some example, the epitope contains an amino acid residue 104-202 of SEQ ID NO: 27. In one example, the epitope contains an amino acid residue (i.e., one or more amino acid residue(s)) within a region that is residues 104-119 residues 159-166, or residues 191-202 of SEQ ID NO: 27. In some aspects, the epitope includes an amino acid residue (i.e., one or more amino acid residue(s)) within a region of MMP9 that is residues 104-119 of SEQ ID NO: 27, an amino acid residue within a region of MMP9 that is residues 159-166 of SEQ ID NO: 27, and an amino acid residue within a region of MMP9 that is residues 191-202 of SEQ ID NO: 27. In some cases, the epitope includes E111, D113, R162, or I198 of SEQ ID NO: 27. In some cases, it includes R162 of SEQ ID NO: 27. In some cases, it includes E111, D113, R162, and I198 of SEQ ID NO: 27.

MMP9 Sequence

The amino acid sequence of human MMP9 protein is as follows:

```
                                              (SEQ ID NO: 27)
MSLWQPLVLV LLVLGCCFAA PRQRQSTLVL FPGDLRTNLT        50
DRQLAEEYLY

RYGYTRVAEM RGESKSLGPA LLLLQKQLSL PETGELDSAT       100
LKAMRTPRCG

VPDLGRFQTF EGDLKWHHHN ITYWIQNYSE DLPRAVIDDA       150
FARAFALWSA

VTPLTFTRVY SRDADIVIQF GVAEHGDGYP FDGKDGLLAH       200
AFPPGPGIQG

DAHFDDDELW SLGKGVVVPT RFGNADGAAC HFPFIFEGRS       250
YSACTTDGRS

DGLPWCSTTA NYDTDDRFGF CPSERLYTRD GNADGKPCQF       300
PFIFQGQSYS

ACTTDGRSDG YRWCATTANY DRDKLFGFCP TRADSTVMGG       350
NSAGELCVFP

FTFLGKEYST CTSEGRGDGR LWCATTSNFD SDKKWGFCPD       400
QGYSLFLVAA

HEFGHALGLD HSSVPEALMY PMYRFTEGPP LHKDDVNGIR       450
HLYGPRPEPE

PRPPTTTTPQ PTAPPTVCPT GPPTVHPSER PTAGPTGPPS       500
AGPTGPPTAG

PSTATTVPLS PVDDACNVNI FDAIAEIGNQ LYLFKDGKYW       550
RFSEGRGSRP

QGPFLIADKW PALPRKLDSV FEEPLSKKLF FFSGRQVWVY       600
TGASVLGPRR

LDKLGLGADV AQVTGALRSG RGKMLLFSGR RLWRFDVKAQ       650
MVDPRSASEV

DRMFPGVPLD THDVFQYREK AYFCQDRFYW RVSSRSELNQ       700
VDQVGYVTYD

ILQCPED
```

Protein domains are shown schematically in FIG. 3 and are indicated below:

| Amino Acid # | Feature |
|---|---|
| 1-19 | Signal Peptide |
| 38-98 | Peptidoglycan Binding Domain |
| R98/C99 | Cysteine-switch active pocket |
| 112-445 | Zn dependent metalloproteinase domain |
| 223-271 | Fibronectin type II domain (gelatin binding domain) |
| 281-329 | Fibronectin type II domain (gelatin binding domain) |
| 340-388 | Fibronectin type II domain (gelatin binding domain) |
| 400-411 | Zn binding region |
| 521-565 | Hemopexin-like domain |
| 567-608 | Hemopexin-like domain |
| 613-659 | Hemopexin-like domain |
| 661-704 | Hemopexin-like domain |

The amino acid sequence of mature full-length human MMP9 (which is the amino acid sequence of the propolypeptide of SEQ ID NO:27 without the signal peptide) is:

```
                                              (SEQ ID NO: 28)
APRQRQSTLVL FPGDLRTNLT DRQLAEEYLY RYGYTRVAEM

RGESKSLGPA LLLLQKQLSL PETGELDSAT LKAMRTPRCG

VPDLGRFQTF EGDLKWHHHN ITYWIQNYSE DLPRAVIDDA

FARAFALWSA VTPLTFTRVY SRDADIVIQF GVAEHGDGYP

FDGKDGLLAH AFPPGPGIQG DAHFDDDELW SLGKGVVVPT

RFGNADGAAC HFPFIFEGRS YSACTTDGRS DGLPWCSTTA

NYDTDDRFGF CPSERLYTRD GNADGKPCQF PFIFQGQSYS

ACTTDGRSDG YRWCATTANY DRDKLFGFCP TRADSTVMGG

NSAGELCVFP FTFLGKEYST CTSEGRGDGR LWCATTSNFD

SDKKWGFCPD QGYSLFLVAA HEFGHALGLD HSSVPEALMY

PMYRFTEGPP LHKDDVNGIR HLYGPRPEPE PRPPTTTTPQ

PTAPPTVCPT GPPTVHPSER PTAGPTGPPS AGPTGPPTAG

PSTATTVPLS PVDDACNVNI FDAIAEIGNQ LYLFKDGKYW

RFSEGRGSRP QGPFLIADKW PALPRKLDSV FEEPLSKKLF

FFSGRQVWVY TGASVLGPRR LDKLGLGADV AQVTGALRSG

RGKMLLFSGR RLWRFDVKAQ MVDPRSASEV DRMFPGVPLD

THDVFQYREK AYFCQDRFYW RVSSRSELNQ VDQVGYVTYD

ILQCPED
```

The amino acid sequence of the signal peptide is MSLWQPLVLVLLVLGCCFA (SEQ ID NO:29).

Also provided are MMP9 polypeptides, including mutant MMP9 polypeptides. Such peptides are useful, for example, in generating and selecting antibodies and fragments as provided herein. Exemplary polypeptides include those having an amino acid sequence containing residues 111-198 of SEQ ID NO: 27, and those having an amino acid sequence containing residues 111-198 of SEQ ID NO: 27 with an amino acid substitution at residue 111, 113, 162, or 198 of SEQ ID NO 27 or with an amino acid substitution at all such residues. Such polypeptides find use, for example, in selecting antibodies that bind to epitopes containing such residues and/or for which such residues of MMP9 are important for binding, such as those described herein.

The present disclosure contemplates MMP9 binding proteins that bind any portion of MMP9, e.g., human MMP9, with MMP9 binding proteins that preferentially bind MMP9 relative to other MMPs being of particular interest.

Anti-MMP9 antibodies, and functional fragments thereof, can be generated accordingly to methods well known in the art. Exemplary anti-MMP9 antibodies are provided below.

Mouse Monoclonal Anti-MMP9 Antibodies

A mouse monoclonal antibody to human MMP9 was obtained as. This antibody contains a mouse IgG2b heavy chain and a mouse kappa light chain, and is denoted AB0041.

The amino acid sequence of the AB0041 heavy chain is as follows:

(SEQ ID NO: 1)
```
MAVLVLFLCLVAFPSCVLSQVQLKESGPGLVAPSQSLSITCTVSGFSLLSYGVHW
VRQPPGKGLEWLGVIWTGGTTNYNSALMSRLSISKDDSKSQVFLKMNSLQTDDTAIYY
CARYYYGMDYWGQGTSVTVSSAKTTPPSVYPLAPGCGDTTGSSVTLGCLVKGYFPESVTVT
WNSGSLSSSVHTFPALLQSGLYTMSSSVTVPSSTWPSQTVTCSVAHPASSTTVDKKLEPSGPISTI
NPCPPCKECHKCPAPNLEGGPSVFIFPPNIKDVLMISLTPKVTCVVVDVSEDDPDVRISWFVN
NVEVHTAQTQTHREDYNSTIRVVSALPIQHQDWMSGKEFKCKVNNKDLPSPIERTISKIKGLV
RAPQVYILPPPAEQLSRKDVSLTCLVVGFNPGDISVEWTSNGHTEENYKDTAPVLDSDGSYFIY
SKLDIKTSKWEKTDSFSCNVRHEGLKNYYLKKTISRSPGK
```

The signal sequence is underlined, and the sequence of the IgG2b constant region is presented italics.

The amino acid sequence of the AB0041 light chain is as follows:

(SEQ ID NO: 2)
```
MESQIQVFVFVFLWLSGVDGDIVMTQSHKFMSTSVGDRVSITCKASQDVRNTVA
WYQQKTGQSPKLLIYSSSYRNTGVPDRFTGSGSGTDFTFTISSVQAEDLAVYFCQQHYIT
PYTFGGGTKLEIKRADAAPTVSIFPPSSEQLTSGGASVVCFLNNFYPKDINVKWKIDGSERQN
GVLNSWTDQDSKDSTYSMSSTLTLTKDEYERHNSYTCEATHKTSTSPIVKSFNRNEC
```

The signal sequence is underlined, and the sequence of the kappa constant region is presented in italics.

The following amino acid sequence comprises the framework regions and complementarity-determining regions (CDRs) of the variable region of the IgG2b heavy chain of AB0041 (with CDRs underlined):

(SEQ ID NO: 3)
```
QVQLKESGPGLVAPSQSLSITCTVSGFSLLSYGVHWVRQPPGKGLEWLGV
IWTGGTTNYNSALMSRLSISKDDSKSQVFLKMNSLQTDDTAIYYCARYYY
GMDYWGQGTSVTVSS
```

The following amino acid sequence comprises the framework regions and complementarity-determining regions (CDRs) of the variable region of the kappa light chain of AB0041 (with CDRs underlined):

(SEQ ID NO: 4)
```
DIVMTQSHKFMSTSVGDRVSITCKASQDVRNTVAWYQQKTGQSPKLLIYS
SSYRNTGVPDRFTGSGSGTDFTFTISSVQAEDLAVYFCQQHYITPYTFGG
GTKLEIK
```

Other exemplary mouse anti-human MMP9 antibodies (e.g., M4 and M12) are described herein. An exemplary anti-mouse MMP9 antibody (AB0046) is described herein. In some embodiments, provided are uses of such anti-mouse antibodies as surrogate antibodies for testing and assessing the MMP9-inhibition methods, e.g., therapeutic methods, as provided herein.

Heavy-Chain Variants

The amino acid sequences of the variable regions of the AB0041 heavy and light chains were separately modified, by altering framework region sequences in the heavy and light chain variable regions. The effect of these sequence alterations was to deplete the antibody of human T-cell epitopes, thereby reducing or abolishing its immunogenicity in humans (Antitope, Babraham, UK).

Four heavy-chain variants were constructed, in a human IgG4 heavy chain background containing a S241P amino acid change that stabilizes the hinge domain (Angal et al. (1993) *Molec. Immunol.* 30:105-108), and are denoted VH1, VH2, VH3 and VH4. The amino acid sequences of their framework regions and CDRs are as follows:

VH1
(SEQ ID NO: 5)
```
QVQLQESGPGLVKPSETLSLTCTVSGFSLLSYGVHWVRQPPGKGLE
WLGVIWTGGTTNYNSALMSRLTISKDDSKSTVYLKMNSLKTEDTAIYYCA
RYYYGMDYWGQGTSVTVSS
```

VH2
(SEQ ID NO: 6)
```
QVQLQESGPGLVKPSETLSLTCTVSGFSLLSYGVHWVRQPPGKGLE
WLGVIWTGGTTNYNSALMSRLTISKDDSKNTVYLKMNSLKTEDTAIYYCA
RYYYGMDYWGQGTLVTVSS
```

VH3
(SEQ ID NO: 7)
```
QVQLQESGPGLVKPSETLSLTCTVSGFSLLSYGVHWVRQPPGKGLE
WLGVIWTGGTTNYNSALMSRFTISKDDSKNTVYLKMNSLKTEDTAIYYCA
RYYYGMDYWGQGTLVTVSS
```

VH4
(SEQ ID NO: 8)
```
QVQLQESGPGLVKPSETLSLTCTVSGFSLLSYGVHWVRQPPGKGLE
WLGVIWTGGTTNYNSALMSRFTISKDDSKNTLYLKMNSLKTEDTAIYYCA
RYYYGMDYWGQGTLVTVSS
```

FIG. 1 shows an alignment of the amino acid sequences of the variable regions of the humanized heavy chains and indicates the differences in amino acid sequences in the framework regions among the four variants.

Light-Chain Variants

Four light-chain variants were constructed, in a human kappa chain background, and are denoted Vk1, Vk2, Vk3 and Vk4. The amino acid sequences of their framework regions and CDRs are as follows:

Vk1
(SEQ ID NO: 9)
DIVMTQSPSFLSASVGDRVTITCKASQDVRNTVAWYQQKTGKAPKL

LIYSSSYRNTGVPDRFTGSGSGTDFTLTISSLQAEDVAVYFCQQHYITPY

TFGGGTKVEIK

Vk2
(SEQ ID NO: 10)
DIVMTQSPSSLSASVGDRVTITCKASQDVRNTVAWYQQKPGKAPKL

LIYSSSYRNTGVPDRFTGSGSGTDFTLTISSLQAEDVAVYFCQQHYITPY

TFGGGTKVEIK

Vk3
(SEQ ID NO: 11)
DIQMTQSPSSLSASVGDRVTITCKASQDVRNTVAWYQQKPGKAPKL

LIYSSSYRNTGVPDRFSGSGSGTDFTLTISSLQAEDVAVYFCQQHYITPY

TFGGGTKVEIK

Vk4
(SEQ ID NO: 12)
DIQMTQSPSSLSASVGDRVTITCKASQDVRNTVAWYQQKPGKAPKL

LIYSSSYRNTGVPDRFSGSGSGTDFTLTISSLQAEDVAVYYCQQHYITPY

TFGGGTKVEIK

FIG. 2 shows an alignment of the amino acid sequences of the variable regions of the humanized light chains and indicates the differences in amino acid sequences in the framework regions among the four variants.

The humanized heavy and light chains are combined in all possible pair-wise combinations to generate a number of functional humanized anti-MMP9 antibodies. For example, provided are antibodies with a heavy chain variable (VH) region having the amino acid sequence set forth in any of SEQ ID NOs: 3, 5, 6, 7, and 8; antibodies having a light chain variable (VL) region having the amino acid sequence set forth in any of SEQ ID NOs: 4, 9, 10, 11, and 12; and antibodies with a heavy chain variable (VH) region having the amino acid sequence set forth in any of SEQ ID NOs: 3, 5, 6, 7, and 8 and a light chain variable (VL) region having the amino acid sequence set forth in any of SEQ ID NOs: 4, 9, 10, 11, and 12, as well as antibodies that compete for binding to MMP9 with such antibodies and antibodies having at least at or about 75%, 80%, 85%, 90%, 91%, 92%, 93%, 94%, 95%, 96%, 97%, 98%, 99% or more sequence identity with such antibodies. In one example, the antibody has a VH region with an amino acid sequence having at least at or about 75%, 80%, 85%, 90%, 91%, 92%, 93%, 94%, 95%, 96%, 97%, 98%, 99% or more sequence identity with SEQ ID NO: 7 and a VL region with an amino acid sequence having at least at or about 75%, 80%, 85%, 90%, 91%, 92%, 93%, 94%, 95%, 96%, 97%, 98%, 99% or more sequence identity with SEQ ID NO: 12, or a VH region of SEQ ID NO: 7 and a VL region of SEQ ID NO: 12.

Additional heavy chain variable region amino acid sequences having 75% or more, 80% or more, 90% or more, 95% or more, or 99% or more homology to the heavy chain variable region sequences disclosed herein are also provided. Furthermore, additional light chain variable region amino acid sequences having 75% or more, 80% or more, 90% or more, 95% or more, or 99% or more homology to the light chain variable region sequences disclosed herein are also provided.

Additional heavy chain variable region amino acid sequences having 75% or more, 80% or more, 90% or more, 95% or more, or 99% or more sequence identity to the heavy chain variable region sequences disclosed herein are also provided. Furthermore, additional light chain variable region amino acid sequences having 75% or more, 80% or more, 90% or more, 95% or more, or 99% or more sequence identity to the light chain variable region sequences disclosed herein are also provided.

Complementarity-Determining Regions (CDRs)

In some embodiments, the CDRs of the heavy chain of exemplary provided anti-MMP9 antibodies as disclosed herein have the following amino acid sequences:

| CDR1: | GFSLLSYGVH | (SEQ ID NO: 13) |
| CDR2: | VIWTGGTTNYNSALMS | (SEQ ID NO: 14) |
| CDR3: | YYYGMDY | (SEQ ID NO: 15) |

Thus, among the provided anti-MMP9 antibodies are antibodies having a heavy chain CDR1 region with an amino acid sequence as set forth in SEQ ID NO: 13, antibodies having a heavy chain CDR2 region with an amino acid sequence set forth in SEQ ID NO: 14, and antibodies having a heavy chain CDR3 region with an amino acid sequence as set forth in SEQ ID NO: 15, and antibodies that compete for binding with or bind to the same epitope on MMP9 as such antibodies. In some cases, the antibodies contain VH CDRs having the sequences set forth in SEQ ID NO: 15. In some cases, the antibodies contain VH CDRs having the sequences set forth in SEQ ID NOs: 13 and 14. In some cases, the antibodies contain VH CDRs having the sequences set forth in SEQ ID NOs: 13 and 15. In some cases, the antibodies contain VH CDRs having the sequences set forth in SEQ ID NOs: 14 and 15. In some cases, the antibodies contain VH CDRs having the sequences set forth in SEQ ID NOs: 13, 14, and 15.

In some embodiments, the CDRs of the light chain of exemplary anti-MMP9 antibodies as disclosed herein have the following amino acid sequences:

| CDR1: | KASQDVRNTVA | (SEQ ID NO: 16) |
| CDR2: | SSSYRNT | (SEQ ID NO: 17) |
| CDR3: | QQHYITPYT | (SEQ ID NO: 18) |

Thus, among the provided anti-MMP9 antibodies are antibodies having a light chain CDR1 region with an amino acid sequence as set forth in SEQ ID NO: 16, antibodies having a light chain CDR2 region with an amino acid sequence set forth in SEQ ID NO: 17, and antibodies having a light chain CDR3 region with an amino acid sequence as set forth in SEQ ID NO: 18, and antibodies that compete for binding with or bind to the same epitope on MMP9 as such antibodies. In some cases, the antibodies contain VL CDRs having the sequences set forth in SEQ ID NO: 18. In some cases, the antibodies contain VL CDRs having the sequences set forth in SEQ ID NOs: 16 and 17. In some cases, the antibodies contain VL CDRs having the sequences set forth in SEQ ID NOs: 16 and 18. In some cases, the antibodies contain VL CDRs having the sequences set forth in SEQ ID NOs: 17 and 18. In some cases, the antibodies contain VL CDRs having the sequences set forth in SEQ ID NOs: 16, 17, and 18.

An exemplary humanized variant anti-MMP9 antibody, AB0045 (humanized, modified IgG4 (S241P)) contains the humanized AB0041 heavy chain variant VH3 (having the sequence set forth in SEQ ID NO: 7

(QVQLQESGPGLVKPSETLSLTCTVSGFSLLSYGVHWVRQPPGKGLEWLGVIVVTGGTTN

YNSALMSRFTISKDDSKNTVYLKMNSLKTEDTAIYYCARYYYGMDYWGQGTLVTVSS)

and the humanized AB0041 light chain variant VH4 (having the light chain sequence set forth in Vk4 (having the sequence set forth in SEQ ID NO: 12

(DIQMTQSPSSLSASVGDRVTITCKASQDVRNTVAWYQQKPGKAPKLLIYSSSYRNTGVP

DRFSGSGSGTDFTLTISSLQAEDVAVYYCQQHYITPYTFGGGTKVEIK)).

The AB0045 antibody contains 1312 amino acids in length, is composed of two heavy chains and two light chains, and has a theoretical pI of about 7.90, extinction coefficient of about 1.50 AU/cm at 280 nm for 1 g/L, a molecular weight of about 144 kDa, and density of about 1 g/mL in formulation buffer (50-100 mg/mL product concentration).

The heavy chain of the AB0045 antibody has the sequence set forth in SEQ ID NO: 49

(MGWSLILLFLVAVATRVHSQVQLQESGPGLVKPSETLSLTCTVSGFSLLSYGVHWVRQ

PPGKGLEWLGVIWTGGTTNYNSALMSRFTISKDDSKNTVYLKMNSLKTEDTAIYYCAR

YYYGMDYWGQGTLVTVSSASTKGPSVFPLAPCSRSTSESTAALGCLVKDYFPEPVTVSWNS

GALTSGVHTFPAVLQSSGLYSLSSVVTVPSSSLGTKTYTCNVDHKPSNTKVDKRVESKYGPPCP

PCPAPEFLGGPSVFLFPPKPKDTLMISRTPEVTCVVVDVSQEDPEVQFNWYVDGVEVHNAKT

KPREEQFNSTYRVVSVLTVLHQDWLNGKEYKCKVSNKGLPSSIEKTISKAKGQPREPQVYTLP

PSQEEMTKNQVSLTCLVKGFYPSDIAVEWESNGQPENNYKTTPPVLDSDGSFFLYSRLTVDKS

RWQEGNVFSCSVMHEALHNHYTQKSLSLSLGK (signal sequence underlined; sequence of the constant region presented italics)); the light chain of the AB0045 antibody has the sequence set forth in SEQ ID NO: 50

(MRVPAQLLGLLLLWLPGARCDIQMTQSPSSLSASVGDRVTITCKASQDVRNTVAWYQ

QKPGKAPKLLIYSSSYRNTGVPDRFSGSGSGTDFTLTISSLQAEDVAVYYCQQHYITPYT

FGGGTKVEIKRTVAAPSVFIFPPSDEQLKSGTASVVCLLNNFYPREAKVQWKVDNALQSGNS

QESVTEQDSKDSTYSLSSTLTLSKADYEKHKVYACEVTHQGLSSPVTKSFNRGEC (signal sequence underlined; sequence of the constant region presented italics).

The antibodies further include those produced by the hybridoma designated M4, i.e., an antibody containing the heavy chain (IgG2b) sequence:

(SEQ ID NO: 30)
MAVLVLFLCLVAFPSCVLSQVQLKESGPGLVAPSQSLSITCTVSGFSLLSYGVHWVRQPP

GKGLEWLGVIWTGGSTNYNSALMSRLSISKDDSKSQVFLKMNSLQTDDTAMYYCARY

YYAMDYWGQGTSVTVSSAKTTPPSVYPLAPGCGDTTGSSVTLGCLVKGYFPESVTVTWNSG

SLSSSVHTFPALLQSGLYTMSSSVTVPSSTWPSQTVTCSVAHPASSTTVDKKLEPSGPISTINPCP

PCKECHKCPAPNLEGGPSVFIFPPNIKDVLMISLTPKVTCVVVDVSEDDPDVRISWFVNNVEV

HTAQTQTHREDYNSTIRVVSALPIQHQDWMSGKEFKCKVNNKDLPSPIERTISKIKGLVRAPQ

VYILPPPAEQLSRKDVSLTCLVVGFNPGDISVEWTSNGHTEENYKDTAPVLDSDGSYFIYSKLD

IKTSKWEKTDSFSCNVRHEGLKNYYLKKTISRSPGK (signal peptide set forth in underlined text, variable region set forth in plain text, and constant region set forth in italics), and the light chain (kappa) sequence:

MESQIQVFVFVFLWLSGVDGDIVMTQSHKFMFTSVGDRVSITCKASQDVRNTVAWYQQ

KTGQSPKLLIYSASYRNTGVPDRFTGSISGTDFTFTISSVQAEDLALYYCQQHYSTPYTFG

GGTKLEVKRADAAPTVSIFPPSSEQLTSGGASVVCFLNNFYPKDINVKWKIDGSERQNGVLNS

WTDQDSKDSTYSMSSTLTLTKDEYERHNSYTCEATHKTSTSPIVKSFNRNEC (signal peptide set forth in underlined text, variable region set forth in plain text, and constant region set forth in italics) (SEQ ID NO: 31). The M4 antibody has a variable heavy chain with an amino acid sequence:

QVQLKESGPGLVAPSQSLSITCTVSGFSLLSYGVHWVRQPPGKGLEWLGVIWTGGSTNY

NSALMSRLSISKDDSKSQVFLKMNSLQTDDTAMYYCARYYYAMDYWGQGTSVTVSS (CDRs 1, 2, and 3 (SEQ ID NOs: 34, 35, and 36, respectively) underlined) (SEQ ID NO: 32) and a variable light chain with the amino acid sequence

DIVMTQSHKFMFTSVGDRVSITCKASQDVRNTVAWYQQKTGQSPKLLIY

SASYRNTGVPDRFTGSISGTDFTFTISSVQAEDLALYYCQQHYSTPYT

FGGGTKLEVK (CDRs 1, 2, and 3 (SEQ ID NOs: 37, 38, and 39, respectively) underlined) (SEQ ID NO: 33).

The antibodies further include those produced by the hybridoma designated M12, i.e., one with only a kappa chain, having the sequence:

QVFVYMLLWLSGVDGDIVMTQSQKFMSTSVGDRVSVTCKASQNVGTNVAWYQQKPG

QSPKALIYSASYRFSGVPDRFTGSGSGTDFTLTISNVQSEDLAEYFCQQYNSYPYTFGGG

TKLEIKRADAAPTVSIFPPSSEQLTSGGASVVCFLNNFYPKDINVKWKIDGSERQNGVLNSWT

DQDSKDSTYSMSSTLTLTKDEYERHNSYTCEATHKTSTSPIVKSFNRNEC (signal peptide set forth in underlined text, variable region set forth in plain text, and constant region set forth in italics) (SEQ ID NO: 40). The M12 antibody has a variable light chain with the amino acid sequence

DIVMTQSQKFMSTSVGDRVSVTCKASQNVGTNVAWYQQKPGQSPKALIY

SASYRFSGVPDRFTGSGSGTDFTLTISNVQSEDLAEYFCQQYNSYPYTF

GGGTKLEIK (CDRs 1, 2, and 3 (SEQ ID NOs: 42, 43, and 44, respectively) underlined) (SEQ ID NO: 41).

The antibodies further include the mouse antibody designated AB0046, having a kappa light chain with an amino acid sequence (SEQ ID NO: 45)
MSSAQFLGLLLLCFQGTRCDIQMTQTTSSLSASLGDRVTISCSASQGISNYLNWYQQKPD

GTFKLLIYYTSILHSGVPSRFSGSGSGTDYSLTISNLEPEDIATYYCQQYGWLPRTFGGGT

KLEIKRADAAPTVSIFPPSSEQLTSGGASVVCFLNNFYPKDINVKWKIDGSERQNGVLNSWTD

QDSKDSTYSMSSTLTLTKDEYERHNSYTCEATHKTSTSPIVKSFNRNEC (signal peptide set forth in underlined text, variable region set forth in plain text, and constant region set forth in italics) and an IgG 1 heavy chain with an amino acid sequence (SEQ ID NO: 46)
MGWSSIILFLVATATGVHSQVQLQQPGSVLVRPGASVKLSCTASGYTFTSYWMNWVKQ

RPGQGLEWIGEIYPISGRTNYNEKFKVKATLTVDTSSSTAYMDLNSLTSEDSAVYYCARS

RANWDDYWGQGTTLTVSS*AKTTPPSVYPLAPGSAAQTNSMVTLGCLVKGYFPEPVTVTWN*

*SGSLSSGVHTFPAVLQSDLYTLSSSVTVPSSTWPSETVTCNVAHPASSTKVDKKIVPRDCGCKP*

*CICTVPEVSSVFIFPPKPKDVLTITLTPKVTCVVVDISKDDPEVQFSWFVDDVEVHTAQTQPRE*

*EQFNSTFRSVSELPIMHQDWLNGKEFKCRVNSAAFPAPIEKTISKTKGRPKAPQVYTIPPPKEQ*

*MAKDKVSLTCMITDFFPEDITVEWQWNGQPAENYKNTQPIMDTDGSYFVYSKLNVQKSNWE*

*AGNTFTCSVLHEGLHNHHTEKSLSHSPGK*

(signal peptide set forth in underlined text, variable region set forth in plain text, and constant region set forth in italics).

The following amino acid sequence comprises the framework regions and complementarity-determining regions (CDRs) of the variable region of the IgG1 heavy chain of AB0046 (with CDRs underlined):

(SEQ ID No: 47)
QVQLQQPGSVLVRPGASVKLSCTAS<u>GYTFTSYWMN</u>WVKQRPGQGLEWI

<u>GEIYPISGRTNYNEKFKV</u>KATLTVDTSSSTAYMDLNSLTSEDSAVYYCA

R<u>SRANWDDY</u>WGQGTTLTVSS.

The following amino acid sequence comprises the framework regions and complementarity-determining regions (CDRs) of the variable region of the kappa light chain of AB0046 (with CDRs underlined):

(SEQ ID No: 48)
DIQMTQTTSSLSASLGDRVTISC<u>SASQGISNYLN</u>WYQQKPDGTFKLLIY

YT<u>SILHS</u>GVPSRFSGSGSGTDYSLTISNLEPEDIATYYC<u>QQYGWLPRTF</u>

GGGTKLEIK.

The antibodies for use with the presently provided methods, compositions, and combinations can include any of the antibodies described herein, including antibodies and antibody fragments, including those containing any combination of the various exemplified heavy and light chains, heavy and light chain variable regions, and CDRs.

Nucleic Acids Encoding Anti-MMP9 Antibodies

The present disclosure provides nucleic acids encoding anti-MMP9 antibodies and functional fragments thereof. Accordingly, the present disclosure provides an isolated polynucleotide (nucleic acid) encoding an antibody or antigen-binding fragment as described herein, vectors containing such polynucleotides, and host cells and expression systems for transcribing and translating such polynucleotides into polypeptides.

The present disclosure also contemplates constructs in the form of plasmids, vectors, transcription or expression cassettes which comprise at least one polynucleotide as above.

The present disclosure also provides a recombinant host cell which comprises one or more constructs as above, as well as methods of production of the antibody or antigen-binding fragments thereof described herein which method comprises expression of nucleic acid encoding a heavy chain polypeptide and a light chain polypeptide (in the same or different host cells, and from the same or different constructs) in a recombination host cell. Expression can be achieved by culturing under appropriate conditions recombinant host cells containing the nucleic acid. Following production by expression, an antibody or antigen-binding fragment can be isolated and/or purified using any suitable technique, then used as appropriate.

Systems for cloning and expression of a polypeptide in a variety of different host cells are well known. Suitable host cells include bacteria, mammalian cells, yeast and baculovirus systems. Mammalian cell lines available in the art for expression of a heterologous polypeptide include Chinese hamster ovary cells, HeLa cells, baby hamster kidney cells, NSO mouse melanoma cells and many others. A common bacterial host is *E. coli*.

Suitable vectors can be chosen or constructed, containing appropriate regulatory sequences, including operably linked promoter sequences, terminator sequences, polyadenylation sequences, enhancer sequences, marker genes and/or other sequences as appropriate. Vectors can be plasmids, viral e.g. 'phage, or phagemid, as appropriate. For further details see, for example, Molecular Cloning: a Laboratory Manual: 2nd edition, Sambrook et al., 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in Short Protocols in Molecular Biology, Second Edition, Ausubel et al. eds., John Wiley & Sons, 1992. The disclosures of Sambrook et al. and Ausubel et al. are incorporated herein by reference in their entirety.

The nucleic acid encoding a polypeptide of interest is integrated into the genome of the host cell or can be maintained as a stable or transient episomal element.

Any of a wide variety of expression control sequences—sequences that control the expression of a DNA sequence operatively linked to it—can be used in these vectors to express the DNA sequences. For example, a nucleic acid encoding a polypeptide of interest can be operably linked to a promoter, and provided in an expression construct for use in methods of production of recombinant MMP9 proteins or portions thereof.

Those of skill in the art are aware that nucleic acids encoding the antibody chains disclosed herein can be synthesized using standard knowledge and procedures in molecular biology.

Examples of nucleotide sequences encoding the heavy and light chain amino acid sequences disclosed herein, are as follows:

(SEQ ID NO: 19)
VH1: CAGGTGCAGC TGCAGGAATC CGGCCCTGGC CTGGTCAAGC

CCTCCGAGAC ACTGTCCCTG ACCTGCACCG TGTCCGGCTT CTCCCTGCTG

TCCTACGGCG TGCACTGGGT CCGACAGCCT CCAGGGAAGG GCCTGGAATG

GCTGGGCGTG ATCTGGACCG GCGGCACCAC CAACTACAAC TCCGCCCTGA

TGTCCCGGCT GACCATCTCC AAGGACGACT CCAAGTCCAC CGTGTACCTG

AAGATGAACT CCCTGAAAAC CGAGGACACC GCCATCTACT ACTGCGCCCG

GTACTACTAC GGCATGGACT ACTGGGGCCA GGGCACCTCC GTGACCGTGT CCTCA (SEQ ID NO: 20)
VH2: CAGGTGCAGC TGCAGGAATC CGGCCCTGGC CTGGTCAAGC

CCTCCGAGAC ACTGTCCCTG ACCTGCACCG TGTCCGGCTT CTCCCTGCTG

TCCTACGGCG TGCACTGGGT CCGACAGCCT CCAGGCAAAG GCCTGGAATG

GCTGGGCGTG ATCTGGACCG GCGGCACCAC CAACTACAAC TCCGCCCTGA

TGTCCCGGCT GACCATCTCC AAGGACGACT CCAAGAACAC CGTGTACCTG

AAGATGAACT CCCTGAAAAC CGAGGACACC GCCATCTACT ACTGCGCCCG

GTACTACTAC GGCATGGACT ACTGGGGCCA GGGCACCCTG GTCACCGTGT CCTCA (SEQ ID NO: 21)
VH3: CAGGTGCAGC TGCAGGAATC CGGCCCTGGC CTGGTCAAGC

CCTCCGAGAC ACTGTCCCTG ACCTGCACCG TGTCCGGCTT CTCCCTGCTG

TCCTACGGCG TGCACTGGGT CCGACAGCCT CCAGGCAAAG GCCTGGAATG

GCTGGGCGTG ATCTGGACCG GCGGCACCAC CAACTACAAC TCCGCCCTGA

TGTCCCGGTT CACCATCTCC AAGGACGACT CCAAGAACAC CGTGTACCTG

AAGATGAACT CCCTGAAAAC CGAGGACACC GCCATCTACT ACTGCGCCCG

GTACTACTAC GGCATGGACT ACTGGGGCCA GGGCACCCTG GTCACCGTGT CCTCA (SEQ ID NO: 22)
VH4: CAGGTGCAGC TGCAGGAATC CGGCCCTGGC CTGGTCAAGC

CCTCCGAGAC ACTGTCCCTG ACCTGCACCG TGTCCGGCTT CTCCCTGCTG

TCCTACGGCG TGCACTGGGT CCGACAGCCT CCAGGCAAAG GCCTGGAATG

GCTGGGCGTG ATCTGGACCG GCGGCACCAC CAACTACAAC TCCGCCCTGA

TGTCCCGGTT CACCATCTCC AAGGACGACT CCAAGAACAC CCTGTACCTG

AAGATGAACT CCCTGAAAAC CGAGGACACC GCCATCTACT ACTGCGCCCG

GTACTACTAC GGCATGGACT ACTGGGGCCA GGGCACCCTG GTCACCGTGT CCTCA (SEQ ID NO: 23)
Vk1: GACATCGTGA TGACCCAGTC CCCCAGCTTC CTGTCCGCCT

CCGTGGGCGA CAGAGTGACC ATCACATGCA AGGCCTCTCA GGACGTGCGG

AACACCGTGG CCTGGTATCA GCAGAAAACC GGCAAGGCCC CCAAGCTGCT

GATCTACTCC TCCTCCTACC GGAACACCGG CGTGCCCGAC CGGTTTACCG

GCTCTGGCTC CGGCACCGAC TTTACCCTGA CCATCAGCTC CCTGCAGGCC

GAGGACGTGG CCGTGTACTT CTGCCAGCAG CACTACATCA CCCCCTACAC

CTTCGGCGGA GGCACCAAGG TGGAAATAAA A (SEQ ID NO: 24)
Vk2: GACATCGTGA TGACCCAGTC CCCCTCCAGC CTGTCCGCCT

CTGTGGGCGA CAGAGTGACC ATCACATGCA AGGCCTCTCA GGACGTGCGG

AACACCGTGG CCTGGTATCA GCAGAAGCCC GGCAAGGCCC CCAAGCTGCT

-continued

```
GATCTACTCC TCCTCCTACC GGAACACCGG CGTGCCCGAC CGGTTTACCG

GCTCTGGCTC CGGCACCGAC TTTACCCTGA CCATCAGCTC CCTGCAGGCC

GAGGACGTGG CCGTGTACTT CTGCCAGCAG CACTACATCA CCCCCTACAC

CTTCGGCGGA GGCACCAAGG TGGAAATAAA A
```

(SEQ ID NO: 25)
```
Vk3: GACATCCAGA TGACCCAGTC CCCCTCCAGC CTGTCCGCCT

CTGTGGGCGA CAGAGTGACC ATCACATGCA AGGCCTCCCA GGACGTGCGG

AACACCGTGG CCTGGTATCA GCAGAAGCCC GGCAAGGCCC CCAAGCTGCT

GATCTACTCC TCCTCCTACC GGAACACCGG CGTGCCCGAC CGGTTCTCTG

GCTCTGGAAG CGGCACCGAC TTTACCCTGA CCATCAGCTC CCTGCAGGCC

GAGGACGTGG CCGTGTACTT CTGCCAGCAG CACTACATCA CCCCCTACAC

CTTCGGCGGA GGCACCAAGG TGGAAATAAA A
```

(SEQ ID NO:26)
```
Vk4: GACATCCAGA TGACCCAGTC CCCCTCCAGC CTGTCCGCCT

CTGTGGGCGA CAGAGTGACC ATCACATGCA AGGCCTCTCA GGACGTGCGG

AACACCGTGG CCTGGTATCA GCAGAAGCCC GGCAAGGCCC CCAAGCTGCT

GATCTACTCC TCCTCCTACC GGAACACCGG CGTGCCCGAC CGGTTCTCTG

GCTCTGGAAG CGGCACCGAC TTTACCCTGA CCATCAGCTC CCTGCAGGCC

GAGGACGTGG CCGTGTACTA CTGCCAGCAG CACTACATCA CCCCCTACAC

CTTCGGCGGA GGCACCAAGG TGGAAATAAA A
```

Because the structure of antibodies, including the juxtaposition of CDRs and framework regions in the variable region, the structure of framework regions and the structure of heavy- and light-chain constant regions, is well-known in the art; it is well within the skill of the art to obtain related nucleic acids that encode anti-MMP-9 antibodies. Accordingly, polynucleotides comprising nucleic acid sequences having at least 75%, at least 80%, at least 85%, at least 90%, at least 95%, at least 98% and at least 99% homology to any of the nucleotide sequences disclosed herein are also provided. Accordingly, polynucleotides comprising nucleic acid sequences having at least 75%, at least 80%, at least 85%, at least 90%, at least 95%, at least 98% and at least 99% identity to any of the nucleotide sequences disclosed herein are also provided. In one example, the polynucleotide contains at least at or about 75%, 80%, 85%, 90%, 91%, 92%, 93%, 94%, 95%, 96%, 97%, 98%, 99% or more sequence identity with SEQ ID NO: 21 or includes or is SEQ ID NO: 21 and/or contains at least at or about 75%, 80%, 85%, 90%, 91%, 92%, 93%, 94%, 95%, 96%, 97%, 98%, 99% or more sequence identity with SEQ ID NO: 26 or includes or is SEQ ID NO: 26.

Pharmaceutical Compositions

MMP9 binding proteins, as well as nucleic acid (e.g., DNA or RNA) encoding MMP9 binding proteins, can be provided as a pharmaceutical composition, e.g., combined with a pharmaceutically acceptable carrier or excipient. Such pharmaceutical compositions are useful for, for example, administration to a subject in vivo or ex vivo, and for diagnosing and/or treating a subject with the MMP9 binding proteins, such as in any of the therapeutic or diagnostic methods provided herein.

Pharmaceutically acceptable carriers or excipients are physiologically acceptable to the administered patient and retain the therapeutic properties of the antibodies or peptides with which it is administered. Pharmaceutically-acceptable carriers or excipients and their formulations are and generally described in, for example, Remington' pharmaceutical Sciences (18th Edition, ed. A. Gennaro, Mack Publishing Co., Easton, Pa. 1990). One exemplary pharmaceutical carrier is physiological saline. Each carrier or excipient is "pharmaceutically acceptable" in the sense of being compatible with the other ingredients of the formulation and not substantially injurious to the patient.

Pharmaceutical compositions can be formulated to be compatible with a particular route of administration, systemic or local. Thus, pharmaceutical compositions include carriers, diluents, or excipients suitable for administration by various routes.

Pharmaceutical compositions can include pharmaceutically acceptable additives. Examples of additives include, but are not limited to, a sugar such as mannitol, sorbitol, glucose, xylitol, trehalose, sorbose, sucrose, galactose, dextran, dextrose, fructose, lactose and mixtures thereof. Pharmaceutically acceptable additives can be combined with pharmaceutically acceptable carriers and/or excipients such as dextrose. Additives also include surfactants such as polysorbate 20 or polysorbate 80.

The formulation and delivery methods will generally be adapted according to the site and the disease to be treated. Exemplary formulations include, but are not limited to, those suitable for parenteral administration, e.g., intravenous, intra-arterial, intramuscular, or subcutaneous administration, or oral administration.

Pharmaceutical compositions for parenteral delivery include, for example, water, saline, phosphate buffered saline, Hank's solution, Ringer's solution, dextrose/saline, and glucose solutions. The formulations can contain auxiliary substances to approximate physiological conditions, such as buffering agents, tonicity adjusting agents, wetting agents, detergents and the like. Additives can also include additional active ingredients such as bactericidal agents, or stabilizers. For example, the solution can contain sodium acetate, sodium lactate, sodium chloride, potassium chloride, calcium chloride, sorbitan monolaurate or triethanolamine oleate. Additional parenteral formulations and methods are described in Bai (1997) J. Neuroimmunol. 80:65 75; Warren (1997) J. Neurol. Sci. 152:31 38; and Tonegawa (1997) J. Exp. Med. 186:507 515. The parenteral preparation can be enclosed in ampules, disposable syringes or multiple dose vials made of glass or plastic.

Pharmaceutical compositions for intravenous, intradermal or subcutaneous administration can include a sterile diluent, such as water, saline solution, fixed oils, polyethylene glycols, glycerine, propylene glycol or other synthetic solvents; antibacterial agents such as benzyl alcohol or methyl parabens; antioxidants such as ascorbic acid, glutathione or sodium bisulfite; chelating agents such as ethylenediaminetetraacetic acid; buffers such as acetates, citrates or phosphates and agents for the adjustment of tonicity such as sodium chloride or dextrose.

Pharmaceutical compositions for injection include aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). The carrier can be a solvent or dispersion medium containing, for example, water, ethanol, polyol (for example, glycerol, propylene glycol, and liquid polyetheylene glycol, and the like), and suitable mixtures thereof. Fluidity can be maintained, for example, by the use of a coating such as lecithin, by the maintenance of the required particle size in the case of dispersion and by the use of surfactants. Antibacterial and antifungal agents include, for example, parabens, chlorobutanol, phenol, ascorbic acid and thimerosal. Isotonic agents, for example, sugars, polyalcohols such as manitol, sorbitol, and sodium chloride may be included in the composition. The resulting solutions can be packaged for use as is, or lyophilized; the lyophilized preparation can later be combined with a sterile solution prior to administration.

Pharmaceutically acceptable carriers can contain a compound that stabilizes, increases or delays absorption or clearance. Such compounds include, for example, carbohydrates, such as glucose, sucrose, or dextrans; low molecular weight proteins; compositions that reduce the clearance or hydrolysis of peptides; or excipients or other stabilizers and/or buffers. Agents that delay absorption include, for example, aluminum monostearate and gelatin. Detergents can also be used to stabilize or to increase or decrease the absorption of the pharmaceutical composition, including liposomal carriers. To protect from digestion the compound can be complexed with a composition to render it resistant to acidic and enzymatic hydrolysis, or the compound can be complexed in an appropriately resistant carrier such as a liposome. Means of protecting compounds from digestion are known in the art (see, e.g., Fix (1996) Pharm Res. 13:1760 1764; Samanen (1996) J. Pharm. Pharmacol. 48:119 135; and U.S. Pat. No. 5,391,377, describing lipid compositions for oral delivery of therapeutic agents).

Compositions of the present invention can be combined with other therapeutic moieties or imaging/diagnostic moieties as provided herein. Therapeutic moieties and/or imaging moieties can be provided as a separate composition, or as a conjugated moiety present on an MMP9 binding protein.

Formulations for in vivo administration are generally sterile. In one embodiment, the pharmaceutical compositions are formulated to be free of pyrogens such that they are acceptable for administration to human patients.

Various other pharmaceutical compositions and techniques for their preparation and use will be known to those of skill in the art in light of the present disclosure. For a detailed listing of suitable pharmacological compositions and associated administrative techniques one can refer to the detailed teachings herein, which can be further supplemented by texts such as Remington: The Science and Practice of Pharmacy 20th Ed. (Lippincott, Williams & Wilkins 2003).

Pharmaceutical compositions can be formulated based on the physical characteristics of the patient/subject needing treatment, the route of administration, and the like. Such can be packaged in a suitable pharmaceutical package with appropriate labels for the distribution to hospitals and clinics wherein the label is for the indication of treating a disorder as described herein in a subject. Medicaments can be packaged as a single or multiple units. Instructions for the dosage and administration of the pharmaceutical compositions of the present invention can be included with the pharmaceutical packages and kits described below.

Methods of Use

The MMP9 binding proteins, including anti-MMP9 antibodies and fragments thereof, of the present disclosure can be used, for example, in therapeutic and diagnostic methods, such as methods of detection of MMP9 in a sample, methods of treatment (e.g., as in methods of inhibition of angiogenesis), and methods of diagnosis and prognosis. Thus, provided are diagnostic and therapeutic methods and uses of the anti-MMP9 antibodies. Examples of methods of use are described below.

Methods of Treatment

Provided herein are methods of treatment, including methods of treating diseases and disorders associated with MMP9 expression and/or activity, including cancer and inflammatory and autoimmune diseases and associated conditions, as well as uses of the provided antibodies and compositions in such methods. The diseases and disorders include, but are not limited to cancer, e.g., tumors (e.g., primary or metastatic tumors), such as those that express or are disposed in a tissue which expresses MMP9, such as colorectal and other cancers, such as gastric adenocarcinoma, colorectal adenocarcinoma, hepatocellular carcinoma, and other tumor types, and inflammatory and autoimmune diseases and conditions, such as IBD, including UC, Crohn's disease, collagenous colitis, rheumatoid arthritis, and other disorders associated with inflammation and MMP9-mediated tissue destruction.

In some cases, the disease or condition is advanced pancreatic or esophagogastric adenocarcinoma, non-small cell lung cancer, lung squamous cell carcinoma, lung adenocarcinoma, gastric adenocarcinoma, colorectal carcinoma, pancreatic adenocarcinoma, head and neck squamous cell carcinoma, or hepatocellular carcinoma.

As demonstrated in the Examples, expression of matrix metalloproteinases (MMPs) and MMP9 in particular is associated with a variety of disease pathologies, including inflammatory diseases and oncology. MMP9 can promote disease through its destructive remodeling of basement membrane and other structural proteins, and/or by increasing vascular permeability and bioavailability of growth factors and cytokines such as TGFβ, VEGF, TNFα, IL-6, and IL-1β. MMP9 regulates the bioavailability of ECM-sequestered VEGF and FGF-2, as well as membrane-tethered EGF. As described in the Examples, specific inhibition of MMP9, using antibodies as described herein, was efficacious in models of accepted mouse models of cancer and inflammatory diseases, such as rheumatoid arthritis, primary and metastatic colorectal cancer, and ulcerative colitis (UC).

As used herein, "treat" or "treatment" means stasis or a postponement of development of one or more symptoms associated with a disease or disorder described herein, or ameliorating existing uncontrolled or unwanted symptoms, preventing additional symptoms, or ameliorating or preventing the underlying metabolic causes of symptoms. Thus, the terms denote that a beneficial result has been conferred on a mammalian subject with a disease or symptom, or with the potential to develop such disease or symptom. A response is achieved when the patient experiences partial or total alleviation, or reduction of signs or symptoms of illness, and specifically includes, without limitation, prolongation of survival. The expected progression-free survival times can be measured in months to years, depending on prognostic factors including the number of relapses, stage of disease, and other factors.

Also provided are pharmaceutical compositions for use in connection with such methods, such as those containing any of the antibodies or fragments thereof described herein. Compositions can be suitable for administration locally or systemically by any suitable route.

In general, MMP9 binding proteins are administered in a therapeutically effective amount, e.g., in an amount to effect inhibition of tumor growth in a subject, to inhibit metastasis, to inhibit MMP9 activity, or to treat the particular disease or condition, such as cancer, inflammatory disease or condition, or autoimmune disease or condition.

As used herein, unless otherwise specified, the term "therapeutically effective amount" or "effective amount" refers to an amount of an agent or compound or composition that when administered (either alone or in combination with another therapeutic agent, as may be specified) to a subject is effective to prevent or ameliorate the disease condition or the progression of the disease, or result in amelioration of symptoms, e.g., treatment, healing, prevention or amelioration of the relevant medical condition, or an increase in rate of treatment, healing, prevention or amelioration of such conditions. When applied to an individual active ingredient administered alone, a therapeutically effective dose refers to that ingredient alone. When applied to a combination, a therapeutically effective dose refers to combined amounts of the active ingredients that result in the therapeutic effect, whether administered in combination, serially or simultaneously. In one example, when in vivo administration of an anti-MMP9 antibody is employed, normal dosage amounts can vary from about 10 ng/kg to up to 100 mg/kg of mammal body weight or more per day, preferably about 1 μg/kg/day to 50 mg/kg/day, optionally about 100 μg/kg/day to 20 mg/kg/day, 500 μg/kg/day to 10 mg/kg/day, or 1 mg/kg/day to 10 mg/kg/day, depending upon the route of administration.

In some examples, the antibody or fragment thereof is administered intravenously, for example, at a dose from about 1 mg/kg to at or about 30 mg/kg. In some examples, the antibody or fragment is administered intravenously, for example, at a dose of about 2 mg/kg to about 28 mg/kg. In some examples, the antibody or fragment is administered intravenously, for example, at a dose of about 4 mg/kg to about 28 mg/kg. In other example, the antibody or fragment is administered intravenously at a dose of about 1 mg/kg to at or about 14 mg/kg, such as from at or about 2 mg/kg to at or about 14 mg/kg, q14d, once every 14 days. In some embodiments, the effective amount of dosage is administered once every 7 to 28 days. In one embodiment, the effective amount of dosage is administered once every 7 days. In another embodiment, the effective amount of dosage is administered once every 28 days.

In one embodiment, the antibody or fragment thereof is administered subcutaneously, for example, at a dose from about 1 mg/kg to at or about 30 mg/kg. In other embodiments, subcutaneous dosages range from at or about 1 mg/kg to at or about 28 mg/kg, such as from at or about 2 mg/kg to at or about 28 mg/kg, once every 14 days. In other example, the antibody or fragment is administered subcutaneously at a dose of about 1 mg/kg to at or about 14 mg/kg, such as from at or about 2 mg/kg to at or about 14 mg/kg, once every 14 days. In some embodiments, the effective amount of dosage is administered once every 7 to 28 days. In one embodiment, the effective amount of dosage is administered once every 7 days. In another embodiment, the effective amount of dosage is administered once every 28 days.

In some examples, the antibody is administered, e.g., intravenously, at a dose of 50, 75, 100, 125, 150, 175, 200, 225, 250, 275, 300, 325, 350, 375, 400, 425, 450, 475, 500, 525, 550, 570, 600, 625, 650, 675, 700, 725, 750, 775, 800, 825, 850, 875, 900, 925, 950, 975, or 1000 mg/Kg body weight. In other examples, the antibody is administered, e.g. intravenously, at a dosage of 1100, 1200, 1300, 1400, 1500, 1600, 1700, or 1800 mg/Kg. In some examples, the antibody is administered, e.g., intravenously, at a dose of 100, 200, 400, 600, 1200, or 1800 mg/Kg body weight, and in some examples at a dosage of 133, 267, 400, 600 or 1200 mg/Kg. In some examples, the antibody is administered the interval of one, two or three weeks, or once every one, two, or three weeks. In some examples, the appropriate dosage is made with 0.9% sodium chloride.

The selected dosage regimen will depend upon a variety of factors including the activity of the MMP9 binding protein, the route of administration, the time of administration, the rate of excretion of the particular compound being employed, the duration of the treatment, other drugs, compounds and/or materials used in combination with the particular composition employed, the age, sex, weight, condition, general health and prior medical history of the patient being treated, and like factors well known in the medical arts.

In some embodiments, dosage is determined based on a pharmacokinetic model for antibodies displaying target-mediated disposition. In contrast to the relatively linear pharmacokinetics observed for antibodies directed to soluble receptor targets, antibodies directed toward tissue-based target receptors frequently demonstrate non-linear pharmacokinetics. Mager, D. E. (2006), Adv Drug Deliv Rev 58(12-13): 1326-1356. The basis for non-linear disposition relates to the high affinity binding of antibody to target and the extent of binding (relative to dose), such that the interaction is reflected in the pharmacokinetic characteristics of the antibody. Mager, D. E. and W. J. Jusko (2001), J Pharmacokinet Pharmacodyn 28(6): 507-532. Included within target mediated drug disposition is receptor-mediated endocytosis (internalization) of the antibody-receptor complex. Wang, W., E. Q. Wang, et al. (2008), Clin Pharmacol Ther 84(5): 548-558.

In a pharmacokinetic model for an antibody having target-mediated disposition, in the absence of drug (antibody), the target receptor is synthesized at a constant rate and eliminated by a first-order process. As a result, the target receptor exists at a steady-state concentration in the absence of drug (antibody). When drug is added to the body it can interact with the target receptor in a bimolecular reaction, distribute into less well perfused tissue, or be eliminated via first-order processes. At low drug concentrations the predominant movement of drug is onto the receptor due to the high affinity binding. As the amount of drug entering the body becomes sufficient to bind the available mass of receptor the drug distributes into and out of tissue and is eliminated. As drug concentrations fall and drug equilibrates from tissue this provides an additional reservoir to binding newly synthesized receptor.

A clinician having ordinary skill in the art can readily determine and prescribe the effective amount (ED50) of the pharmaceutical composition required. For example, the physician or veterinarian can start doses of the compounds of the invention employed in the pharmaceutical composition at levels lower than that required in order to achieve the desired therapeutic effect and gradually increase the dosage until the desired effect is achieved.

In some cases, the methods of treatment include parenteral administration, e.g., intravenous, intra-arterial, intradermal, intramuscular, or subcutaneous administration, or oral administration of the agent, e.g., anti-MMP9 antibody or composition containing the same.

As used herein, the term "subject" means a mammalian subject. Exemplary subjects include, but are not limited to humans, monkeys, dogs, cats, mice, rats, cows, horses, goats and sheep. In some embodiments, the subject has cancer, an inflammatory disease or condition, or an autoimmune disease or condition, and can be treated with the agent of the present invention as described below. In certain embodiments, the subject is a human having cancer, an inflammatory disease or condition, or an autoimmune disease or condition, and can be treated with the agent of the present invention as described below.

If needed, for treatments, methods can further include additional therapies, such as in the case of cancer, surgical removal of the cancer and/or administration of an anti-cancer agent or treatment in addition to an MMP9 binding protein. Administration of such an anti-cancer agent or treatment can be concurrent or sequential with administration of the compositions disclosed herein.

In some embodiments, the antibody is administered alone, as a monotherapy. In other embodiments, the antibody is administered as part of a combination therapy with one or more other therapeutic agents. The therapeutic agents include but are not limited to the agents that are suitable for treating inflammation, autoimmune diseases, fibrotic diseases, or cancers. The therapeutic agents may be chemotherapeutic, immunotherapeutic, anti-cancer, anti-inflammatory, or anti-fibrotic agents. In the combination therapy, the antibody of the present application may be used as the primary or front-line agent or the secondary or additional agent in treating patients in need thereof. In some aspects, for treating an inflammatory, fibrotic or autoimmune disease, such as IBD, UC, Crohn's disease, cancer, or rheumatoid arthritis, the antibody is administered alone or with other therapeutic agents that inhibit or modulate the activities of kinases, such as apoptosis signal-regulating kinase, spleen tyrosine kinase, phosphatidylinositide 3-kinases, or Janus kinase, or lysyl oxidase, lysyl oxidase-like (LOXL) protein such as LOXL2 and/or discoidin domain receptor (DDR) such as DDR1. By way of example, the therapeutic agent inhibiting or modulating the activities of LOXL2 and DDR1, are antibodies that specifically binds to LOXL2 and/or DDR1. In one aspect, the anti-LOXL2 antibodies described in US2009/0104201, US2009/0053224 and US 2011-0200606 and the anti-DDR1 antibodies described in U.S. Provisional Application No. 61/705,044 are used in the combination therapy; all of these documents are incorporated herein by reference. In other aspects, for treating patients having cancer, the antibody is administered alone or in combination with one or more chemotherapeutic or anti-neoplastic agents, such as gemcitabine, nab-paclitaxel, mFOLFOX6 mFOLFOX6 consisting of folinic acid, fluorouracil (5-FU) and oxaliplatin, FOLFIRI consisting of folinic acid, fluorouracil (5-FU) and irinotecan, carboplatin, paclitaxel, pemetrexed and/or bevacizumab. In one for pancreatic adenocarcinoma, the antibody is administered alone at a two-week interval or with a 28-day cycle chemotherapy of gemcitabine and/or nab-paclitaxel. In one example, for esophagogastric adenocarcinoma, the antibody is administered alone at a two-week interval or with a 28-day cycle chemotherapy of mFOLFOX6 that is administered in a 28-day cycle. In one example, for non-small cell lung cancer, the antibody is administered alone at a three-week interval or with a 21-day cycle chemotherapy of carboplatin and paclitaxel or with pemetrexed and/or bevacizumab. In one example, for colorectal cancer, the antibody is administered alone at a two-week interval or with a 14-day cycle chemotherapy of FOLFIRI. In the combination treatments, the chemotherapy can be administered with the known dosage and procedure.

In some embodiments, the antibody, e.g., AB0045, is used in treating patients having advanced pancreatic or esophagogastric adenocarcinoma, non-small cell lung cancer, ulcerative colitis, colorectal cancer, Crohn's disease, or rheumatoid arthritis. In some aspects of such embodiments, the patients are administered the antibody intravenously at a dosage of 100, 200, 300, 400, 500, 600, 700, 800, 900, 1000, 1100, 1200, 1300, 1400, 1500, 1600, 1700, or 1800 mg/Kg body weight, at the interval of one, two or three weeks. In some aspects, the appropriate dosage is made with 0.9% sodium chloride. In some aspects, the patients receive the antibody, e.g., AB0045, as monotherapy or as part of a combination therapy with other therapeutic agents.

In some embodiments, for treating UC, cancers such as colorectal cancers, pancreatic cancers, gastric cancers, Crohn's disease, inflammatory or fibrotic diseases or disorders, or rheumatoid arthritis, the antibody, e.g., AB0045, is administered alone or with other immunotherapeutic agents, including antibodies against LOXL2 (lysyl oxidase-like 2) and/or DDR1 (discoidin domain receptor 1).

In some embodiments, for pancreatic adenocarcinoma, the antibody is administered alone at the two-week interval or with the 28-day cycle chemotherapy of gemcitabine and/or nab-paclitaxel.

In some embodiments, for esophagogastric adenocarcinoma, the antibody is administered alone at the two-week interval or with the 28-day cycle chemotherapy of mFOLFOX6 that is administered in a 28-day cycle.

In some embodiments, for non-small cell lung cancer, the antibody is administered alone at the three-week interval or with the 21-day cycle chemotherapy of carboplatin and paclitaxel or with pemetrexed and/or bevacizumab.

In one example, for colorectal cancer, the antibody is administered alone at a two-week interval or with a 14-day cycle chemotherapy of FOLFIRI. In some aspects of the combination treatments, the chemotherapy or immunotherapy agent is administered with the known dosage and procedure.

In some aspects, the dosage of MMP9 antibody can be adjusted and administered at 133, 267, 400, 600 or 1200 mg/Kg body weight. After each therapeutic cycle, the patients are monitored for the levels of MMP9 antibodies, MMP9, or other suitable biomarkers.

The agents in a combination therapy can be administered, via a suitable route described above, simultaneously (in the same composition or separately), or sequentially, in any order.

In some embodiments, the treatment methods include steps for monitoring treatment, including for monitoring efficacy or activity, such as pharmacodynamic activity. In some examples, such methods include detecting or measuring the presence, absence, levels, and/or expression of markers, such as cytokines and other inflammatory markers that are indicative of efficacy of treatment, in biological test samples obtained from subjects being treated using the methods and compositions. The samples typically are blood samples or serum samples but can include other biological samples as described herein. Among the markers for use in such methods are Tissue Inhibitor of Metalloproteinases 1 (TIMP-1), Tumor Necrosis Factor alpha (TNF-alpha), Macrophage Inflammatory Protein-2 (MIP-2), Interleukin-17A (IL-17A), CXCL10, Lymphotactin, Macrophage Inflammatory Protein-1 beta (MIP-1 beta), Oncostatin-M (OSM), Interleukin-6 (IL-6), Monocyte Chemotactic Protein 3 (MCP-3), Vascular Endothelial Growth Factor A (VEGF-A), Monocyte Chemotactic Protein-5 (MCP-5), Interleukin-1 alpha (IL-1 alpha), Macrophage Colony-Stimulating Factor-1 (M-CSF-1), Myeloperoxidase (MPO), Growth-Regulated Alpha Protein (KC/GRO), Interleukin-7 (IL-7), Leukemia Inhibitory Factor (LIF), Apolipoprotein A-I (Apo A-I), C-Reactive Protein (CRP), Granulocyte Chemotactic Protein-2 (GCP-2), Interleukin-11 (IL-11), Monocyte Chemotactic Protein 1 (MCP-1), von Willebrand factor (vWF), and Stem Cell Factor (SCF) gene products. In some embodiments, the markers are selected from among KC/GRO, LIF, CXCL10, MPO, MIP-2, and MCP-5 gene products, for example, when the diseases is IBD, such as UC.

In some embodiments, after each therapeutic cycle, the patients are monitored for the levels of MMP9 antibodies, MMP9, or other suitable biomarkers.

Among the provided methods are those that provide improved safety profiles compared to available treatments and therapeutic regimens and/or sustained long-term efficacy in treating such diseases and conditions.

Inflammatory and Autoimmune Diseases and Conditions

In some embodiments, the methods and compositions, e.g., antibodies and fragments thereof, are used in the treatment of inflammatory and autoimmune disease, e.g., by inhibiting MMP9 in subjects having such diseases or conditions. Among the inflammatory and autoimmune diseases are inflammatory bowel disease (IBD) (including Crohn's disease, ulcerative colitis (UC), and indeterminate colitis), collagenous colitis, rheumatoid arthritis, septicemia, multiple sclerosis, muscular dystrophy, lupus, allergy, septicemia, and asthma.

As described in the Examples, MMP9 and other MMPs are involved in inflammatory and autoimmune diseases.

Matrix metalloproteinase-9 (MMP9) is induced in the serum, synovial fluid, and synovium of RA patients, and the MMP9/TIMP-1 ratio is altered in favor of increased proteolytic activity. MMP9 is secreted by disease-mediating osteoclasts and activated cells of the monocyte/macrophage lineage. Resistance to antibody-induced arthritis disease phenotypes is observed in a MMP9 knock-out mouse strain. MMP9 degrades the unwound collagen II created by the cleavage activity of collagenases, such as MMP8, and thereby contributes to the destruction of articular cartilage.

Given important roles of other MMPs, however, specific MMP9 inhibitors are needed to treat such diseases. As shown in the Examples herein, antibodies of the invention were demonstrated as effective in various inflammatory and autoimmune diseases, including IBD, rheumatoid arthritis (RA), and septicemia, using accepted animal models. Thus, in some embodiments, the methods, compositions, and uses treat subjects having inflammatory and autoimmune diseases. In some embodiments, the inhibitors, methods, and uses inhibit MMP9 without inhibiting other MMPs, such as without inhibiting MMP2, or without inhibiting such other MMPs to a substantial degree. In one embodiment, the methods protect against or reduce tissue injury, systemic inflammation, and/or local inflammation in a subject having such a disease or condition; in some examples, both tissue injury and inflammation are treated by the methods. In another embodiment, the methods are associated with reduced toxicity and/or reduced induction of musculoskeletal syndrome (MSS) or similar symptoms, compared to that observed with pan-MMP inhibitors, such as Marimastat. In some examples, the subject has had an inadequate response to another therapy for the inflammatory disease, such as a TNF-antagonist, such as an anti-TNF antibody, e.g., infliximab, i.e., has TNF-antagonistic refractive disease. Thus, among the provided methods are those effective at treating inflammation in such subjects.

Inflammatory Bowel Disease

Inflammatory bowel diseases (IBDs) include Crohn's disease, ulcerative colitis (UC), and indeterminate colitis). Ulcerative colitis (UC) is one of the two major IBDs, characterized by diffuse mucosal inflammation, and associated ulceration, of the colon. The chronic course of UC includes intermittent disease exacerbations followed by periods of remission. Many patients experience insufficient response to agents such as anti-TNFα targeted therapeutics and continue to suffer from disease-related symptoms. Patients with UC have a significantly elevated risk of colon cancer after 8-10 years of disease activity.

Inflammatory bowel disease (IBD) therapeutics can modulate disease by preventing recruitment and access of inflammatory cells to the disease site, preventing activation of cells at the disease site, and/or inhibiting the downstream effects of cell activation.

UC pharmacologic treatment generally proceeds 'by line' based on disease severity and the location or extent of the disease. Disease severity is characterized as mild, moderate or severe based on patient symptoms, endoscopic findings, and laboratory results and in the clinical trial setting often defined by the Mayo Score, as shown in Table 1B.

TABLE 1B

UC Mayo Score

| Subscore | Definition |
|---|---|
| Stool Frequency | |
| 0 | Normal for the patient |
| 1 | 1-2 stools more than normal |
| 2 | 3-4 stools more than normal |
| 3 | ≥5 stools more than normal |
| Rectal Bleeding | |
| 0 | No blood seen |
| 1 | Streaks of blood with stool less than half of the time |

TABLE 1B-continued

UC Mayo Score

| Subscore | Definition |
|---|---|
| 2 | Obvious blood with stool most of the time |
| 3 | Blood alone passes |
| | Findings on Endoscopy |
| 0 | Normal or inactive disease |
| 1 | Mild disease (erythema, decreased vascular pattern, mild friability) |
| 2 | Moderate disease (marked erythema, lack of vascular pattern, friability, erosions) |
| 3 | Severe disease (spontaneous bleeding ulceration) |
| | Physician's global assessment |
| 0 | Normal |
| 1 | Mild disease |
| 2 | Moderate disease |
| 3 | Severe disease |

As described in the Examples, evidence supports a role for MMP9 in the pathology of ulcerative colitis (UC) and other inflammatory bowel diseases (IBDs). Broad-spectrum MMP inhibitors are efficacious in TNBS and DSS models of colitis (Naito and Yoshikawa 2005; Medina and Radomski 2006). While MMP9 and MMP2 are the two most closely related MMPs, with similar substrate specificities, MMP9 protein and activity are induced to a greater extent in IBD and preclinical colitis animal models and more strongly induced and associated with progressive disease in human UC; MMP2 is more ubiquitously expressed and plays is important for homeostasis of non-diseased tissue. Lack of MMP9 protects against colitis in the mouse dextran sodium sulfate (DSS)-induced model, while MMP2 serves a protective function for the colon. Neutrophil and lymphocyte accumulation in the DSS model is MMP9-dependent; there is evidence for epithelial cell-derived MMP9 contribution to tissue damage.

MMP9 was detected in human UC tissues, not in healthy colonic crypts (in which the distinct ring of collagen IV staining marked intact basement membranes), but in areas of disorganized collagen IV, which indicates loss of basement membrane integrity. MMP9 degrades collagen IV and other ECM components, allowing infiltration of inflammatory cells. In colitis, MMP9 activity in the mucosa can lead to degradation of the basement membranes underlying crypts, and mucosal damage and exposure of the submucosa to luminal bacteria. MMP9 degradation of the basement membrane around blood vessels can promote extravasation of leukocytes to the disease site. MMP9 activity in the extracellular matrix can activate and release inflammatory cytokines such as TNFα, IL-6, and IL1-B that contribute to disease progression.

Available UC therapies have not been entirely satisfactory. For example, different treatments generally are given based on severity, location and/or extent of disease. For less severe disease, treatments include 5'-aminosalicylate (5'-ASA) enemas, corticosteroid enemas and oral 5'-ASA preparations. Patients with more severe disease, and/or those failing to respond to first line therapies are generally treated with a course of oral corticosteroids. Immunomodulators such as azathioprine and 6-mercaptopurine (6-MP) are used to help wean subjects off steroids and to maintain remission. Anti-TNFα therapy, e.g., the chimeric antibody Remicade® (infliximab) is generally used in patients with more severe disease and for patients who are refractory to or dependent upon corticosteroids. Infliximab treatment generally fails to induce and maintain steroid-free remission over the long term. Only 20% of patients achieve a remission by week 8 and remain in remission through 54 weeks, with the majority of patients relapsing by week 30. Only 26% of patients were able to achieve a long-term remission completely free of corticosteroids. When the less stringent endpoint of response is evaluated instead of remission (indicating an incomplete reduction in symptoms), approximately 60% of patients fail to maintain this degree of relief over 30 or 54 weeks.

Cyclosporine has helped delay the need for surgery in patients hospitalized for fulminant UC, but its efficacy as a maintenance therapy has not been established. Surgery, consisting of a two-step total colectomy with ileal pouch anal anastomosis (IPAA) is curative. A total colectomy is, however, is an undesirable outcome for many patients, committing them to lifelong frequent bowel movements, a high risk of sexual dysfunction, and a 50% risk of developing pouchitis—an inflamed J pouch that results in diarrhea with or without rectal bleeding, tenesmus, urgency, pain, incontinence and fevers. Furthermore, the risk of female infertility is highly increased following IPAA surgery.

As demonstrated in the Examples herein, specific anti-MMP9 antibodies of the invention were demonstrated as effective in an accepted UC animal model, effectively protecting against tissue destruction and aberrant tissue remodeling, as well as local and systemic downregulation of pro-inflammatory factors. The antibodies had robust efficacy on multiple endpoints in treatment of DSS-induced colitis in mice, a well-established preclinical model used for evaluation of agents being considered for treatment of UC. Thus, in some embodiments, the methods and compositions are used to treat a subject with an inflammatory bowel disease, such as ulcerative colitis (UC), Crohn's disease, or indeterminate colitis. In some embodiments, the methods and antibodies inhibit the MMP9 without inhibiting other MMPs, such as MMP2.

In some examples, the methods and compositions protect against destruction of basement membrane, mucosal damage, exposure of submucosa to luminal bacteria, inflammation, cytokine activation and leukocyte extravasation. In some embodiments, the subject has moderate to severe UC, e.g., has severe UC. In some embodiments, the subject has steroid dependent UC. In some aspects, the treatment methods replace or are administered as an alternative to corticosteroid treatment.

In some embodiments, the subject has been non-responsive to other UC therapies, such as TNF (e.g., TNF-alpha) antagonists, such as anti-TNF antibodies (such as infliximab and/or adalimumab), i.e., TNF antagonist-refractory patients. For example, in some embodiments, the subject is a patient who has failed to achieve long-term remission on infliximab therapy or other TNF-alpha targeting treatment. In other cases, the subject has been non-responsive to another UC therapy such as oral or rectal application treatments such as enemas, suppositories and foam), 5-aminosalicylic acid (5-ASAs), oral and rectal application corticosteroids, immunosuppressants such as 6-mercaptopurine, azathioprine, methotrexate, and/or cyclosporine. In some aspects, the methods provide treatment with an improved safety protocol as compared to such treatments, or provide treatment with more sustained, long-term efficacy.

In some cases, the methods inhibit MMP9 without affecting other MMPs or particular other MMPS such as MMP2.

In some embodiments, in the context of UC, "response" to treatment is achieved if there is at least a 3 point and a 30% reduction in the Mayo Score with at least a 1 point reduction in the rectal bleeding subscore or an absolute rectal bleeding subscore of 0-1. In some embodiments, "remission" is defined as a Mayo score ≤2, with no individual subscore >1. In some embodiments, "mucosal healing" is defined as an endoscopic subscore of ≤1. In some embodiments, "steroid sparing" is defined as remission in the absence of ongoing steroid use for those patients who began on steroids. In some embodiments, quality of life is an endpoint and is assessed using known methods, such as a validated quality of life measure such as the IBD-QoL or the SF-36.

Crohn's disease (CD) is a chronic inflammatory disorder of the gastrointestinal tract defined by relapsing and remitting episodes, with progression to complications such as fistula formation, abscesses, or strictures. Extraintestinal manifestations such as uveitis, arthritis, skin lesions, and kidney stones occur in upwards of 40% of patients. The treatment paradigm for mild-to-moderate Crohn's has been antibiotics such as ciprofloxacin and flagyl, 5-ASAs, budesonide, or systemic corticosteroids, however, the long-term side effects of systemic steroids greatly dampens their utility. Patients with mild-to-moderate disease who fail these first line therapies are often placed on the on azathioprine remain in remission at one-year. For patients who fail azathioprine or those with more severe disease, TNF-α blockade with agents such as infliximab remain the last option. As opposed to UC where surgical resection is curative, such therapy is more difficult for Crohn's patients for two reasons: 1) disease is diffuse throughout the GI tract and in instances of isolated disease (e.g., terminal ileum), resection is frequently associated with recurrent disease at the site of the resection 2) since the disease is transmural, surgical resection places patients at risk for future stricture and/or fistula development.

While combination therapy using azathioprine and infliximab may be superior to either therapy alone for induction of remission and mucosal healing at 26 weeks, the concurrent use of such agents increases the risk of infection and malignancy (hepatosplenic T cell lymphoma), limiting their utility. As with UC, response, remission, mucosal healing, steroid sparing and quality of life will all be important endpoints, but in CD the Crohn's Disease Activity Index (CDAI) is generally the validated outcome instrument of choice and is described in Table 1C:

TABLE 1C

Crohn's Disease Activity Index:

| METRIC | VALUE | FORMULA |
| --- | --- | --- |
| Liquid stools | Daily total × 7 days | Total Sum × 2 |
| Abdominal Pain | Daily total × 7 days<br>NONE = 0<br>Intermediate = 1<br>Severe = 3 | Sum × 5 |
| General well being | Daily total × 7 days<br>Well = 0<br>Intermediate = 1, 2, 3<br>Terrible = 4 | Sum × 7 |
| Extra-intestinal | One point for each:<br>Arthritis/arthralgia<br>Iritis/uveitis<br>Skin/mouth ulcers<br>Peri-anal disease<br>Other fistula<br>Fever >37.8 C | Score × 20 |
| Anti-diarrheal use | YES/NO | Value × 30 |
| Abdominal Mass | None = 0<br>Questionable = 2<br>Definite = 5 | Value × 10 |

TABLE 1C-continued

Crohn's Disease Activity Index:

| METRIC | VALUE | FORMULA |
| --- | --- | --- |
| Hematocrit (Hct) | Males: 47-Hct<br>Females: 42-Hct | Value × 6 |
| Weight | | OCCASIONALLY USED |

Score <150 = Remission
Moderate Disease ≥220
Severe disease ≥450
Response to therapy = decrease of greater than 70 or alternatively 100 point decrease can be used to define response.

In some embodiments, the subject has moderate to severe CD, e.g., has severe CD. In some embodiments, the subject has steroid dependent CD. In some aspects, the treatment methods replace or are administered as an alternative to corticosteroid treatment.

In some embodiments, the subject has been non-responsive to other CD therapies, such as TNF antagonists, such as anti-TNF antibodies (such as infliximab and/or adalimumab), i.e., TNF antagonist-refractory patients. For example, in some embodiments, the subject is a patient who has failed to achieve long-term remission on infliximab therapy or other TNF-alpha targeting treatment. In other cases, the subject has been non-responsive to another CD therapy. In some aspects, the methods provide treatment with an improved safety protocol as compared to such treatments, or provide treatment with more sustained, long-term efficacy.

Cancer

In some embodiments, the methods and compositions, e.g., antibodies and fragments thereof, are used in the treatment of cancers and tumors and associated diseases and conditions. Exemplary cancers include colorectal cancers, gastric adenocarcinoma, colorectal adenocarcinoma, and hepatocellular carcinoma. TNF-α plays an important role in surveillance of malignancy and hence there is a risk of increased tumor formation with anti-TNF-α agents. Protection against colorectal tumorigenesis, as demonstrated herein in the Examples in the application, further distinguishes anti-MMP9 monoclonal antibody therapy from anti-TNF-alpha therapy. MMP9 plays a role in cellular invasion, metastasis, angiogenesis, and vasculogenesis. Similarly to observations in inflammatory disease, IHC analysis shows that MMP9 and MMP2 have distinct staining patterns in human tumor tissues, including colorectal cancer, with more consistent tumor-associated positivity observed for MMP-9.

Methods of Detection of MMP9

The present disclosure also contemplates methods of detecting MMP9 in a subject, e.g., to detect tumor or tumor-associated tissue expressing MMP9, or tissue or fluid or other biological sample associated with a disease as described herein, such as autoimmune or inflammatory disease. Thus, methods of diagnosing, monitoring, staging or detecting a tumor having MMP9 activity are provided.

Samples (e.g., test biological samples) from a subject (e.g., an individual suspected of having or known to have a tumor associated with MMP9 expression, or suspected of having or known to have another disease or condition, such as inflammatory or autoimmune disease as described herein), can be analyzed for MMP9 presence, absence, expression, and/or levels. For example, such samples can be collected and analyzed by detecting the presence or absence of binding of an MMP9 binding protein, such as an antibody or fragment as described herein, to substance (e.g., protein) in the sample. In some examples, the methods further include comparing the amount of binding detected to an amount of binding to a control sample, or comparing the detected level of MMP9 to a control level of MMP9. In some cases, the methods indicate the presence, absence, or severity of a disease or condition as described herein.

This analysis can be performed prior to the initiation of treatment using an MMP9 binding protein as described herein, or can be done as part of monitoring of progress of cancer treatment. In some embodiments, provided are methods of treatment, carried out by performing the detection assays and initiating, altering, or discontinuing treatment of the subject, for example, based on the results of the diagnostic assay. Such diagnostic analysis can be performed using any sample, including but not limited to tissue, cells isolated from such tissues, and the like. In some cases, the methods are performed on liquid samples, such as blood, plasma, serum, whole blood, saliva, urine, or semen. Tissue samples include, for example, formalin-fixed or frozen tissue sections.

Any suitable method for detection and analysis of MMP9 can be employed. Various diagnostic assay techniques known in the art can be adapted for such purpose, such as competitive binding assays, direct or indirect sandwich assays and immunoprecipitation assays conducted in either heterogeneous or homogeneous phases.

MMP9 binding proteins for use in detection methods can be labeled with a detectable moiety. The detectable moiety directly or indirectly produces a detectable signal. For example, the detectable moiety can be any of those described herein such as, for example, a radioisotope, such as 3H, 14C, 32P, 35S, or 125I, a fluorescent or chemiluminescent compound, such as fluorescein isothiocyanate (FITC), Texas red, cyanin, photocyan, rhodamine, or luciferin, or an enzyme, such as alkaline phosphatase, β-galactosidase or horseradish peroxidase.

Detection can be accomplished by contacting a sample under conditions suitable for MMP9 binding protein binding to MMP9, and assessing the presence (e.g., level) or absence of MMP9 binding protein-MMP9 complexes. A level of MMP9 in the sample in comparison with a level of a reference sample can indicate the presence of a tumor or tumor-associated tissues having MMP9 activity. The reference sample can be a sample taken from the subject at an earlier time point or a sample from another individual.

In some aspects, MMP9 mRNA is detected, such as by hybridization, such as by chromogenic in situ hybridization (CISH). In some aspects, such detection methods are used when high levels of inflammatory cell-derived MMP9 obscure signal in a desired cell type by other detection method, e.g., by IHC, e.g., in tumor epithelia.

Various aspects of the invention are further described and illustrated by way of the several examples which follow, none of which are intended to limit the scope of the invention.

EXAMPLES

Example 1

Immunogencity

The results confirmed that AB0045 and AB0041 have equivalent binding and inhibitory properties and that AB0046 can serve as a relevant mouse surrogate antibody, for example, in mouse models of human disease.

The potential clinical immunogenicity of the chimeric MMP9 antibody AB0041 and the humanized MMP9 antibody AB0045 was assessed. An ex vivo human T cell activation assay, the EpiScreen (Antitope, Ltd., Cambridge, UK) was used. The T cell activation in the EpiScreen assay has been correlated to the antibody/protein therapeutic responses in patients. The response of CD4+ T cell in 20 healthy donors, representing a variety of HLA haplotypes, was examined. Results showed that the AB0045 antibody did not induce response in any of the donors and that the AB0041 induced a response in 20% of the donors, with a magnitude of 2.29+/−0.36 (mean+/−standard deviation). A positive control of KLH induced a response in 95% of the donors, with a magnitude of 6.34+/−2.77 (mean+/−standard deviation). The results showed that that the AB0045 antibody is unlikely to be immunogenic.

Example 2

MMP9 Expression in Diseased and Healthy Colon Samples

Biopsy samples from human patients with ulcerative colitis (UC) and healthy individuals were examined by immunohistochemistry (IHC) using the MMP9-specific antibodies. Antibodies against myeloperoxidase (MPO, a neutrophil marker; Wirtz 2007), collagen IV (COLIV, basement membranes) and CD31 (endothelial cells) were used to assess disease severity and tissue infrastructure. Staining patterns of TIMP1 and MMP2 also were examined. PMK2 (a macrophage marker) also was assessed.

In the healthy samples, MMP9 immunoreactivity was detected only in a small subset of migrating histiocytes, neutrophils and lymphocytes within the lamina propria and submucosal regions. In contrast, in all seven UC samples, a more intense and disease-associated signal was detected. Among the samples, 5 were prepared by snap-frozen method and 2 were formalin-fixed and paraffin-embedded.

Increased MMP9 signal was detected in acute disease regions, including abscessed and necrotic crypts and cryptitis regions containing neutrophilic infiltrates. More dispersed MMP9 signal was apparent in the extensive inflammatory infiltrate (largely histiocytes) within the lamina propria. MMP9 protein was localized to histiocytes, neutrophils, and granulocytes, and also detected in the extracellular matrix (ECM) associated with the basement membranes of diseased crypts and vascular structures. In addition, MMP9 immunoreactivity was observed in crypt abscesses, regions of ulceration, and in luminal and crypt epithelial cells. TIMP1 protein, which is often co-expressed with MMP9, was also associated with the diseased crypts and inflammatory infiltrates, but to a lesser extent than MMP9. With the exception of a few lymphocytes, MMP2 protein was not detected in the UC samples.

Intense MMP9 expression was observed in regions of acute disease, including abscessed and necrotic crypts and regions of cryptitis containing neutrophilic infiltrates and in epithelial cells in disease regions. MMP9 expression was also apparent in the extensive inflammatory infiltrate within the lamina propria and was localized primarily to histiocytes and neutrophils. A distinct ring of collagen IV staining marks intact basement membranes of healthy crypts, whereas disorganized collagen IV indicates loss of basement membrane integrity in diseased crypts; MMP9 staining co-localized with regions of basement membrane disruption. TIMP1 protein was also associated with the diseased crypts and inflammatory infiltrates, but to a lesser extent than MMP9. In the Crohn's disease samples, the MMP9 signal was also associated with diseased regions. MMP9 was detected in granulomas, interstitial histocytes, and colocalized with vascular basement membrane and ECM collagen IV. Additionally, MMP was detected in lymphocytes and luminal epithelial cells. Some MMP2 reactivity was observed but was less prominent.

MMP9 signal was not detected in healthy colonic crypts but was strong in areas with disorganized collagen IV which indicated the loss of basement membrane integrity. This indicates a role for MMP9 in the pathology of ulcerative colitis.

MMP9 expression was evaluated in colon tissue from a UC patient being actively treated with Remicade® (infliximab), a therapeutic anti-TNF-alpha antibody, demonstrating a similar staining pattern to other UC patient colon tissue assessed. This observation is consistent with a conclusion that in this study, anti-TNF-alpha therapy did not prevent MMP9 induction in UC.

IHC analysis confirmed that the humanized variant anti-MMP9 antibody AB0045 bound to MMP9 in UC patient colon tissue with a similar staining pattern to that observed with a validated IHC anti-MMP9 antibody.

Example 3

MMP9 Expression in Normal Tissues

The levels of MMP9 protein in normal healthy tissues of human, rat, and cynomolgus monkey were analyzed by IHC. Twenty-two human snap-frozen tissues from cell types of lymph node, skeletal muscle, prostate, kidney, liver, lung, stomach, esophagus, heart, colon, small intestine, brain, ovary, pancreas, placenta, skin, spinal cord, spleen, skeletal muscle, testis, thyroid gland, and uterus were obtained from 3 individuals. IHC was conducted with two different anti-MMP9 antibodies that performed well in IHC: a rabbit monoclonal antibody (Abcam, catalog #ab76003) and a rabbit polyclonal antibody (Sigma, catalog #HPA001238). Similar staining patterns were detected using both antibodies. MMP9 was also detected in human thymus, tonsil, and bone marrow. Additional characterizations were conducted on some snap-frozen tissues from healthy cynomolgus monkeys (*Macaca fascicularis*, 1 individual animal) and rats (Sprague-Dawley strain, 2 individual animals).

MMP9 was not detected in heart, skeletal muscle, prostate, kidney, peripheral nerve, cerebellum, cerebrum, salivary glands, ureter, and cervix. In the rest of the organs tested, MMP9 was detected in cytoplasmic staining of immune cells such as macrophages, histiocytes, lymphocytes, mast cells, and neutrophils. Similar patterns of MMP9 protein expression was detected in all human, cynomolgus, and rat tissues examined. Fewer MMP9 positive inflammatory cells were detected in cynomolgus monkey lymph node, thymus and tonsil in the tissue analyzed. In all species, the MMP9 staining was intracellular rather than secreted or localized in the extracellular matrix.

Example 4

Anti-MMP9 Antibody in a Murine Model of UC

The dextran sodium sulfate (DSS)-induced model of colitis is an accepted model for evaluation of inflammatory bowel disease therapeutics. In this model, oral administration of DSS to mice or rats results in damage to the colonic mucosa. Animals receiving DSS develop bloody diarrhea and lose weight. The inflammation and tissue degradation observed in this model is restricted to the mucosa and generally affects the entire colon. DSS-induced colitis features the same inflammation-dysplasia-adenocarcinoma disease progression as seen in human UC. The localization of disease and the pathology observed in this model is considered to be reminiscent of human ulcerative colitis (UC), including similar inflammatory cell infiltrate, ulceration, and crypt abscesses. Drugs that are approved for treatment of UC, such as steroids, metronidazole, 5-aminocalicylates, cyclosporin, and anti-TNFα immunotherapy have demonstrated efficacy in reducing disease severity in the DSS model.

AB0046 was used in the DSS colitis model (in a 14-day treatment model). Treatment began after 5 days of oral exposure to 3% DSS in drinking water, according to the following experimental design: disease induction with 3% DSS was carried out beginning at day 0 through day 5, with treatment beginning at day 6 (treatment details for animals in groups 1-5 given in Table 2, below); animals were sacrificed at day 14. Etanercept (marketed under the trade name ENBREL®) was used as a reference compound for the therapeutic effect of anti-TNFα therapy in this model. AC-1, an irrelevant antibody of matched isotype (IgG1), was used as a control.

TABLE 2

Treatment details for animals in groups 1-5

| Group | N | Treatment | Dose (mg/kg) | ROA | Dosing Schedule | Video Endoscopy |
|---|---|---|---|---|---|---|
| 1 | 5 | Vehicle (−DSS) | equiv. vol. | IP | Days 6, 9, & 12 | Days 6, 10, & 14 |
| 2 | 14 | Vehicle (+DSS) | equiv. vol. | IP | Days 6, 9, & 12 | Days 6, 10, & 14 |
| 3 | 14 | AC-1 (+DSS) | 30 | IP | Days 6, 9, & 12 | Days 10 & 14 |
| 4 | 14 | AB0046 (+DSS) | 30 | IP | Days 6, 9, & 12 | Days 10 & 14 |
| 5 | 14 | ENBREL ® (+DSS) | 10 | IP | Days 6, 8, 10 & 12 | Days 10 & 14 |

N = Number of animals;
ROA = route of administration;
IP = intraperitoneal injection The course of disease was evaluated by video endoscopy (at days 6, 10, and 14), animal weight measurements, observation of stool consistency, and post-study histopathology analysis of colons.

Immunohistochemistry was performed in snap-frozen tissue sections from DSS treated colons to evaluate the extent of disease 14 days after study initiation (9 days after DSS cessation) and to confirm the expression of MMP9 in this model. The results are shown in FIG. 5. As shown, diseased regions showed destruction of tissue, the colonic epithelial boundary and crypt architecture, and infiltration of inflammatory cells. Strong staining for MMP9 was observed in the lamina propria of diseased colons and was associated with infiltrating neutrophils (MPO IHC) and macrophages. MMP9 immunoreactivity also co-localized with areas of basement membrane collagen IV staining around crypts and vascular structures, suggesting active degradation of this know ECM protein substrate was contributing to the disease progression. MMP2 expression was not strongly induced. As shown in FIG. 6, expression of MMP9 in colonic epithelial cells of DSS-exposed animals was also observed.

Video endoscopy of the lower colon was performed in a blinded fashion using a small animal endoscope; colitis was scored visually on a scale of 1-4 based on the degree of ulceration, friability, and vascularity present in the tissue. Each mouse was assigned a single score corresponding to the most severe damage observed throughout the entire length of the colon examined. The results are shown in FIG. 7. As shown, at study termination (Day 14), AB0046-treated animals showed a significant improvement in mean endoscopy scores in comparison to Vehicle and AC-1 isotype control groups. ENBREL® treatment also resulted in significant improvement in endoscopy scores, more pronounced at Day 10 and of lesser magnitude at day 14.

At study termination, the majority of the distal colon was excised from each animal, formalin-fixed, then embedded in paraffin and sectioned for histology. Slides were stained with hematoxylin and eosin and examined by a board-certified veterinary pathologist blinded as to treatment groups. Tissues were scored for inflammation, edema, and mucosal necrosis according to the scoring scale of 1-4 for each parameter. Sum pathology scores were calculated by summing the three individual parameter score means (inflammation, edema and necrosis). The results are shown in FIG. 8.

As shown in FIG. 8, histological assessment determined that DSS administration induced substantial inflammatory cell infiltration (primarily composed of neutrophils, with lesser numbers of macrophages), edema, and mucosal tissue necrosis when compared to the untreated control animals. Mucosal necrosis was variably present and characterized by partial or complete loss of the surface epithelium and crypts, often affecting approximately 25% of the circumferential mucosal surface. Therapeutic treatment with either AB0046 or ENBREL® significantly reduced all three aspects of disease pathology, compared to vehicle treatment. The efficacy of anti-MMP9 antibody (AB0046) was significant when compared to vehicle and was similar to that achieved by ENBREL®.

Immunohistological analysis of three colons from each study group, chosen to reflect the mean histopathology and endoscopy scores, revealed a reduction in MMP9 expression following anti-MMP9 antibody (AB0046) treatment that correlated with the reduced disease evident in these tissues (see FIG. 9), indicating that inhibition of MMP9 had not resulted in compensatory induction. In general, presence of MMP9 protein was well correlated with diseased regions. Reduction of MMP9 was also associated with ENBREL® treatment, although a significant amount of MMP9 protein was nonetheless detected. The results demonstrate that reduction of MMP9 correlated with reduction in overall disease.

Body weight and the incidence of diarrhea were recorded daily over the course of the study. The evaluation of body weight changes was performed by calculating the area under the curve (AUC) with the trapezoidal rule method; a similar calculation of AUC for stool consistency was performed by assigning incidence of diarrhea a score of 100 and lack of diarrhea a score of 0. The results are shown in FIG. 10. As shown, anti-MMP9 antibody (AB0046) treatment resulted in significant protection against body weight loss when compared with AC-1 isotype control or vehicle. AB0046 treatment also reduced the incidence of diarrhea by about 30%, which was similar to the effect of ENBREL® treatment, although the effect did not reach statistical significance for either therapy.

In the DSS model, reference compound administration rarely reduces endoscopic and histological disease by greater than 50%, with the typical responses falling in the range of 25-30%. The degree of efficacy with AB0046 was considered in this context. The efficacy of AB0046 in reaching statistical significance for reduction of histological disease, and the correlation between all parameters evaluated, was of particular note in this study. Although (given the limited dosing and evidence of a tissue-sink effect upon initial dosing) the antibody dosing regimen may not have achieved optimal therapeutic levels, efficacy was observed.

Consistent with the efficacy observed with endoscopic, histopathologic, and body weight endpoints, multianalyte enzyme-linked immunosorbent assay (ELISA) analysis of terminal serum samples from the treatment model in established disease revealed that anti-MMP9 (AB0046) treatment resulted in a systemic reduction of many known mediators and markers of the inflammatory process in UC, which were upregulated in the DSS model. As shown in FIG. 11A, these mediators included neutrophil chemoattractant factor KC/GRO, monocyte and activated T cell chemoattractant molecule CXCL10 (a therapeutic target in UC), neutrophil marker MPO, IL-6-class inflammatory cytokine LIF, neutrophil chemoattractant MIP-2, and monocyte chemotractant molecule MCP-5 (mouse factor sharing homology with human MCP-1). A trend for reduction of systemic disease-associated cytokines by AB0046 was observed. As shown in FIG. 11B, some cytokines were near or at the lower level of quantification or detection, including IL-17A (trend for a reduction in the AB0046-treated group mean was observed) and TNF-α (signal too low to assess differences between groups). A reduction of IL-6 was also observed with AB0046 treatment, but was not distinguished from AC-1 isotype control, an antibody that has demonstrated non-specific activity. Serum MMP-9 levels were not induced (i.e., no difference between no DSS and vehicle groups; interference by drug antibody cannot be ruled out for MMP9 serum level measurements). In addition to the reduction of MCP-5 levels observed in anti-MMP9 antibody (AB0046)-treated animals, disease-associated increases in MCP-1 and MCP-3 were also reduced with this treatment, as was eotaxin.

An additional mouse DSS colitis treatment study was conducted using AB0047, which was the anti-MMP9 antibody generated by an independent hybridoma. As shown in FIG. 12A, the results demonstrated similar trends for a reduction of endoscopic disease with anti-MMP9 AB0047 and ENBREL®. Also, as shown in FIG. 12B, AB0047 treatment resulted in similar trends in histopathological findings as with the study with AB0046.

Example 5

Anti-MMP9 Antibody in Murine DSS Model of Colitis

The efficacy of AB0046 in a prophylactic setting was assessed and compared with reference agent Prednisolone.

The treatment groups are shown in Table 3. The indicated treatment was given at day −1, with the indicated dosing schedules. Induction of disease with 3% DSS was initiated at day 0 and was as described above. Animals were sacrificed at day 14.

TABLE 3

Treatment details for animals in groups 1-5 in prophylactic study

| Group | N = | Treatment | Dose (mg/kg) | ROA | Dosing Schedule | Video Endoscopy |
|---|---|---|---|---|---|---|
| 1 | 5 | Vehicle (−DSS) | equiv. vol. | IP | Days −1, 2, 6, 9, & 12 | Days 6, 10, & 14 |
| 2 | 14 | Vehicle (+DSS) | equiv. vol. | IP | Days −1, 2, 6, 9, & 12 | Days 6, 10, & 14 |
| 3 | 14 | AB0046 (+DSS) | 30 | IP | Days −1, 2, 6, 9, & 12 | Days 6, 10, & 14 |
| 4 | 12 | PO Vehicle (+DSS) | equiv. vol. | IP | q.d. Days −1 to 14 | Days 6, 10, & 14 |
| 5 | 10 | Prednisolone (+DSS) | 3 | IP | q.d. Days −1 to 14 | Days 6, 10, & 14 |

N = Number of animals;
ROA = route of administration;
IP = intraperitoneal injection As shown in FIG. 13, efficacy of AB0046 prophylactic treatment was observed at the Day 10 endoscopic evaluation.

As shown in FIG. 14, at study termination, prophylactic anti-MMP9 (AB0046) treatment reduced inflammation, edema, and necrosis, and thus the pathology sum score. As shown in FIG. 15, prophylactic administration of AB0046 reduced the incidence of diarrhea.

Example 6

Anti-MMP9 Antibody in Orthotopic Model of Colorectal Cancer

The effectiveness of specific MMP9 inhibition was further shown using a cocktail of AB0046 and AB0041 in a xenograft mouse model of colorectal cancer. Fragments of subcutaneous tumors derived from a human colorectal cancer cell line (HCT-116; KRAS G13D mutant) were surgically implanted into the colon in nude mice and allowed to grow to ~100 mm³ prior to treatment initiation. As shown in FIG. 16, the antibody cocktail decreased change in tumor volume and decreased final tumor weight at day 32 after initiation of treatment (FIG. 16). Also, the antibody cocktail reduced the frequency of metastases (data not shown). The results shows that the inhibition of MMP9 using the antibody cocktail significantly decreased both primary tumor growth.

Example 7

Anti-MMP9 Antibody in Rheumatoid Arthritis Models

The anti-MMP9 antibody, AB0041, was efficacious in treating both inflammation and joint damage in both adjuvant and collagen-induced arthritis (AIA, CIA) rat rheumatoid arthritis models of established disease. Results are shown in FIG. 17A. Treatment using the anti-MMP9 monoclonal antibody AB0041 reduced arthritis clinical scores to a similar extent as that observed with established therapies ENBREL® and methotrexate (MTX) in a therapeutic model (treatment in established disease). Similar findings were observed for objective joint measurements and histopathological assessment of disease (sum score of multiple parameters of inflammation and joint destruction, 50 mg/kg group). As shown in FIG. 17A, reduction of arthritis clinical scores was observed with AB0041 doses of 50, 10 and 2 mg/kg, twice per week (4 doses altogether).

As shown in FIG. 17B, antibody titers were taken at end of study (EOS) to confirm exposure, and also at treatment day 10, in rat CIA. AB0046 was not detectable in serum at the 2 mg/kg dose level.

AB0041 treatment also was efficacious in reducing serum levels of key inflammatory cytokines such as TNFα, IL-6, and IL-17A, which are also characterized disease-drivers in human inflammatory bowel disease. The results are shown in FIG. 18A. FIG. 19A shows additional serum markers observed in this study.

Similar results for reduction of clinical and histopathological disease and the systemic anti-inflammatory effect of anti-MMP-9 treatment were observed in a CIA mouse model of rheumatoid arthritis using the murine surrogate antibody, AB0046. The cytokine results are shown in FIG. 18B; FIG. 19B shows additional serum markers observed in this study.

Example 8

Anti-MMP9 Antibody in LPS-Induced Septicemia Model

In another model of systemic inflammatory disease, anti-MMP9 antibody AB0041 treatment protected against lipopolysaccharide (LPS)-induced animal death in a rat septicemia model (Aragen Biosciences, Gilroy, Calif.), with 70% of AB0041-treated animals surviving after four days compared with 20% surviving in the isotype control-treated group. The results are shown in FIG. 20.

Example 9

Musculoskeletal Syndrome (MSS) Study

AB0041 was evaluated for safety in Lewis rats in comparison to the pan-MMP inhibitor, Marimastat, in a 28-day study.

Clinical administration of small molecule pan-MMP inhibitors, such as Marimastat, has been shown to result in musculoskeletal syndrome (MSS), a disorder characterized by pain and immobility in the shoulder joints, arthralgias, contractures in the hands, and reduced quality of life for patients. Rats treated with pan-MMP inhibitors also exhibit MSS (with symptoms including compromised ability to rest on hind feet, inability to move, and high-stepping gait) and are used as a model system for this disorder. Joints of these animals display synovial hyperplasia and increased cellularity similar to the histopathology observed in human disease. Using this rat model of musculoskeletal syndrome (MSS) (described in Renkiewicz R, et al., "Broad spectrum matrix metalloproteinase inhibitor marimastat-induced musculoskeletal side effects in rats." Arthritis Rheum 2003; 48 (6):1742-9), Marimastat treatment was used as a positive control for induction of MSS.

Six rats per group were intravenously administered twice per week with either AB0041 at 50 mg/kg or Vehicle-A (10 mM sodium phosphate, pH 6.5, 140 mM sodium chloride, 0.01% Tween20). In addition, six rats per group were treated with Marimastat or Vehicle-M (50% DMSO/50% water) through a surgically implanted subcutaneous Alzet pump (Alzet, Cupertino, Calif.), which delivered at a rate of 2.5 μl/hour for a period of 28 days. The Marimastat release rate was between 6.8 to 5.7 mg/kg/day.

Animals were observed and scored daily for signs of MSS, such as reluctance to move and avoidance of the use of the hind feet. The following system was used to score resting posture, gait and willingness to move: resting posture was scored as 0 (normal), 1 (resting on one foot) or 2 (resting on neither one foot nor two feet). Gait was scored as either 0 (normal), 1 (avoids use of one hind foot) or 2 (avoids use of both hind feet). Willingness-to-move upon stimulation was scored as either 0 (normal movement), 1 (somewhat reluctant to move), 2 (moderately reluctant to move) or 3 (very reluctant to move). In addition, the body weights were recorded twice weekly.

Total scores were calculated as the sum of gait score, resting posture score and willingness-to-move score for each animal. Mean total scores per group were calculated as the average of the total scores from all individual animals per group per day.

Serum was collected from all rats on one day before and days 1, 7, 10, 14, 17, 21, 24, 28 post administration. Serum was centrifuged at 10,000×g for 10 minutes and collected for storage at −20° C. Serum was subject to multianalyte serum protein analysis (RodentMAPv2.0, IDEXX Laboratories).

Tissues and limbs from the rats were harvested and fixed in 10% neutral buffered formalin for histopathologic analysis using hematoxylin and eosin (H&E).

A standard grading system was used to compare the microscopic change to the vehicle group: 0 (no change), 1 (minimal change), 2 (mild change), 3 (moderate change), and 4 (severe change).

Levels of AB0041 in rat serum were measured by an indirect binding ELISA. ELISA plates were coated with 2 μg/ml of AB0041 in 50 mM sodium borate overnight at 4° C. The plates were blocked with 5% bovine serum albumin (BSA) in phosphate buffered saline, pH 7.4 (PBS) and washed with 0.05% Tween 20 in PBS (PBST). A standard curve was prepared by serially diluting AB0041 in PBST to generate a series ranging from 3,000 ng/ml to 1.5 ng/ml. Serum samples were diluted at least 1:100 in PBST then added to the pre-coated ELISA plate. After one-hour incubation, the plates were washed and polyclonal goat-anti-mouse IgG-HRP detection antibody (Thermo Scientific, Fair Lawn, N.J.) was added to the plate at 1:10,000 dilution in 0.5% BSA/PBS. The plates were washed and signal was detected by addition of 3,3',5,5'-tetramethylbenzidine (TMB) (Sigma Aldrich, St. Louis, Mo.) for 2 minutes. The reaction was stopped by addition of 1M hydrochloric acid (HCl) and absorbance at 450 nm was measured. AB0041 levels in serum were back-calculated using a four-parameter curve fit in the SoftMax software package (Molecular Devices).

Results

No signs of weight loss were observed in any of the treatment groups; all animals continued to gain weight throughout the study.

Mean daily MSS scores±standard deviation for each group were summarized in FIG. 21. No signs of MSS were scored in the AB0041-treated rats throughout the study. At Day 12 of the study, five Marimastat-treated rats showed slight limping with avoidance of the use of one hind foot (gait score=1). No symptoms were detected in any animals treated with AB0041, Vehicle A, or Vehicle M. At Day 13, four animals in the Vehicle M group showed slight limping (gait score=1), which was likely due to the weight of the embedded pump. At Day 18, Marimastat-treated rats exhibited average daily total scores above 4.0, while Vehicle M-treated rats had low scores. By Day 25, the average score for the marimastat group was 5.8, and the average score for the AB0041 group remained zero. The difference in mean total scores per day between the Marimastat and Vehicle-M groups was statistically significant from Day 14 post-Alzet pump implantation onwards ($p<0.05$), with p-values $<0.0001$ from Day 20 to study termination at Day 28. Neither rats treated with AB0041 nor rats treated with the Vehicle-A showed any symptoms of musculoskeletal disease during the course of the study.

FIG. 22 shows AB0041 serum levels (serum titers) as measured by ELISA in AB0041-treated rats at days 1, 7, 10, 14, 17, 21, 24, and 28. Mean steady-state levels ranged from 2-4 mg/ml from Day 0 to Day 28, indicating that the rats were exposed to the antibody during the course of the study.

The effects of AB0041 treatment compared to Vehicle-A treatment were assessed by a serum chemistry panel and a histopathological analysis. The serum chemistry panel contained alkaline phosphatase, serum glutamic pyruvic and oxaloacetic transaminases, creatine phosphokinase, albumin, total protein, globulin, total bilirubin, blood urea nitrogen, creatinine, cholesterol, glucose, calcium, phosphorus, bicarbonate, chloride, potassium, and sodium. In both groups, levels of the serum chemistry panel were similar and within normal ranges and similar (data not shown). This indicates that AB0041 treatment did not result in any substantial perturbations to normal homeostasis.

In addition, the histopathological analysis was performed on primary organs from the AB0041 and Vehicle-A groups. Tissues from heart, lung, liver, spleen, kidney, lymph node, stomach, intestine, skin, muscle, and sternum were collected and stained with H&E and examined microscopically. No treatment-related abnormalities were observed in the AB0041 group or the Vehicle-A group (data not shown).

Further, limbs from the AB0041-treated and the Marimastat-treated rats were evaluated for soft tissue changes and for bone and joint changes. Fibrosis and synovitis were observed in the Marimastat group but not in the AB0041 group. In the Marimastat-treated rats, fibrosis ranged from mild to severe and commonly observed in ankles and wrists. Also, synovitis was found in most joints in the Marimastat-treated rats and was mild and characterized by synovial cell proliferation, increased synovial fluid, and inflammatory cell infiltration.

Similar results were observed in H&E-staining of hind knee joints from rats of both groups. No synovitis or fibrosis was observed in the AB0041-treated rats while histopathological evidence of fibroplasia was seen in the Marimastat-treated rats. This finding is consistent with the lack of MSS clinical symptoms in rats in the AB0041-treated group.

Thus, treatment of Lewis rats resulted in multiple symptoms of musculoskeletal disease in all animals beginning at Day 12 after initial treatment, including characteristic signs of MSS, including substantial effects on gait, posture and willingness to move. In contrast, treatment of Lewis rats with AB0041 or with vehicles alone did not induce any clinical, physical, or histological symptoms of MSS. No notable differences or abnormalities were detected in serum chemistry or histological parameters in the AB0041 group or the Vehicle group. The lack of MSS symptoms in the AB0041-treated group was not due to poor drug bioavailability, since serum titer analysis showed that exposure to AB0041 remained high throughout the duration of the study. Contrary to pan-MMP inhibition by Marimastat, specific inhibition of MMP9 by AB0041 did not induce MSS.

Example 10

Anti-MMP9 Antibody in an Orthotopic Xenograft Model

Activities of AB0041 and AB0046 were examined in the orthotopic xenograft mouse CRC model as described in Example 6. The immunohistochemistry analysis of the xenograft model showed that MMP9 was present in stromal inflammatory cells and tumor epithelial cells.

The tumors were grown to ~70 mm$^3$ prior to treatment in Studies I (17 days post-implantation), II (14 days post-implantation), and III (14 days post-implantation). In Study I, fifteen mice per group was treated with either vehicle, control IgG AC-1 (AC-1), AB0041 (h), or a 1:1 mixture of AB0041 and AB0046 (m+h). In the groups of AC-1, h, and m+h, the mice were intraperitoneally administrated with each antibody at 15 mg/kg twice a week. In the m+h group, the mice were pre-administered with AB0046 at 50 mg/kg on the first day of the treatment. In the vehicle group, the mice were intraperitoneally administrated with vehicle twice a week.

In Study II, fifteen mice per group was treated with either vehicle, AC-1, AB0041 (h), a 1:1 mixture of AB0041 and AB0046 (m+h), 5-fluorouracil (5-FU), or a combination of 5-FU and a 1:1 mixture of AB0041 and AB0046 (5-FU+m+h). In the groups of AC-1, h, m+h, and 5-FU+m+h, the mice were intraperitoneally administrated with each antibody at 15 mg/kg twice a week. In the groups of m+h and 5-FU+m+h, the mice were pre-administered with AB0046 at 50 mg/kg on the first day of the treatment. In the groups of 5-FU and 5-FU+m+h, the mice were intraperitoneally administrated with 5-FU at 20 mg/kg twice a week. In the vehicle group, the mice were intraperitoneally administrated with vehicle twice a week.

In Study III, five mice per group with an average of 20% heavier weight compared to that of Study II was treated with either vehicle or a 1:1 mixture of AB0041 and AB0046 (m+h). The mice were administered as described in Study II.

The titer of AB0041 and AB0046 were measured during the studies. Primary tumor sizes and body weights were measured once a week using a caliper and an electronic scale, respectively. Caliper-based size estimates were obtained by measuring the perpendicular minor dimension (W) and major dimension (L) of the palpated tumor. Approximate tumor volume (mm$^3$) was calculated by the formula (W$^2$×L)/2. The non-parametric Mann-Whitney rank sum test was used to determine p values (*=0.05 to 0.01, =0.01 to 0.001, *=<0.001). For RodentMAP analysis, false discovery rate (FDR) analysis was also used to determine q values; the maximum acceptable false discovery rate was set at 0.05. Normalized tumor volume was calculated as follows: an individual mouse's tumor volume at each measurement time point was normalized to its "day 0" tumor volume (i.e. tumor volume at the time of treatment initiation), and these normalized values from each mouse in the group were then averaged to produce a group mean normalized volume for each time point.

At the end of the study when maximum tumor burden was observed, the serum, the primary colon tumor and any organs with metastasis were collected and examined.

Treatment with a 1:1 mixture of antibodies targeting human MMP9 and mouse MMP9 resulted in efficacy similar to those in Example 6 (FIGS. 16 and 23). In Study II, the treatment efficacy in the m+h group was comparable to that in the 5-FU group (FIGS. 23C, 23D). 5-FU is a pyrimidine analog that functions as an antimetabolite and has antineoplastic activity.

In Study I, effects of inhibition of hMMP9 alone were similar to inhibition of inhibiting MMP9 (m+h) in limiting tumor growth (FIG. 24). Tables 4 and 5 summarize Mann-Whitney p values for tumor volume and weight as measured for Studies I and II.

TABLE 4

Mann-Whitney p values for Study II data

| | | Treatment group vs. vehicle/control IgG (Mann-Whitney) | | | |
|---|---|---|---|---|---|
| | | Anti-MMP9 (m + h) | Anti-MMP9 (h) | 5-FU | 5-FU + anti-MMP9 (m + h) |
| Normalized tumor volume, 35 d post-implantation | Vehicle | ** | ** | *** | *** |
| | Control IgG | * | * | *** | *** |
| Final Tumor weight, 36 d post-implantation | Vehicle | * | * | *** | ** |
| | Control IgG | ** | * | *** | ** |

* = 0.05 to 0.01,
** = 0.01 to 0.001,
*** = <0.001

TABLE 5

Mann-Whitney p values for Study I data

| | | Treatment group vs. vehicle/control IgG (p-values; Mann-Whitney | |
|---|---|---|---|
| | | Anti-MMP9 (m + h) | Anti-MMP9 (h) |
| Normalized tumor volume, 34 d post-implantation | Vehicle | * | — |
| | Control IgG | *** | ** |
| Final Tumor weight, 35 d post-implantation | Vehicle | — | * |
| | Control IgG | * | ** |

* = 0.05 to 0.01,
** = 0.01 to 0.001,
*** = <0.001,
— = >0.05

Compared to the control groups, joint inhibition of hMMP9 and mMMP9 reduced the incidence of metastases in Study I. Also, inhibiting only tumor-derived MMP9 was less effective. This result is consistent with a greater role for stromal MMP9 (vs. tumor-derived MMP9) in the invasion processes that result in distal metastases.

In Study III, the difference between normalized tumor volumes in the two groups was significant (FIGS. 23E and 23F). The p-value of the vehicle group vs. the m+h groups was 0.0362 at 36 days post-implantation or 21 days post-treatment.

Immunohistochemical (IHC) analysis of tumors from vehicle-treated mice in Study I demonstrated production of MMP9 by tumor cells at a lower level than MMP9 from stromal sources such as resident macrophages, fibroblasts and endothelial cells. The pattern of MMP9 expression in the xenograph model tumors was similar to that of human CRC; tumor cell expression of MMP9 was heterogeneous, and expression levels could vary widely within a given region of tumor mass.

In Study I, H&E staining of tumor sections and visual assessment for percentage of necrotic tissue did not reveal any significant differences in the extent of necrosis in control vs. anti-MMP9 treated animals. If tumors were binned by final weight into separate groups and then analyzed, there was a slight trend towards increased necrosis in the anti-MMP9-treated group (vs. the control group) for tumors with a final weight less than or equal to 0.4 g (roughly 11% of all control tumors and 7% of all MMP9 antibody-treated tumors), but the difference did not attain statistical significance (p=0.146; Mann-Whitney analysis).

Additional serum analysis was carried out for the study described in Example 6. Serum proteins in a panel of 58 analytes were assessed by RodentMAP. Significance was assessed by the Mann-Whitney test, followed by false-discovery-rate analysis to provide q values. As shown in FIG. 25, C-reactive protein (a marker of inflammation), CXCL2/MIP-2 (a neutrophil attractant and activator), VEGF-A, and CCL7/MCP-3 (a chemokine that activates most leukocyte types and stimulates release of MMP9 from monocytes), T-lymphocytes, and NK cells were significantly reduced in the anti-MMP9 (m+h) group when compared to the vehicle group.

AB0041 (anti-hMMP9 antibody) and AB0046 (anti-mMMP9 antibody) titers were measured in serum collected at the end of Studies I and II. On average, terminal serum concentrations of AB0041 and AB0046 ranged from 100 to 300 µg/mL (data not shown).

The results of these studies demonstrate that targeting MMP9 with a cocktail of human-specific and mouse-specific monoclonal antibodies in a mouse xenograft model reduced growth of the primary tumor in four independent studies, and also reduced the incidence of metastases.

Treatment with anti-human-MMP9 antibody alone yielded tumor growth reduction similar to treatment with both anti-human-MMP9 and anti-mouse-MMP9 antibodies. This suggests that in this xenograft model, tumor-derived human MMP9 (rather than stroma-derived mouse MMP9) is the more predominant driver of tumor cell proliferation. Changes in mouse serum protein levels in mice treated with a cocktail of anti-human MMP9 and anti-mouse MMP9 (as compared to vehicle-treated mice) demonstrated that the angiogenic factor VEGF and the inflammatory factors C-reactive protein, CXCL2, and CCL7 were significantly reduced in anti-MMP9-treated mice as compared to vehicle-treated mice, consistent with a role of MMP9 in inflammation and angiogenesis. Also, tumor epithelial-derived MMP9 is involved in primary tumor outgrowth and that targeting of stromal MMP9 increases efficacy to incidence of metastases.

Example 11

Therapeutic Treatments Using Anti-MMP9 Antibodies

AB0045 is used in treating patients having advanced pancreatic or esophagogastric adenocarcinoma, non-small cell lung cancer, ulcerative colitis, Crohn's disease, or rheumatoid arthritis. The patients are administered the antibody intravenously at a dosage of 100, 200, 400, 600, 1200, or 1800 mg/Kg body weight, at the interval of one, two or three weeks. The appropriate dosage is made with 0.9% sodium chloride. The patients receive AB0045 as monotherapy or as part of a combination therapy with other therapeutic agents.

For treating UC, Crohn's disease, or rheumatoid arthritis, AB0045 is administered alone or with other immunotherapeutic agents, including antibodies against LOXL2 (lysyl oxidase-like 2) and/or DDR1 (discoidin domain receptor 1).

For pancreatic adenocarcinoma, the antibody is administered alone at the two-week interval or with the 28-day cycle chemotherapy of gemcitabine and/or nab-paclitaxel.

For esophagogastric adenocarcinoma, the antibody is administered alone at the two-week interval or with the 28-day cycle chemotherapy of mFOLFOX6 that is administered in a 28-day cycle.

For non-small cell lung cancer, the antibody is administered alone at the three-week interval or with the 21-day cycle chemotherapy of carboplatin and paclitaxel or with pemetrexed and/or bevacizumab.

In the combination treatments, the chemotherapy is administered with the known dosage and procedure.

The dosage of MMP9 antibody can be adjusted and administered at 133, 267, 400, 600 or 1200 mg/Kg body weight. After each therapeutic cycle, the patients are monitored for the levels of MMP9 antibodies, MMP9, or other suitable biomarkers.

Example 12

Anti-MMP9 Antibody in Rheumatoid Arthritis Model

Example 7 showed the efficacies of AB0041 in treating rheumatoid arthritis in rats and mice. This example provides additional characterizations of the animals in example 7 that were treated with either vehicle, AB0041 (in the rat model) or AB0046 (in the mouse model) at 2, 10, or 50 mg/Kg, Enbrel at 10 mg/Kg, or methotrexate (MTX) at 0.5 mg/Kg.

In addition to clinical scoring in Table 6 that was conducted in example 7, paw swelling, ankle diameter and body weights of the treated animals were measured. The measurements were conducted once a week before randomization and three times a week thereafter. As shown in FIGS. 26 (rats) and 29 (mice), the administration of AB0041 in rats and AB0046 in mice at all doses resulted in significant reversal/mitigation of qualitative and quantitative measurements of clinical disease. Results also showed that treatment with AB0041 or AB0046, at 50 mg/kg, reduced all measures of soft tissue diseases, joint damage and destruction. The efficacy of the anti-MMP9 antibodies was comparable to that observed with Enbrel and methotrexate (MTX).

TABLE 6

Scale and Criteria for Clinical Scoring of Paws

| Scale[a] | Clinical Signs |
| --- | --- |
| 0.0 | No evidence of erythema or swelling |
| 0.5 | Minor erythema or swelling confined to one small area |
| 1.0 | Minor erythema or swelling of the ankle or wrist |
| 1.5 | Moderate erythema and mild swelling confined to ankle or wrist |
| 2.0 | Moderate erythema and mild swelling confined to half of the paw |

TABLE 6-continued

Scale and Criteria for Clinical Scoring of Paws

| Scale[a] | Clinical Signs |
|---|---|
| 2.5 | Moderate erythema and mild swelling extending more than half of the paw |
| 3.0 | Moderate erythema and moderate swelling extending more than half of the paw |
| 3.5 | Severe erythema and swelling extending more than ¾ of the paw |
| 4.0 | Severe erythema and swelling occurring throughout the paw |

[a]Each paw received its own score and these values were totaled for each animal for a theoretical maximum of 16

In addition, hind limbs were examined microscopically for soft-tissue changes (edema, tissue/vessel necrosis, inflammatory cell infiltration, and fibroplasias) and cartilage and bone changes (cartilage erosion, bone erosion, periosteal bone formation, synovitis, pannus formation, and joint destruction). A standard severity score was used: 0=no significant change, 1=minimal, 2=mild, 3=moderate and 4=severe. The severity scores were based on global changes in each limb.

Immunohistochemistry (IHC) analysis was performed to assess levels of MMP9, TNF-alpha, CD68, and Cathepsin K. Scoring of anti-TNF-alpha staining and anti-CD68 was done on a qualitative scale ranging from 0-4, where 0 was the level in non-diseased joints and 4 was the highest expression observed in vehicle-treated limbs. For anti-TNF-alpha scoring, the entire region of the limb anterior to the tarsal-metatarsal joint was scored. Anti-CD68 staining was evaluated using 3-4 images per limb of synovial membranes in the joints formed by the talus bone, with the scores of each membrane averaged and the value assigned as the overall inflammation score. Results from IHC showed MMP9 expression in regions of active diseased areas including fronts of cartilage damage and bone erosion as well as in pannus tissue. Also, MMP9-expressing cells were identified as osteoclasts and cells of the monocyte/macrophage lineage.

In rats treated with 50 mg/kg AB0041, CD68 and TNF-alpha was quantified. Results by IHC revealed a significant reduction in both CD68 and TNF-alpha in this group compared to the vehicle treated group (FIG. 27). The results indicate a reduction in bone and cartilage degrading cell types (osteoclasts and cells of the monocyte/macrophage lineage) and a systemic mediator of inflammation and arthritis (TNF-alpha).

Further, serum panel analyses of terminal serum samples were characterized using ELISA. The results summarized in FIGS. 18A and 28 (rats) and 18B and 19B (mice) showed a consistent reduction in mediators of inflammation and disease progression. As shown in FIG. 28, AB0041 treatment in rats resulted in a statistically significant reduction of endogenous MMP9 inhibitor tissue inhibitor of metalloproteinase (TIMP)-1, the leukocyte mitogen granulocyte-macrophage colony stimulating-factor (GM-CSF), neutrophil attractant and activator macrophage inflammatory protein (MIP)-2, natural killer cell and monocyte chemottractant MIP-1β, hematopoietic stem cell differentiator macrophage colony-stimulating factor (M-CSF)-1, IL-6 family cytokine oncostatin M (OSM), chemoattractants C-X-C motif chemokine (CXCL)10 and monocyte chemoattractant protein (MCP)-5, natural killer and T cell activator IL-12p70, and immune system modulators interferon (INF)-γ, IL-12, and IL-7. No reduction of serum markers was observed in the Enbrel-treated rats, while methotrexate treatment resulted in a consistent increase in these markers. As shown in FIG. 19B, AB0046 treatment in mice resulted in a statistically significant reduction of neutrophil attractants and/or activators KC/GRO, MIP-2, and GCP-2; NK and T cell attractant lymphotactin; monocyte chemoattractants MCP-1 and MCP-3; lymphocyte and dendritic cell chemoattractant CXCL-10; IL-6-like cytokine OSM; granulocyte activators MIP-1β and MIP-1γ; and apolipoprotein (Apo) A-1. AB0046 titers were measured in terminal serum samples. Additionally, the dosing regimens of 10 and 50 mg/kg resulted in measurable drug levels.

These data show that treatment with an inhibitory anti-MMP9 monoclonal antibody in a rat CIA treatment model resulted in mitigation and reversal of clinical observations and objective measurements of joint inflammation, reduction of the histopathological manifestations of joint inflammation and destruction, and decrease in disease mediating cell types and factors. The therapeutic effect was comparable to reference compounds Enbrel and methotrexate. A broad systemic anti-inflammatory effect was observed with the anti-MMP9 treatment but not with administration of either Enbrel or methotrexate.

Example 13

Expression of MMP9 in Human Tumors

Protein and mRNA levels of MMP9 and MMP2 were examined by immunohistochemistry (IHC) and by chromogenic in situ hybridization. Tissues from human lung squamous cell carcinoma, lung adenocarcinoma, gastric adenocarcinoma, colorectal adenocarcinoma, pancreatic adenocarcinoma, hepatocellular carcinoma, and squamous cell carcinoma of head & neck were characterized.

In IHC analysis, the samples were stained using two distinct MMP9-specific antibodies: the polyclonal antibody Sigma HPA001238 and the monoclonal antibody Abcam (ab76003). The percentage of MMP9-positive tumor epithelia for a given tumor sample were scored by visual assessment. Specificity of the anti-MMP9 antibodies used for IHC analysis was evaluated by testing against a panel of MMPs in an immunoblot. Neither antibody displayed any notable cross-reactivity against any tested MMP other than MMP9.

In all tumors surveyed, MMP9 immunoreactivity was seen in subsets of histiocytes (tissue-resident macrophages), neutrophils, endothelial cells, and fibroblasts, as well as in non-neoplastic epithelia and tumor epithelia. Secreted MMP9 protein was also found in the extracellular matrix, and was generally associated with inflammatory infiltrates within the tumors. The detection of MMP9 expression was often associated with necrotic regions across all cancer samples.

MMP2 signal was detected in subsets of histiocytes dispersed throughout tumors and present in reactive smooth muscle of the tumor microenvironment, endothelial cells, smooth muscle of the arterioles, and non-neoplastic epithelia. Most tumor epithelia were positive for MMP2 but with more diffused staining patterns than observed for MMP9. MMP2 expression was more widespread across the tissue (neoplastic and non-neoplastic) compared to the more heterogeneous expression of MMP9.

FIG. 30 summarizes the percentage of MMP9-positive tumor epithelia observed in this study. Stromal MMP9 positivity was also present in all samples but not scored. The percentage of samples for a given tumor type that fell into each "positivity" category is shown on the x-axis of FIG. 30. The analysis showed expression across all tumor types and patterns characteristic of each cancer type with respect to extent and source of MMP9-positivity.

CISH analysis detected that MMP9 mRNA in tumor epithelial cells by subsets of immune cells (particularly macrophages and neutrophils) and other stromal constituents such as endothelial cells. Results of CISH analysis showed that MMP9 mRNA was present in macrophages/histiocytes, neutrophils, and tumor epithelia cells. Also, MMP9 mRNA expression varied within and among tumor types. In all tumors analyzed, cell types expressing MMP9 mRNA included subsets of histiocytes, neutrophils, and tumor cells. Similar to the heterogeneity in the IHC analysis, the level of MMP9 mRNA expression varied.

FIG. 31 summarizes CISH analysis of the tumor epithelial-associated MMP9 mRNA. The percentage of tissue samples for a given tumor type that fell into each "positivity" category is shown on the x-axis. The analysis revealed expression across all tumor types and patterns characteristic of each cancer type with respect to extent and source of MMP9-positivity.

Results from CISH and IHC analyses show the expression of MMP9 in tumor epithelia. In some samples, CISH detected MMP9 mRNA where no protein signal was detected. As tumor-derived MMP9 is frequently less abundant than inflammatory cell-derived MMP9, CISH analysis is suitable to detect MMP9 expression in samples having high levels of inflammatory cell-derived MMP9 that obscure the IHC signal of tumor epithelia-derived MMP9.

---

What is claimed is:

1. A method of treating an autoimmune or inflammatory disease or condition in a subject, comprising administering to the subject a composition comprising an antibody or an antigen binding fragment thereof that binds to human Matrix Metalloprotease 9 (MMP9), wherein the antibody or the antigen binding fragment thereof that binds to human MMP9 comprises a heavy chain variable domain ($V_H$) comprising three complementarity determining regions (CDRs) comprising the amino acid sequences set forth in SEQ ID NOs: 13, 14, and 15 and a light chain variable domain ($V_L$) comprising three CDRs comprising the amino acid sequences set forth in SEQ ID NOs: 16, 17, and 18, and wherein the autoimmune or inflammatory disease or condition is rheumatoid arthritis.

2. The method of claim 1, wherein the heavy chain variable domain ($V_H$) comprises an amino acid sequence set forth in SEQ ID NO: 7.

3. The method of claim 1, wherein the light chain variable domain (V$_L$) comprises an amino acid sequence set forth in SEQ ID NO: 12.

4. The method of claim 1, wherein the composition inhibits the enzymatic activity of MMP9.

5. The method of claim 4, wherein the inhibition of the enzymatic activity is non-competitive.

6. The method of claim 1, wherein the antibody or antigen binding fragment thereof that hinds to human MMP9 is administered at a dose of about 1 mg/kg to about 28 mg/kg.

7. The method of claim 1, wherein the antibody or antigen binding fragment thereof that binds to human MMP9 is administered at a dose of about 10 ng/kg to about 100 mg/kg body weight per day.

8. The method of claim 7, wherein the antibody or antigen binding fragment thereof that binds to human MMP9 is administered at a dose of about 1 μg/kg to 50 mg/kg, about 100 μg/kg to 20 mg/kg, about 500 μg/kg to 10 mg/kg, or about 1 mg/kg to 10 mg/kg body weight per day.

9. The method of claim 1, wherein the composition is administered once every week, once every two weeks, or once every three weeks.

10. The method of claim 1, wherein the composition is administered intravenously, intra-arterially, intradermally, intramuscularly, subcutaneously, or orally.

11. The method of claim 1, wherein the composition further comprises one or more therapeutic agents selected from the group consisting of: an anti-inflammatory agent, an immunotherapeutic agent, or a combination thereof.

12. The method of claim 10, wherein the composition is administered intravenously.

13. The method of claim 10, wherein the composition is administered subcutaneously.

14. The method of claim 1, wherein the heavy chain variable domain (V$_H$) comprises an amino acid sequence set forth in SEQ ID NO: 7, and the light chain variable domain (V$_L$) comprises an amino acid sequence set forth in SEQ ID NO: 12.

15. The method of claim 14, wherein the composition further comprises one or more therapeutic agents selected from the group consisting of: an anti-inflammatory agent, an immunotherapeutic agent, or a combination thereof.

16. The method of claim 14, wherein the subject is human.

17. The method of claim 14, wherein the composition is administered once every week, once every two weeks, or once every three weeks.

18. The method of claim 14, wherein the composition is administered intravenously, intra-arterially, intradermally, intramuscularly, subcutaneously, or orally.

19. The method of claim 18, wherein the composition is administered intravenously.

20. The method of claim 18, wherein the composition is administered subcutaneously.

* * * * *

SEQUENCE LISTING

```
<160> NUMBER OF SEQ ID NOS: 50

<210> SEQ ID NO 1
<211> LENGTH: 470
<212> TYPE: PRT
<213> ORGANISM: Mus musculus
<220> FEATURE:
<221> NAME/KEY: CHAIN
<222> LOCATION: (1)...(470)
<223> OTHER INFORMATION: AB0041 heavy chain
<220> FEATURE:
<221> NAME/KEY: PEPTIDE
<222> LOCATION: (1)...(19)
<223> OTHER INFORMATION: signal peptide
<220> FEATURE:
<221> NAME/KEY: misc_feature
<222> LOCATION: (135)...(470)
<223> OTHER INFORMATION: IgG2b constant region

<400> SEQUENCE: 1

Met Ala Val Leu Val Leu Phe Leu Cys Leu Val Ala Phe Pro Ser Cys
  1               5                  10                  15

Val Leu Ser Gln Val Gln Leu Lys Glu Ser Gly Pro Gly Leu Val Ala
             20                  25                  30

Pro Ser Gln Ser Leu Ser Ile Thr Cys Thr Val Ser Gly Phe Ser Leu
         35                  40                  45

Leu Ser Tyr Gly Val His Trp Val Arg Gln Pro Pro Gly Lys Gly Leu
     50                  55                  60

Glu Trp Leu Gly Val Ile Trp Thr Gly Gly Thr Thr Asn Tyr Asn Ser
 65                  70                  75                  80

Ala Leu Met Ser Arg Leu Ser Ile Ser Lys Asp Asp Ser Lys Ser Gln
             85                  90                  95

Val Phe Leu Lys Met Asn Ser Leu Gln Thr Asp Asp Thr Ala Ile Tyr
            100                 105                 110

Tyr Cys Ala Arg Tyr Tyr Tyr Gly Met Asp Tyr Trp Gly Gln Gly Thr
        115                 120                 125

Ser Val Thr Val Ser Ser Ala Lys Thr Thr Pro Pro Ser Val Tyr Pro
    130                 135                 140

Leu Ala Pro Gly Cys Gly Asp Thr Thr Gly Ser Ser Val Thr Leu Gly
145                 150                 155                 160

Cys Leu Val Lys Gly Tyr Phe Pro Glu Ser Val Thr Val Thr Trp Asn
                165                 170                 175

Ser Gly Ser Leu Ser Ser Ser Val His Thr Phe Pro Ala Leu Leu Gln
            180                 185                 190

Ser Gly Leu Tyr Thr Met Ser Ser Ser Val Thr Val Pro Ser Ser Thr
```

```
                195                 200                 205
Trp Pro Ser Gln Thr Val Thr Cys Ser Val Ala His Pro Ala Ser Ser
210                 215                 220

Thr Thr Val Asp Lys Lys Leu Glu Pro Ser Gly Pro Ile Ser Thr Ile
225                 230                 235                 240

Asn Pro Cys Pro Pro Cys Lys Glu Cys His Lys Cys Pro Ala Pro Asn
                245                 250                 255

Leu Glu Gly Gly Pro Ser Val Phe Ile Phe Pro Pro Asn Ile Lys Asp
                260                 265                 270

Val Leu Met Ile Ser Leu Thr Pro Lys Val Thr Cys Val Val Val Asp
                275                 280                 285

Val Ser Glu Asp Asp Pro Asp Val Arg Ile Ser Trp Phe Val Asn Asn
290                 295                 300

Val Glu Val His Thr Ala Gln Thr Gln Thr His Arg Glu Asp Tyr Asn
305                 310                 315                 320

Ser Thr Ile Arg Val Val Ser Ala Leu Pro Ile Gln His Gln Asp Trp
                325                 330                 335

Met Ser Gly Lys Glu Phe Lys Cys Lys Val Asn Asn Lys Asp Leu Pro
                340                 345                 350

Ser Pro Ile Glu Arg Thr Ile Ser Lys Ile Lys Gly Leu Val Arg Ala
                355                 360                 365

Pro Gln Val Tyr Ile Leu Pro Pro Ala Glu Gln Leu Ser Arg Lys
                370                 375                 380

Asp Val Ser Leu Thr Cys Leu Val Val Gly Phe Asn Pro Gly Asp Ile
385                 390                 395                 400

Ser Val Glu Trp Thr Ser Asn Gly His Thr Glu Glu Asn Tyr Lys Asp
                405                 410                 415

Thr Ala Pro Val Leu Asp Ser Asp Gly Ser Tyr Phe Ile Tyr Ser Lys
                420                 425                 430

Leu Asp Ile Lys Thr Ser Lys Trp Glu Lys Thr Asp Ser Phe Ser Cys
                435                 440                 445

Asn Val Arg His Glu Gly Leu Lys Asn Tyr Tyr Leu Lys Lys Thr Ile
    450                 455                 460

Ser Arg Ser Pro Gly Lys
465                 470

<210> SEQ ID NO 2
<211> LENGTH: 234
<212> TYPE: PRT
<213> ORGANISM: Mus musculus
<220> FEATURE:
<221> NAME/KEY: CHAIN
<222> LOCATION: (1)...(234)
<223> OTHER INFORMATION: AB0041 light chain
<220> FEATURE:
<221> NAME/KEY: PEPTIDE
<222> LOCATION: (1)...(20)
<223> OTHER INFORMATION: signal peptide
<220> FEATURE:
<221> NAME/KEY: misc_feature
<222> LOCATION: (128)...(234)
<223> OTHER INFORMATION: kappa constant region

<400> SEQUENCE: 2

Met Glu Ser Gln Ile Gln Val Phe Val Phe Val Phe Leu Trp Leu Ser
1                 5                   10                  15

Gly Val Asp Gly Asp Ile Val Met Thr Gln Ser His Lys Phe Met Ser
                20                  25                  30
```

```
Thr Ser Val Gly Asp Arg Val Ser Ile Thr Cys Lys Ala Ser Gln Asp
        35                  40                  45

Val Arg Asn Thr Val Ala Trp Tyr Gln Gln Lys Thr Gly Gln Ser Pro
 50                  55                  60

Lys Leu Leu Ile Tyr Ser Ser Tyr Arg Asn Thr Gly Val Pro Asp
 65                  70                  75                  80

Arg Phe Thr Gly Ser Gly Ser Gly Thr Asp Phe Thr Phe Thr Ile Ser
                     85                  90                  95

Ser Val Gln Ala Glu Asp Leu Ala Val Tyr Phe Cys Gln His Tyr
                100                 105                 110

Ile Thr Pro Tyr Thr Phe Gly Gly Thr Lys Leu Glu Ile Lys Arg
                115                 120                 125

Ala Asp Ala Ala Pro Thr Val Ser Ile Phe Pro Pro Ser Ser Glu Gln
130                 135                 140

Leu Thr Ser Gly Gly Ala Ser Val Val Cys Phe Leu Asn Asn Phe Tyr
145                 150                 155                 160

Pro Lys Asp Ile Asn Val Lys Trp Lys Ile Asp Gly Ser Glu Arg Gln
                165                 170                 175

Asn Gly Val Leu Asn Ser Trp Thr Asp Gln Asp Ser Lys Asp Ser Thr
                180                 185                 190

Tyr Ser Met Ser Ser Thr Leu Thr Leu Thr Lys Asp Glu Tyr Glu Arg
                195                 200                 205

His Asn Ser Tyr Thr Cys Glu Ala Thr His Lys Thr Ser Thr Ser Pro
                210                 215                 220

Ile Val Lys Ser Phe Asn Arg Asn Glu Cys
225                 230

<210> SEQ ID NO 3
<211> LENGTH: 115
<212> TYPE: PRT
<213> ORGANISM: Mus musculus
<220> FEATURE:
<221> NAME/KEY: CHAIN
<222> LOCATION: (1)...(115)
<223> OTHER INFORMATION: variable region of the IgG2b heavy chain of
      AB0041
<220> FEATURE:
<221> NAME/KEY: misc_feature
<222> LOCATION: (26)...(35)
<223> OTHER INFORMATION: complementarity-determining region (CDR)
<220> FEATURE:
<221> NAME/KEY: misc_feature
<222> LOCATION: (50)...(65)
<223> OTHER INFORMATION: complementarity-determining region (CDR)
<220> FEATURE:
<221> NAME/KEY: misc_feature
<222> LOCATION: (98)...(104)
<223> OTHER INFORMATION: complementarity-determining region (CDR)

<400> SEQUENCE: 3

Gln Val Gln Leu Lys Glu Ser Gly Pro Gly Leu Val Ala Pro Ser Gln
 1                   5                  10                  15

Ser Leu Ser Ile Thr Cys Thr Val Ser Gly Phe Ser Leu Leu Ser Tyr
                 20                  25                  30

Gly Val His Trp Val Arg Gln Pro Pro Gly Lys Gly Leu Glu Trp Leu
             35                  40                  45

Gly Val Ile Trp Thr Gly Gly Thr Thr Asn Tyr Asn Ser Ala Leu Met
         50                  55                  60

Ser Arg Leu Ser Ile Ser Lys Asp Asp Ser Lys Ser Gln Val Phe Leu
 65                  70                  75                  80
```

```
Lys Met Asn Ser Leu Gln Thr Asp Asp Thr Ala Ile Tyr Tyr Cys Ala
            85                  90                  95

Arg Tyr Tyr Tyr Gly Met Asp Tyr Trp Gly Gln Gly Thr Ser Val Thr
            100                 105                 110

Val Ser Ser
        115

<210> SEQ ID NO 4
<211> LENGTH: 107
<212> TYPE: PRT
<213> ORGANISM: Mus musculus
<220> FEATURE:
<221> NAME/KEY: CHAIN
<222> LOCATION: (1)...(107)
<223> OTHER INFORMATION: variable region of the kappa light chain of
      AB0041
<220> FEATURE:
<221> NAME/KEY: misc_feature
<222> LOCATION: (24)...(34)
<223> OTHER INFORMATION: complementarity-determining region (CDR)
<220> FEATURE:
<221> NAME/KEY: misc_feature
<222> LOCATION: (50)...(56)
<223> OTHER INFORMATION: complementarity-determining region (CDR)
<220> FEATURE:
<221> NAME/KEY: misc_feature
<222> LOCATION: (89)...(97)
<223> OTHER INFORMATION: complementarity-determining region (CDR)

<400> SEQUENCE: 4

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Arg Asn Thr
            20                  25                  30

Val Ala Trp Tyr Gln Gln Lys Thr Gly Gln Ser Pro Lys Leu Leu Ile
        35                  40                  45

Tyr Ser Ser Ser Tyr Arg Asn Thr Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Phe Cys Gln Gln His Tyr Ile Thr Pro Tyr
                85                  90                  95

Thr Phe Gly Gly Gly Thr Lys Leu Glu Ile Lys
            100                 105

<210> SEQ ID NO 5
<211> LENGTH: 115
<212> TYPE: PRT
<213> ORGANISM: Artificial Sequence
<220> FEATURE:
<223> OTHER INFORMATION: synthetic construct
<220> FEATURE:
<221> NAME/KEY: VARIANT
<222> LOCATION: (1)...(115)
<223> OTHER INFORMATION: VH1 heavy chain variant

<400> SEQUENCE: 5

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Tyr
            20                  25                  30

Gly Val His Trp Val Arg Gln Pro Pro Gly Lys Gly Leu Glu Trp Leu
        35                  40                  45

Gly Val Ile Trp Thr Gly Gly Thr Thr Asn Tyr Asn Ser Ala Leu Met
```

```
                     50                  55                  60
Ser Arg Leu Thr Ile Ser Lys Asp Asp Ser Lys Ser Thr Val Tyr Leu
 65                  70                  75                  80

Lys Met Asn Ser Leu Lys Thr Glu Asp Thr Ala Ile Tyr Tyr Cys Ala
                 85                  90                  95

Arg Tyr Tyr Tyr Gly Met Asp Tyr Trp Gly Gln Gly Thr Ser Val Thr
                100                 105                 110

Val Ser Ser
        115

<210> SEQ ID NO 6
<211> LENGTH: 115
<212> TYPE: PRT
<213> ORGANISM: Artificial Sequence
<220> FEATURE:
<223> OTHER INFORMATION: synthetic construct
<220> FEATURE:
<221> NAME/KEY: VARIANT
<222> LOCATION: (1)...(115)
<223> OTHER INFORMATION: VH2 heavy chain variant

<400> SEQUENCE: 6

Gln Val Gln Leu Gln Glu Ser Gly Pro Gly Leu Val Lys Pro Ser Glu
  1               5                  10                  15

Thr Leu Ser Leu Thr Cys Thr Val Ser Gly Phe Ser Leu Leu Ser Tyr
                 20                  25                  30

Gly Val His Trp Val Arg Gln Pro Pro Gly Lys Gly Leu Glu Trp Leu
            35                  40                  45

Gly Val Ile Trp Thr Gly Gly Thr Thr Asn Tyr Asn Ser Ala Leu Met
 50                  55                  60

Ser Arg Leu Thr Ile Ser Lys Asp Asp Ser Lys Asn Thr Val Tyr Leu
 65                  70                  75                  80

Lys Met Asn Ser Leu Lys Thr Glu Asp Thr Ala Ile Tyr Tyr Cys Ala
                 85                  90                  95

Arg Tyr Tyr Tyr Gly Met Asp Tyr Trp Gly Gln Gly Thr Leu Val Thr
                100                 105                 110

Val Ser Ser
        115

<210> SEQ ID NO 7
<211> LENGTH: 115
<212> TYPE: PRT
<213> ORGANISM: Artificial Sequence
<220> FEATURE:
<223> OTHER INFORMATION: synthetic construct
<220> FEATURE:
<221> NAME/KEY: VARIANT
<222> LOCATION: (1)...(115)
<223> OTHER INFORMATION: VH3 heavy chain variant

<400> SEQUENCE: 7

Gln Val Gln Leu Gln Glu Ser Gly Pro Gly Leu Val Lys Pro Ser Glu
  1               5                  10                  15

Thr Leu Ser Leu Thr Cys Thr Val Ser Gly Phe Ser Leu Leu Ser Tyr
                 20                  25                  30

Gly Val His Trp Val Arg Gln Pro Pro Gly Lys Gly Leu Glu Trp Leu
            35                  40                  45

Gly Val Ile Trp Thr Gly Gly Thr Thr Asn Tyr Asn Ser Ala Leu Met
 50                  55                  60

Ser Arg Phe Thr Ile Ser Lys Asp Asp Ser Lys Asn Thr Val Tyr Leu
```

```
                65                  70                  75                  80
Lys Met Asn Ser Leu Lys Thr Glu Asp Thr Ala Ile Tyr Tyr Cys Ala
                    85                  90                  95

Arg Tyr Tyr Tyr Gly Met Asp Tyr Trp Gly Gln Gly Thr Leu Val Thr
                100                 105                 110

Val Ser Ser
        115

<210> SEQ ID NO 8
<211> LENGTH: 115
<212> TYPE: PRT
<213> ORGANISM: Artificial Sequence
<220> FEATURE:
<223> OTHER INFORMATION: synthetic construct
<220> FEATURE:
<221> NAME/KEY: VARIANT
<222> LOCATION: (1)...(115)
<223> OTHER INFORMATION: VH4 heavy chain variant

<400> SEQUENCE: 8

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Leu Ser Tyr
                20                  25                  30

Gly Val His Trp Val Arg Gln Pro Pro Gly Lys Gly Leu Glu Trp Leu
            35                  40                  45

Gly Val Ile Trp Thr Gly Gly Thr Thr Asn Tyr Asn Ser Ala Leu Met
        50                  55                  60

Ser Arg Phe Thr Ile Ser Lys Asp Asp Ser Lys Asn Thr Leu Tyr Leu
65                  70                  75                  80

Lys Met Asn Ser Leu Lys Thr Glu Asp Thr Ala Ile Tyr Tyr Cys Ala
                    85                  90                  95

Arg Tyr Tyr Tyr Gly Met Asp Tyr Trp Gly Gln Gly Thr Leu Val Thr
                100                 105                 110

Val Ser Ser
        115

<210> SEQ ID NO 9
<211> LENGTH: 107
<212> TYPE: PRT
<213> ORGANISM: Artificial Sequence
<220> FEATURE:
<223> OTHER INFORMATION: synthetic construct
<220> FEATURE:
<221> NAME/KEY: VARIANT
<222> LOCATION: (1)...(107)
<223> OTHER INFORMATION: Vk1 light chain variant

<400> SEQUENCE: 9

Asp Ile Val Met Thr Gln Ser Pro Ser Phe Leu Ser Ala Ser Val Gly
1               5                   10                  15

Asp Arg Val Thr Ile Thr Cys Lys Ala Ser Gln Asp Val Arg Asn Thr
                20                  25                  30

Val Ala Trp Tyr Gln Gln Lys Thr Gly Lys Ala Pro Lys Leu Leu Ile
            35                  40                  45

Tyr Ser Ser Ser Tyr Arg Asn Thr Gly Val Pro Asp Arg Phe Thr Gly
        50                  55                  60

Ser Gly Ser Gly Thr Asp Phe Thr Leu Thr Ile Ser Ser Leu Gln Ala
65                  70                  75                  80

Glu Asp Val Ala Val Tyr Phe Cys Gln Gln His Tyr Ile Thr Pro Tyr
```

```
                    85                  90                  95

Thr Phe Gly Gly Gly Thr Lys Val Glu Ile Lys
                100                 105

<210> SEQ ID NO 10
<211> LENGTH: 107
<212> TYPE: PRT
<213> ORGANISM: Artificial Sequence
<220> FEATURE:
<223> OTHER INFORMATION: synthetic construct
<220> FEATURE:
<221> NAME/KEY: VARIANT
<222> LOCATION: (1)...(107)
<223> OTHER INFORMATION: Vk2 light chain variant

<400> SEQUENCE: 10

Asp Ile Val Met Thr Gln Ser Pro Ser Ser Leu Ser Ala Ser Val Gly
 1               5                  10                  15

Asp Arg Val Thr Ile Thr Cys Lys Ala Ser Gln Asp Val Arg Asn Thr
                20                  25                  30

Val Ala Trp Tyr Gln Gln Lys Pro Gly Lys Ala Pro Lys Leu Leu Ile
             35                  40                  45

Tyr Ser Ser Ser Tyr Arg Asn Thr Gly Val Pro Asp Arg Phe Thr Gly
 50                  55                  60

Ser Gly Ser Gly Thr Asp Phe Thr Leu Thr Ile Ser Ser Leu Gln Ala
65                   70                  75                  80

Glu Asp Val Ala Val Tyr Phe Cys Gln Gln His Tyr Ile Thr Pro Tyr
                 85                  90                  95

Thr Phe Gly Gly Gly Thr Lys Val Glu Ile Lys
                100                 105

<210> SEQ ID NO 11
<211> LENGTH: 107
<212> TYPE: PRT
<213> ORGANISM: Artificial Sequence
<220> FEATURE:
<223> OTHER INFORMATION: synthetic construct
<220> FEATURE:
<221> NAME/KEY: VARIANT
<222> LOCATION: (1)...(107)
<223> OTHER INFORMATION: Vk3 light chain variant

<400> SEQUENCE: 11

Asp Ile Gln Met Thr Gln Ser Pro Ser Ser Leu Ser Ala Ser Val Gly
 1               5                  10                  15

Asp Arg Val Thr Ile Thr Cys Lys Ala Ser Gln Asp Val Arg Asn Thr
                20                  25                  30

Val Ala Trp Tyr Gln Gln Lys Pro Gly Lys Ala Pro Lys Leu Leu Ile
             35                  40                  45

Tyr Ser Ser Ser Tyr Arg Asn Thr Gly Val Pro Asp Arg Phe Ser Gly
 50                  55                  60

Ser Gly Ser Gly Thr Asp Phe Thr Leu Thr Ile Ser Ser Leu Gln Ala
65                   70                  75                  80

Glu Asp Val Ala Val Tyr Phe Cys Gln Gln His Tyr Ile Thr Pro Tyr
                 85                  90                  95

Thr Phe Gly Gly Gly Thr Lys Val Glu Ile Lys
                100                 105

<210> SEQ ID NO 12
<211> LENGTH: 107
<212> TYPE: PRT
```

<213> ORGANISM: Artificial Sequence
<220> FEATURE:
<223> OTHER INFORMATION: synthetic construct
<220> FEATURE:
<221> NAME/KEY: VARIANT
<222> LOCATION: (1)...(107)
<223> OTHER INFORMATION: Vk4 light chain variant

<400> SEQUENCE: 12

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Arg Asn Thr
            20                  25                  30

Val Ala Trp Tyr Gln Gln Lys Pro Gly Lys Ala Pro Lys Leu Leu Ile
        35                  40                  45

Tyr Ser Ser Ser Tyr Arg Asn Thr Gly Val Pro Asp Arg Phe Ser Gly
    50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys Gln Gln His Tyr Ile Thr Pro Tyr
                85                  90                  95

Thr Phe Gly Gly Gly Thr Lys Val Glu Ile Lys
            100                 105
```

<210> SEQ ID NO 13
<211> LENGTH: 10
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)...(10)
<223> OTHER INFORMATION: complementarity-determining region (CDR1) of
      heavy chain of anti-MMP9 antibody

<400> SEQUENCE: 13

```
Gly Phe Ser Leu Leu Ser Tyr Gly Val His
1               5                   10
```

<210> SEQ ID NO 14
<211> LENGTH: 16
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)...(16)
<223> OTHER INFORMATION: complementarity-determining region (CDR2) of
      heavy chain of anti-MMP9 antibody

<400> SEQUENCE: 14

```
Val Ile Trp Thr Gly Gly Thr Thr Asn Tyr Asn Ser Ala Leu Met Ser
1               5                   10                  15
```

<210> SEQ ID NO 15
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)...(7)
<223> OTHER INFORMATION: complementarity-determining region (CDR3) of
      heavy chain of anti-MMP9 antibody -continued

<400> SEQUENCE: 15

Tyr Tyr Tyr Gly Met Asp Tyr
1               5

<210> SEQ ID NO 16
<211> LENGTH: 11
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)...(11)
<223> OTHER INFORMATION: complementarity-determining region (CDR1) of
      light chain of anti-MMP9 antibody

<400> SEQUENCE: 16

Lys Ala Ser Gln Asp Val Arg Asn Thr Val Ala
1               5                   10

<210> SEQ ID NO 17
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)...(7)
<223> OTHER INFORMATION: complementarity-determining region (CDR2) of
      light chain of anti-MMP9 antibody

<400> SEQUENCE: 17

Ser Ser Ser Tyr Arg Asn Thr
1               5

<210> SEQ ID NO 18
<211> LENGTH: 9
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)...(9)
<223> OTHER INFORMATION: complementarity-determining region (CDR3) of
      light chain of anti-MMP9 antibody

<400> SEQUENCE: 18

Gln Gln His Tyr Ile Thr Pro Tyr Thr
1               5

<210> SEQ ID NO 19
<211> LENGTH: 345
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)...(345)
<223> OTHER INFORMATION: nucleotide sequence encoding VH1 heavy chain
      amino acid sequence

<400> SEQUENCE: 19
caggtgcagc tgcaggaatc cggccctggc ctggtcaagc cctccgagac actgtccctg     60
acctgcaccg tgtccggctt ctccctgctg tcctacggcg tgcactgggt ccgacagcct    120

```
ccagggaagg gcctggaatg gctgggcgtg atctggaccg gcggcaccac caactacaac      180
tccgccctga tgtcccggct gaccatctcc aaggacgact ccaagtccac cgtgtacctg      240
aagatgaact ccctgaaaac cgaggacacc gccatctact actgcgcccg gtactactac      300
ggcatggact actggggcca gggcacctcc gtgaccgtgt cctca                      345
```

<210> SEQ ID NO 20
<211> LENGTH: 345
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)...(345)
<223> OTHER INFORMATION: nucleotide sequence encoding VH2 heavy chain
      amino acid sequence

<400> SEQUENCE: 20

```
caggtgcagc tgcaggaatc cggccctggc ctggtcaagc cctccgagac actgtccctg      60
acctgcaccg tgtccggctt ctccctgctg tcctacggcg tgcactgggt ccgacagcct     120
ccaggcaaag gcctggaatg gctgggcgtg atctggaccg gcggcaccac caactacaac     180
tccgccctga tgtccggct gaccatctcc aaggacgact ccaagaacac cgtgtacctg      240
aagatgaact ccctgaaaac cgaggacacc gccatctact actgcgcccg gtactactac     300
ggcatggact actggggcca gggcaccctg gtcaccgtgt cctca                     345
```

<210> SEQ ID NO 21
<211> LENGTH: 345
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)...(345)
<223> OTHER INFORMATION: nucleotide sequence encoding VH3 heavy chain
      amino acid sequence

<400> SEQUENCE: 21

```
caggtgcagc tgcaggaatc cggccctggc ctggtcaagc cctccgagac actgtccctg      60
acctgcaccg tgtccggctt ctccctgctg tcctacggcg tgcactgggt ccgacagcct     120
ccaggcaaag gcctggaatg gctgggcgtg atctggaccg gcggcaccac caactacaac     180
tccgccctga tgtccggtt caccatctcc aaggacgact ccaagaacac cgtgtacctg      240
aagatgaact ccctgaaaac cgaggacacc gccatctact actgcgcccg gtactactac     300
ggcatggact actggggcca gggcaccctg gtcaccgtgt cctca                     345
```

<210> SEQ ID NO 22
<211> LENGTH: 345
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)...(345)
<223> OTHER INFORMATION: nucleotide sequence encoding VH4 heavy chain
      amino acid sequence

<400> SEQUENCE: 22

```
caggtgcagc tgcaggaatc cggccctggc ctggtcaagc cctccgagac actgtccctg      60
```

```
acctgcaccg tgtccggctt ctccctgctg tcctacggcg tgcactgggt ccgacagcct      120
ccaggcaaag gcctggaatg gctgggcgtg atctggaccg gcggcaccac caactacaac      180
tccgccctga tgtcccggtt caccatctcc aaggacgact ccaagaacac cctgtacctg      240
aagatgaact ccctgaaaac cgaggacacc gccatctact actgcgcccg gtactactac      300
ggcatggact actggggcca gggcaccctg gtcaccgtgt cctca                      345
```

```
<210> SEQ ID NO 23
<211> LENGTH: 321
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)...(321)
<223> OTHER INFORMATION: nucleotide sequence encoding Vk1 light chain
      amino acid sequence

<400> SEQUENCE: 23
```

```
gacatcgtga tgacccagtc ccccagcttc ctgtccgcct ccgtgggcga cagagtgacc      60
atcacatgca aggcctctca ggacgtgcgg aacaccgtgg cctggtatca gcagaaaacc      120
ggcaaggccc ccaagctgct gatctactcc tcctcctacc ggaacaccgg cgtgcccgac      180
cggtttaccg gctctggctc cggcaccgac tttaccctga ccatcagctc cctgcaggcc      240
gaggacgtgg ccgtgtactt ctgccagcag cactacatca ccccctacac cttcggcgga      300
ggcaccaagg tggaaataaa a                                                321
```

```
<210> SEQ ID NO 24
<211> LENGTH: 321
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)...(321)
<223> OTHER INFORMATION: nucleotide sequence encoding Vk2 light chain
      amino acid sequence

<400> SEQUENCE: 24
```

```
gacatcgtga tgacccagtc ccctccagc ctgtccgcct ctgtgggcga cagagtgacc       60
atcacatgca aggcctctca ggacgtgcgg aacaccgtgg cctggtatca gcagaagccc      120
ggcaaggccc ccaagctgct gatctactcc tcctcctacc ggaacaccgg cgtgcccgac      180
cggtttaccg gctctggctc cggcaccgac tttaccctga ccatcagctc cctgcaggcc      240
gaggacgtgg ccgtgtactt ctgccagcag cactacatca ccccctacac cttcggcgga      300
ggcaccaagg tggaaataaa a                                                321
```

```
<210> SEQ ID NO 25
<211> LENGTH: 321
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)...(321)
<223> OTHER INFORMATION: nucleotide sequence encoding Vk3 light chain
      amino acid sequence

<400> SEQUENCE: 25
```

-continued

```
gacatccaga tgacccagtc cccctccagc ctgtccgcct ctgtgggcga cagagtgacc      60
atcacatgca aggcctccca ggacgtgcgg aacaccgtgg cctggtatca gcagaagccc     120
ggcaaggccc ccaagctgct gatctactcc tcctcctacc ggaacaccgg cgtgcccgac     180
cggttctctg gctctggaag cggcaccgac tttaccctga ccatcagctc cctgcaggcc     240
gaggacgtgg ccgtgtactt ctgccagcag cactacatca cccccctacac cttcggcgga     300 ggcaccaagg tggaaataaa a                                                321
```

<210> SEQ ID NO 26
<211> LENGTH: 321
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)...(321)
<223> OTHER INFORMATION: nucleotide sequence encoding Vk4 light chain
      amino acid sequence

<400> SEQUENCE: 26

```
gacatccaga tgacccagtc cccctccagc ctgtccgcct ctgtgggcga cagagtgacc      60
atcacatgca aggcctctca ggacgtgcgg aacaccgtgg cctggtatca gcagaagccc     120
ggcaaggccc ccaagctgct gatctactcc tcctcctacc ggaacaccgg cgtgcccgac     180
cggttctctg gctctggaag cggcaccgac tttaccctga ccatcagctc cctgcaggcc     240
gaggacgtgg ccgtgtacta ctgccagcag cactacatca cccccctacac cttcggcgga     300 ggcaccaagg tggaaataaa a                                                321
```

<210> SEQ ID NO 27
<211> LENGTH: 707
<212> TYPE: PRT
<213> ORGANISM: Homo sapiens
<220> FEATURE:
<221> NAME/KEY: misc_feature
<222> LOCATION: (1)...(707)
<223> OTHER INFORMATION: matrix metalloproteinase 9 (MMP9)
<220> FEATURE:
<221> NAME/KEY: PEPTIDE
<222> LOCATION: (1)...(19)
<223> OTHER INFORMATION: signal peptide
<220> FEATURE:
<221> NAME/KEY: DOMAIN
<222> LOCATION: (38)...(98)
<223> OTHER INFORMATION: peptidoglycan binding domain
<220> FEATURE:
<221> NAME/KEY: SITE
<222> LOCATION: (98)...(99)
<223> OTHER INFORMATION: propeptide cleavage site
<220> FEATURE:
<221> NAME/KEY: DOMAIN
<222> LOCATION: (112)...(445)
<223> OTHER INFORMATION: Zn dependent metalloproteinase domain
<220> FEATURE:
<221> NAME/KEY: DOMAIN
<222> LOCATION: (223)...(271)
<223> OTHER INFORMATION: fibronectin type II domain (gelatin binding
      domain)
<220> FEATURE:
<221> NAME/KEY: DOMAIN
<222> LOCATION: (281)...(329)
<223> OTHER INFORMATION: fibronectin type II domain (gelatin binding
      domain)
<220> FEATURE:
<221> NAME/KEY: DOMAIN
<222> LOCATION: (340)...(388)
<223> OTHER INFORMATION: fibronectin type II domain (gelatin binding
      domain)

```
<220> FEATURE:
<221> NAME/KEY: misc_feature
<222> LOCATION: (400)...(411)
<223> OTHER INFORMATION: Zn binding region
<220> FEATURE:
<221> NAME/KEY: DOMAIN
<222> LOCATION: (521)...(565)
<223> OTHER INFORMATION: hemopexin-like domain
<220> FEATURE:
<221> NAME/KEY: DOMAIN
<222> LOCATION: (567)...(608)
<223> OTHER INFORMATION: hemopexin-like domain
<220> FEATURE:
<221> NAME/KEY: DOMAIN
<222> LOCATION: (613)...(659)
<223> OTHER INFORMATION: hemopexin-like domain
<220> FEATURE:
<221> NAME/KEY: DOMAIN
<222> LOCATION: (661)...(704)
<223> OTHER INFORMATION: hemopexin-like domain

<400> SEQUENCE: 27
```

Met Ser Leu Trp Gln Pro Leu Val Leu Val Leu Leu Val Leu Gly Cys
 1               5                  10                  15

Cys Phe Ala Ala Pro Arg Gln Arg Gln Ser Thr Leu Val Leu Phe Pro
            20                  25                  30

Gly Asp Leu Arg Thr Asn Leu Thr Asp Arg Gln Leu Ala Glu Glu Tyr
        35                  40                  45

Leu Tyr Arg Tyr Gly Tyr Thr Arg Val Ala Glu Met Arg Gly Glu Ser
    50                  55                  60

Lys Ser Leu Gly Pro Ala Leu Leu Leu Gln Lys Gln Leu Ser Leu Leu
65                  70                  75                  80

Pro Glu Thr Gly Glu Leu Asp Ser Ala Thr Leu Lys Ala Met Arg Thr
                85                  90                  95

Pro Arg Cys Gly Val Pro Asp Leu Gly Arg Phe Gln Thr Phe Glu Gly
            100                 105                 110

Asp Leu Lys Trp His His His Asn Ile Thr Tyr Trp Ile Gln Asn Tyr
        115                 120                 125

Ser Glu Asp Leu Pro Arg Ala Val Ile Asp Asp Ala Phe Ala Arg Ala
    130                 135                 140

Phe Ala Leu Trp Ser Ala Val Thr Pro Leu Thr Phe Thr Arg Val Tyr
145                 150                 155                 160

Ser Arg Asp Ala Asp Ile Val Ile Gln Phe Gly Val Ala Glu His Gly
                165                 170                 175

Asp Gly Tyr Pro Phe Asp Gly Lys Asp Gly Leu Leu Ala His Ala Phe
            180                 185                 190

Pro Pro Gly Pro Gly Ile Gln Gly Asp Ala His Phe Asp Asp Asp Glu
        195                 200                 205

Leu Trp Ser Leu Gly Lys Gly Val Val Val Pro Thr Arg Phe Gly Asn
    210                 215                 220

Ala Asp Gly Ala Ala Cys His Phe Pro Phe Ile Phe Glu Gly Arg Ser
225                 230                 235                 240

Tyr Ser Ala Cys Thr Thr Asp Gly Arg Ser Asp Gly Leu Pro Trp Cys
                245                 250                 255

Ser Thr Thr Ala Asn Tyr Asp Thr Asp Asp Arg Phe Gly Phe Cys Pro
            260                 265                 270

Ser Glu Arg Leu Tyr Thr Arg Asp Gly Asn Ala Asp Gly Lys Pro Cys
        275                 280                 285

Gln Phe Pro Phe Ile Phe Gln Gly Gln Ser Tyr Ser Ala Cys Thr Thr
    290                 295                 300

-continued

```
Asp Gly Arg Ser Asp Gly Tyr Arg Trp Cys Ala Thr Thr Ala Asn Tyr
305                 310                 315                 320

Asp Arg Asp Lys Leu Phe Gly Phe Cys Pro Thr Arg Ala Asp Ser Thr
                325                 330                 335

Val Met Gly Gly Asn Ser Ala Gly Glu Leu Cys Val Phe Pro Phe Thr
                340                 345                 350

Phe Leu Gly Lys Glu Tyr Ser Thr Cys Thr Ser Glu Gly Arg Gly Asp
                355                 360                 365

Gly Arg Leu Trp Cys Ala Thr Thr Ser Asn Phe Asp Ser Asp Lys Lys
370                 375                 380

Trp Gly Phe Cys Pro Asp Gln Gly Tyr Ser Leu Phe Leu Val Ala Ala
385                 390                 395                 400

His Glu Phe Gly His Ala Leu Gly Leu Asp His Ser Ser Val Pro Glu
                405                 410                 415

Ala Leu Met Tyr Pro Met Tyr Arg Phe Thr Glu Gly Pro Pro Leu His
                420                 425                 430

Lys Asp Asp Val Asn Gly Ile Arg His Leu Tyr Gly Pro Arg Pro Glu
                435                 440                 445

Pro Glu Pro Arg Pro Pro Thr Thr Thr Pro Gln Pro Thr Ala Pro
450                 455                 460

Pro Thr Val Cys Pro Thr Gly Pro Pro Thr Val His Pro Ser Glu Arg
465                 470                 475                 480

Pro Thr Ala Gly Pro Thr Gly Pro Pro Ser Ala Gly Pro Thr Gly Pro
                485                 490                 495

Pro Thr Ala Gly Pro Ser Thr Ala Thr Thr Val Pro Leu Ser Pro Val
                500                 505                 510

Asp Asp Ala Cys Asn Val Asn Ile Phe Asp Ala Ile Ala Glu Ile Gly
                515                 520                 525

Asn Gln Leu Tyr Leu Phe Lys Asp Gly Lys Tyr Trp Arg Phe Ser Glu
530                 535                 540

Gly Arg Gly Ser Arg Pro Gln Gly Pro Phe Leu Ile Ala Asp Lys Trp
545                 550                 555                 560

Pro Ala Leu Pro Arg Lys Leu Asp Ser Val Phe Glu Glu Pro Leu Ser
                565                 570                 575

Lys Lys Leu Phe Phe Phe Ser Gly Arg Gln Val Trp Val Tyr Thr Gly
                580                 585                 590

Ala Ser Val Leu Gly Pro Arg Arg Leu Asp Lys Leu Gly Leu Gly Ala
                595                 600                 605

Asp Val Ala Gln Val Thr Gly Ala Leu Arg Ser Gly Arg Gly Lys Met
                610                 615                 620

Leu Leu Phe Ser Gly Arg Arg Leu Trp Arg Phe Asp Val Lys Ala Gln
625                 630                 635                 640

Met Val Asp Pro Arg Ser Ala Ser Glu Val Asp Arg Met Phe Pro Gly
                645                 650                 655

Val Pro Leu Asp Thr His Asp Val Phe Gln Tyr Arg Glu Lys Ala Tyr
                660                 665                 670

Phe Cys Gln Asp Arg Phe Tyr Trp Arg Val Ser Ser Arg Ser Glu Leu
                675                 680                 685

Asn Gln Val Asp Gln Val Gly Tyr Val Thr Tyr Asp Ile Leu Gln Cys
                690                 695                 700

Pro Glu Asp
705
```

<210> SEQ ID NO 28
<211> LENGTH: 688
<212> TYPE: PRT
<213> ORGANISM: Homo sapiens
<220> FEATURE:
<221> NAME/KEY: misc_feature
<222> LOCATION: (1)...(688)
<223> OTHER INFORMATION: mature full-length matrix metalloproteinase 9
    (MMP9)

<400> SEQUENCE: 28

```
Ala Pro Arg Gln Arg Gln Ser Thr Leu Val Leu Phe Pro Gly Asp Leu
 1               5                  10                  15

Arg Thr Asn Leu Thr Asp Arg Gln Leu Ala Glu Glu Tyr Leu Tyr Arg
            20                  25                  30

Tyr Gly Tyr Thr Arg Val Ala Glu Met Arg Gly Glu Ser Lys Ser Leu
        35                  40                  45

Gly Pro Ala Leu Leu Leu Leu Gln Lys Gln Leu Ser Leu Pro Glu Thr
    50                  55                  60

Gly Glu Leu Asp Ser Ala Thr Leu Lys Ala Met Arg Thr Pro Arg Cys
65                  70                  75                  80

Gly Val Pro Asp Leu Gly Arg Phe Gln Thr Phe Glu Gly Asp Leu Lys
                85                  90                  95

Trp His His Asn Ile Thr Tyr Trp Ile Gln Asn Tyr Ser Glu Asp
            100                 105                 110

Leu Pro Arg Ala Val Ile Asp Asp Ala Phe Ala Arg Ala Phe Ala Leu
        115                 120                 125

Trp Ser Ala Val Thr Pro Leu Thr Phe Thr Arg Val Tyr Ser Arg Asp
    130                 135                 140

Ala Asp Ile Val Ile Gln Phe Gly Val Ala Glu His Gly Asp Gly Tyr
145                 150                 155                 160

Pro Phe Asp Gly Lys Asp Gly Leu Leu Ala His Ala Phe Pro Pro Gly
                165                 170                 175

Pro Gly Ile Gln Gly Asp Ala His Phe Asp Asp Glu Leu Trp Ser
            180                 185                 190

Leu Gly Lys Gly Val Val Val Pro Thr Arg Phe Gly Asn Ala Asp Gly
        195                 200                 205

Ala Ala Cys His Phe Pro Phe Ile Phe Glu Gly Arg Ser Tyr Ser Ala
    210                 215                 220

Cys Thr Thr Asp Gly Arg Ser Asp Gly Leu Pro Trp Cys Ser Thr Thr
225                 230                 235                 240

Ala Asn Tyr Asp Thr Asp Arg Phe Gly Phe Cys Pro Ser Glu Arg
                245                 250                 255

Leu Tyr Thr Arg Asp Gly Asn Ala Asp Gly Lys Pro Cys Gln Phe Pro
            260                 265                 270

Phe Ile Phe Gln Gly Gln Ser Tyr Ser Ala Cys Thr Thr Asp Gly Arg
        275                 280                 285

Ser Asp Gly Tyr Arg Trp Cys Ala Thr Thr Ala Asn Tyr Asp Arg Asp
    290                 295                 300

Lys Leu Phe Gly Phe Cys Pro Thr Arg Ala Asp Ser Thr Val Met Gly
305                 310                 315                 320

Gly Asn Ser Ala Gly Glu Leu Cys Val Phe Pro Phe Thr Phe Leu Gly
                325                 330                 335

Lys Glu Tyr Ser Thr Cys Thr Ser Glu Gly Arg Gly Asp Gly Arg Leu
            340                 345                 350
```

```
            Trp Cys Ala Thr Thr Ser Asn Phe Asp Ser Asp Lys Lys Trp Gly Phe
                        355                 360                 365

Cys Pro Asp Gln Gly Tyr Ser Leu Phe Leu Val Ala Ala His Glu Phe
                370                 375                 380

Gly His Ala Leu Gly Leu Asp His Ser Ser Val Pro Glu Ala Leu Met
            385                 390                 395                 400

Tyr Pro Met Tyr Arg Phe Thr Glu Gly Pro Pro Leu His Lys Asp Asp
                            405                 410                 415

Val Asn Gly Ile Arg His Leu Tyr Gly Pro Arg Pro Glu Pro Glu Pro
                        420                 425                 430

Arg Pro Pro Thr Thr Thr Thr Pro Gln Pro Thr Ala Pro Pro Thr Val
                    435                 440                 445

Cys Pro Thr Gly Pro Pro Thr Val His Pro Ser Glu Arg Pro Thr Ala
                        450                 455                 460

Gly Pro Thr Gly Pro Pro Ser Ala Gly Pro Thr Gly Pro Pro Thr Ala
            465                 470                 475                 480

Gly Pro Ser Thr Ala Thr Thr Val Pro Leu Ser Pro Val Asp Asp Ala
                            485                 490                 495

Cys Asn Val Asn Ile Phe Asp Ala Ile Ala Glu Ile Gly Asn Gln Leu
                        500                 505                 510

Tyr Leu Phe Lys Asp Gly Lys Tyr Trp Arg Phe Ser Glu Gly Arg Gly
                    515                 520                 525

Ser Arg Pro Gln Gly Pro Phe Leu Ile Ala Asp Lys Trp Pro Ala Leu
                        530                 535                 540

Pro Arg Lys Leu Asp Ser Val Phe Glu Glu Pro Leu Ser Lys Lys Leu
            545                 550                 555                 560

Phe Phe Phe Ser Gly Arg Gln Val Trp Val Tyr Thr Gly Ala Ser Val
                            565                 570                 575

Leu Gly Pro Arg Arg Leu Asp Lys Leu Gly Leu Gly Ala Asp Val Ala
                        580                 585                 590

Gln Val Thr Gly Ala Leu Arg Ser Gly Arg Gly Lys Met Leu Leu Phe
                    595                 600                 605

Ser Gly Arg Arg Leu Trp Arg Phe Asp Val Lys Ala Gln Met Val Asp
            610                 615                 620

Pro Arg Ser Ala Ser Glu Val Asp Arg Met Phe Pro Gly Val Pro Leu
            625                 630                 635                 640

Asp Thr His Asp Val Phe Gln Tyr Arg Glu Lys Ala Tyr Phe Cys Gln
                            645                 650                 655

Asp Arg Phe Tyr Trp Arg Val Ser Ser Arg Ser Glu Leu Asn Gln Val
                        660                 665                 670

Asp Gln Val Gly Tyr Val Thr Tyr Asp Ile Leu Gln Cys Pro Glu Asp
                    675                 680                 685

<210> SEQ ID NO 29
<211> LENGTH: 19
<212> TYPE: PRT
<213> ORGANISM: Homo sapiens

<400> SEQUENCE: 29

Met Ser Leu Trp Gln Pro Leu Val Leu Val Leu Leu Val Leu Gly Cys
 1               5                  10                  15

Cys Phe Ala

<210> SEQ ID NO 30
<211> LENGTH: 470
```

```
<212> TYPE: PRT
<213> ORGANISM: Mus musculus
<220> FEATURE:
<221> NAME/KEY: CHAIN
<222> LOCATION: (1)...(470)
<223> OTHER INFORMATION: M4 heavy chain (IgG2b)

<400> SEQUENCE: 30
```

Met Ala Val Leu Val Leu Phe Leu Cys Leu Ala Phe Pro Ser Cys
 1               5                  10                  15

Val Leu Ser Gln Val Gln Leu Lys Glu Ser Gly Pro Gly Leu Val Ala
             20                  25                  30

Pro Ser Gln Ser Leu Ser Ile Thr Cys Thr Val Ser Gly Phe Ser Leu
             35                  40                  45

Leu Ser Tyr Gly Val His Trp Val Arg Gln Pro Pro Gly Lys Gly Leu
         50                  55                  60

Glu Trp Leu Gly Val Ile Trp Thr Gly Gly Ser Thr Asn Tyr Asn Ser
 65                  70                  75                  80

Ala Leu Met Ser Arg Leu Ser Ile Ser Lys Asp Asp Ser Lys Ser Gln
                 85                  90                  95

Val Phe Leu Lys Met Asn Ser Leu Gln Thr Asp Asp Thr Ala Met Tyr
            100                 105                 110

Tyr Cys Ala Arg Tyr Tyr Ala Met Asp Tyr Trp Gly Gln Gly Thr
        115                 120                 125

Ser Val Thr Val Ser Ser Ala Lys Thr Thr Pro Pro Ser Val Tyr Pro
    130                 135                 140

Leu Ala Pro Gly Cys Gly Asp Thr Thr Gly Ser Ser Val Thr Leu Gly
145                 150                 155                 160

Cys Leu Val Lys Gly Tyr Phe Pro Glu Ser Val Thr Val Thr Trp Asn
                165                 170                 175

Ser Gly Ser Leu Ser Ser Ser Val His Thr Phe Pro Ala Leu Leu Gln
            180                 185                 190

Ser Gly Leu Tyr Thr Met Ser Ser Ser Val Thr Val Pro Ser Ser Thr
        195                 200                 205

Trp Pro Ser Gln Thr Val Thr Cys Ser Val Ala His Pro Ala Ser Ser
210                 215                 220

Thr Thr Val Asp Lys Lys Leu Glu Pro Ser Gly Pro Ile Ser Thr Ile
225                 230                 235                 240

Asn Pro Cys Pro Pro Cys Lys Glu Cys His Lys Cys Pro Ala Pro Asn
                245                 250                 255

Leu Glu Gly Gly Pro Ser Val Phe Ile Phe Pro Pro Asn Ile Lys Asp
            260                 265                 270

Val Leu Met Ile Ser Leu Thr Pro Lys Val Thr Cys Val Val Val Asp
        275                 280                 285

Val Ser Glu Asp Asp Pro Asp Val Arg Ile Ser Trp Phe Val Asn Asn
    290                 295                 300

Val Glu Val His Thr Ala Gln Thr Gln Thr His Arg Glu Asp Tyr Asn
305                 310                 315                 320

Ser Thr Ile Arg Val Val Ser Ala Leu Pro Ile Gln His Gln Asp Trp
                325                 330                 335

Met Ser Gly Lys Glu Phe Lys Cys Lys Val Asn Asn Lys Asp Leu Pro
            340                 345                 350

Ser Pro Ile Glu Arg Thr Ile Ser Lys Ile Lys Gly Leu Val Arg Ala
        355                 360                 365

Pro Gln Val Tyr Ile Leu Pro Pro Pro Ala Glu Gln Leu Ser Arg Lys

```
                    370                 375                 380
Asp Val Ser Leu Thr Cys Leu Val Val Gly Phe Asn Pro Gly Asp Ile
385                 390                 395                 400

Ser Val Glu Trp Thr Ser Asn Gly His Thr Glu Glu Asn Tyr Lys Asp
                    405                 410                 415

Thr Ala Pro Val Leu Asp Ser Asp Gly Ser Tyr Phe Ile Tyr Ser Lys
                    420                 425                 430

Leu Asp Ile Lys Thr Ser Lys Trp Glu Lys Thr Asp Ser Phe Ser Cys
                    435                 440                 445

Asn Val Arg His Glu Gly Leu Lys Asn Tyr Tyr Leu Lys Lys Thr Ile
                    450                 455                 460

Ser Arg Ser Pro Gly Lys
465                 470

<210> SEQ ID NO 31
<211> LENGTH: 234
<212> TYPE: PRT
<213> ORGANISM: Mus musculus
<220> FEATURE:
<221> NAME/KEY: CHAIN
<222> LOCATION: (1)...(234)
<223> OTHER INFORMATION: M4 light chain (kappa)

<400> SEQUENCE: 31

Met Glu Ser Gln Ile Gln Val Phe Val Phe Val Phe Leu Trp Leu Ser
  1               5                  10                  15

Gly Val Asp Gly Asp Ile Val Met Thr Gln Ser His Lys Phe Met Phe
                 20                  25                  30

Thr Ser Val Gly Asp Arg Val Ser Ile Thr Cys Lys Ala Ser Gln Asp
                 35                  40                  45

Val Arg Asn Thr Val Ala Trp Tyr Gln Gln Lys Thr Gly Gln Ser Pro
 50                  55                  60

Lys Leu Leu Ile Tyr Ser Ala Ser Tyr Arg Asn Thr Gly Val Pro Asp
 65                  70                  75                  80

Arg Phe Thr Gly Ser Ile Ser Gly Thr Asp Phe Thr Phe Thr Ile Ser
                 85                  90                  95

Ser Val Gln Ala Glu Asp Leu Ala Leu Tyr Tyr Cys Gln Gln His Tyr
                100                 105                 110

Ser Thr Pro Tyr Thr Phe Gly Gly Gly Thr Lys Leu Glu Val Lys Arg
                115                 120                 125

Ala Asp Ala Ala Pro Thr Val Ser Ile Phe Pro Pro Ser Ser Glu Gln
130                 135                 140

Leu Thr Ser Gly Gly Ala Ser Val Val Cys Phe Leu Asn Asn Phe Tyr
145                 150                 155                 160

Pro Lys Asp Ile Asn Val Lys Trp Lys Ile Asp Gly Ser Glu Arg Gln
                165                 170                 175

Asn Gly Val Leu Asn Ser Trp Thr Asp Gln Asp Ser Lys Asp Ser Thr
                180                 185                 190

Tyr Ser Met Ser Ser Thr Leu Thr Leu Thr Lys Asp Glu Tyr Glu Arg
                195                 200                 205

His Asn Ser Tyr Thr Cys Glu Ala Thr His Lys Thr Ser Thr Ser Pro
                210                 215                 220

Ile Val Lys Ser Phe Asn Arg Asn Glu Cys
225                 230

<210> SEQ ID NO 32
```

```
<211> LENGTH: 115
<212> TYPE: PRT
<213> ORGANISM: Mus musculus

<400> SEQUENCE: 32

Gln Val Gln Leu Lys Glu Ser Gly Pro Gly Leu Val Ala Pro Ser Gln
 1               5                  10                  15

Ser Leu Ser Ile Thr Cys Thr Val Ser Gly Phe Ser Leu Leu Ser Tyr
            20                  25                  30

Gly Val His Trp Val Arg Gln Pro Pro Gly Lys Gly Leu Glu Trp Leu
        35                  40                  45

Gly Val Ile Trp Thr Gly Gly Ser Thr Asn Tyr Asn Ser Ala Leu Met
    50                  55                  60

Ser Arg Leu Ser Ile Ser Lys Asp Asp Ser Lys Ser Gln Val Phe Leu
65                  70                  75                  80

Lys Met Asn Ser Leu Gln Thr Asp Asp Thr Ala Met Tyr Tyr Cys Ala
                85                  90                  95

Arg Tyr Tyr Tyr Ala Met Asp Tyr Trp Gly Gln Gly Thr Ser Val Thr
            100                 105                 110

Val Ser Ser
        115

<210> SEQ ID NO 33
<211> LENGTH: 107
<212> TYPE: PRT
<213> ORGANISM: Mus musculus

<400> SEQUENCE: 33

Asp Ile Val Met Thr Gln Ser His Lys Phe Met Phe Thr Ser Val Gly
 1               5                  10                  15

Asp Arg Val Ser Ile Thr Cys Lys Ala Ser Gln Asp Val Arg Asn Thr
            20                  25                  30

Val Ala Trp Tyr Gln Gln Lys Thr Gly Gln Ser Pro Lys Leu Leu Ile
        35                  40                  45

Tyr Ser Ala Ser Tyr Arg Asn Thr Gly Val Pro Asp Arg Phe Thr Gly
    50                  55                  60

Ser Ile Ser Gly Thr Asp Phe Thr Phe Thr Ile Ser Ser Val Gln Ala
65                  70                  75                  80

Glu Asp Leu Ala Leu Tyr Tyr Cys Gln Gln His Tyr Ser Thr Pro Tyr
                85                  90                  95

Thr Phe Gly Gly Gly Thr Lys Leu Glu Val Lys
            100                 105

<210> SEQ ID NO 34
<211> LENGTH: 10
<212> TYPE: PRT
<213> ORGANISM: Mus musculus

<400> SEQUENCE: 34

Gly Phe Ser Leu Leu Ser Tyr Gly Val His
 1               5                  10

<210> SEQ ID NO 35
<211> LENGTH: 10
<212> TYPE: PRT
<213> ORGANISM: Mus musculus

<400> SEQUENCE: 35

Val Ile Trp Thr Gly Gly Ser Thr Asn Tyr
```

<210> SEQ ID NO 36
<211> LENGTH: 7
<212> TYPE: PRT
<213> ORGANISM: Mus musculus

<400> SEQUENCE: 36

Tyr Tyr Tyr Ala Met Asp Tyr
1               5

<210> SEQ ID NO 37
<211> LENGTH: 11
<212> TYPE: PRT
<213> ORGANISM: Mus musculus

<400> SEQUENCE: 37

Lys Ala Ser Gln Asp Val Arg Asn Thr Val Ala
1               5                   10

<210> SEQ ID NO 38
<211> LENGTH: 7
<212> TYPE: PRT
<213> ORGANISM: Mus musculus

<400> SEQUENCE: 38

Ser Ala Ser Tyr Arg Asn Thr
1               5

<210> SEQ ID NO 39
<211> LENGTH: 9
<212> TYPE: PRT
<213> ORGANISM: Mus musculus

<400> SEQUENCE: 39

Gln Gln His Tyr Ser Thr Pro Tyr Thr
1               5

<210> SEQ ID NO 40
<211> LENGTH: 229
<212> TYPE: PRT
<213> ORGANISM: Mus musculus
<220> FEATURE:
<221> NAME/KEY: CHAIN
<222> LOCATION: (1)...(229)
<223> OTHER INFORMATION: M12 kappa chain

<400> SEQUENCE: 40

Gln Val Phe Val Tyr Met Leu Leu Trp Leu Ser Gly Val Asp Gly Asp
1               5                   10                  15

Ile Val Met Thr Gln Ser Gln Lys Phe Met Ser Thr Ser Val Gly Asp
                20                  25                  30

Arg Val Ser Val Thr Cys Lys Ala Ser Gln Asn Val Gly Thr Asn Val
            35                  40                  45

Ala Trp Tyr Gln Gln Lys Pro Gly Gln Ser Pro Lys Ala Leu Ile Tyr
        50                  55                  60

Ser Ala Ser Tyr Arg Phe Ser Gly Val Pro Asp Arg Phe Thr Gly Ser
65                  70                  75                  80

Gly Ser Gly Thr Asp Phe Thr Leu Thr Ile Ser Asn Val Gln Ser Glu
                85                  90                  95

Asp Leu Ala Glu Tyr Phe Cys Gln Gln Tyr Asn Ser Tyr Pro Tyr Thr
            100                 105                 110

```
Phe Gly Gly Gly Thr Lys Leu Glu Ile Lys Arg Ala Asp Ala Ala Pro
            115                 120                 125
Thr Val Ser Ile Phe Pro Pro Ser Ser Glu Gln Leu Thr Ser Gly Gly
        130                 135                 140
Ala Ser Val Val Cys Phe Leu Asn Asn Phe Tyr Pro Lys Asp Ile Asn
145                 150                 155                 160
Val Lys Trp Lys Ile Asp Gly Ser Glu Arg Gln Asn Gly Val Leu Asn
                165                 170                 175
Ser Trp Thr Asp Gln Asp Ser Lys Asp Ser Thr Tyr Ser Met Ser Ser
            180                 185                 190
Thr Leu Thr Leu Thr Lys Asp Glu Tyr Glu Arg His Asn Ser Tyr Thr
        195                 200                 205
Cys Glu Ala Thr His Lys Thr Ser Thr Ser Pro Ile Val Lys Ser Phe
    210                 215                 220
Asn Arg Asn Glu Cys
225
```

<210> SEQ ID NO 41
<211> LENGTH: 107
<212> TYPE: PRT
<213> ORGANISM: Mus musculus

<400> SEQUENCE: 41

```
Asp Ile Val Met Thr Gln Ser Gln Lys Phe Met Ser Thr Ser Val Gly
1               5                   10                  15
Asp Arg Val Ser Val Thr Cys Lys Ala Ser Gln Asn Val Gly Thr Asn
            20                  25                  30
Val Ala Trp Tyr Gln Gln Lys Pro Gly Gln Ser Pro Lys Ala Leu Ile
        35                  40                  45
Tyr Ser Ala Ser Tyr Arg Phe Ser Gly Val Pro Asp Arg Phe Thr Gly
    50                  55                  60
Ser Gly Ser Gly Thr Asp Phe Thr Leu Thr Ile Ser Asn Val Gln Ser
65                  70                  75                  80
Glu Asp Leu Ala Glu Tyr Phe Cys Gln Gln Tyr Asn Ser Tyr Pro Tyr
                85                  90                  95
Thr Phe Gly Gly Gly Thr Lys Leu Glu Ile Lys
            100                 105
```

<210> SEQ ID NO 42
<211> LENGTH: 11
<212> TYPE: PRT
<213> ORGANISM: Mus musculus

<400> SEQUENCE: 42

```
Lys Ala Ser Gln Asn Val Gly Thr Asn Val Ala
1               5                   10
```

<210> SEQ ID NO 43
<211> LENGTH: 7
<212> TYPE: PRT
<213> ORGANISM: Mus musculus

<400> SEQUENCE: 43

```
Ser Ala Ser Tyr Arg Phe Ser
1               5
```

<210> SEQ ID NO 44
<211> LENGTH: 9
<212> TYPE: PRT

```
<213> ORGANISM: Mus musculus

<400> SEQUENCE: 44

Gln Gln Tyr Asn Ser Tyr Pro Tyr Thr
1               5

<210> SEQ ID NO 45
<211> LENGTH: 233
<212> TYPE: PRT
<213> ORGANISM: Mus musculus
<220> FEATURE:
<221> NAME/KEY: CHAIN
<222> LOCATION: (1)...(233)
<223> OTHER INFORMATION: AB0046 kappa light chain

<400> SEQUENCE: 45

Met Ser Ser Ala Gln Phe Leu Gly Leu Leu Leu Cys Phe Gln Gly
1               5                   10                  15

Thr Arg Cys Asp Ile Gln Met Thr Gln Thr Thr Ser Ser Leu Ser Ala
                20                  25                  30

Ser Leu Gly Asp Arg Val Thr Ile Ser Cys Ser Ala Ser Gln Gly Ile
            35                  40                  45

Ser Asn Tyr Leu Asn Trp Tyr Gln Gln Lys Pro Asp Gly Thr Phe Lys
50                  55                  60

Leu Leu Ile Tyr Tyr Thr Ser Ile Leu His Ser Gly Val Pro Ser Arg
65                  70                  75                  80

Phe Ser Gly Ser Gly Ser Gly Thr Asp Tyr Ser Leu Thr Ile Ser Asn
                85                  90                  95

Leu Glu Pro Glu Asp Ile Ala Thr Tyr Tyr Cys Gln Gln Tyr Gly Trp
            100                 105                 110

Leu Pro Arg Thr Phe Gly Gly Gly Thr Lys Leu Glu Ile Lys Arg Ala
        115                 120                 125

Asp Ala Ala Pro Thr Val Ser Ile Phe Pro Pro Ser Ser Glu Gln Leu
    130                 135                 140

Thr Ser Gly Gly Ala Ser Val Val Cys Phe Leu Asn Asn Phe Tyr Pro
145                 150                 155                 160

Lys Asp Ile Asn Val Lys Trp Lys Ile Asp Gly Ser Glu Arg Gln Asn
                165                 170                 175

Gly Val Leu Asn Ser Trp Thr Asp Gln Asp Ser Lys Asp Ser Thr Tyr
            180                 185                 190

Ser Met Ser Ser Thr Leu Thr Leu Thr Lys Asp Glu Tyr Glu Arg His
        195                 200                 205

Asn Ser Tyr Thr Cys Glu Ala Thr His Lys Thr Ser Thr Ser Pro Ile
    210                 215                 220

Val Lys Ser Phe Asn Arg Asn Glu Cys
225                 230

<210> SEQ ID NO 46
<211> LENGTH: 460
<212> TYPE: PRT
<213> ORGANISM: Mus musculus
<220> FEATURE:
<221> NAME/KEY: CHAIN
<222> LOCATION: (1)...(460)
<223> OTHER INFORMATION: AB0046 IgG1 heavy chain

<400> SEQUENCE: 46

Met Gly Trp Ser Ser Ile Ile Leu Phe Leu Val Ala Thr Ala Thr Gly
1               5                   10                  15
```

-continued

```
Val His Ser Gln Val Gln Leu Gln Gln Pro Gly Ser Val Leu Val Arg
             20                  25                  30

Pro Gly Ala Ser Val Lys Leu Ser Cys Thr Ala Ser Gly Tyr Thr Phe
         35                  40                  45

Thr Ser Tyr Trp Met Asn Trp Val Lys Gln Arg Pro Gly Gln Gly Leu
     50                  55                  60

Glu Trp Ile Gly Glu Ile Tyr Pro Ile Ser Gly Arg Thr Asn Tyr Asn
 65                  70                  75                  80

Glu Lys Phe Lys Val Lys Ala Thr Leu Thr Val Asp Thr Ser Ser Ser
                 85                  90                  95

Thr Ala Tyr Met Asp Leu Asn Ser Leu Thr Ser Glu Asp Ser Ala Val
            100                 105                 110

Tyr Tyr Cys Ala Arg Ser Arg Ala Asn Trp Asp Asp Tyr Trp Gly Gln
        115                 120                 125

Gly Thr Thr Leu Thr Val Ser Ser Ala Lys Thr Thr Pro Pro Ser Val
    130                 135                 140

Tyr Pro Leu Ala Pro Gly Ser Ala Ala Gln Thr Asn Ser Met Val Thr
145                 150                 155                 160

Leu Gly Cys Leu Val Lys Gly Tyr Phe Pro Glu Pro Val Thr Val Thr
                165                 170                 175

Trp Asn Ser Gly Ser Leu Ser Ser Gly Val His Thr Phe Pro Ala Val
            180                 185                 190

Leu Gln Ser Asp Leu Tyr Thr Leu Ser Ser Ser Val Thr Val Pro Ser
        195                 200                 205

Ser Thr Trp Pro Ser Glu Thr Val Thr Cys Asn Val Ala His Pro Ala
    210                 215                 220

Ser Ser Thr Lys Val Asp Lys Lys Ile Val Pro Arg Asp Cys Gly Cys
225                 230                 235                 240

Lys Pro Cys Ile Cys Thr Val Pro Glu Val Ser Ser Val Phe Ile Phe
                245                 250                 255

Pro Pro Lys Pro Lys Asp Val Leu Thr Ile Thr Leu Thr Pro Lys Val
            260                 265                 270

Thr Cys Val Val Asp Ile Ser Lys Asp Asp Pro Glu Val Gln Phe
        275                 280                 285

Ser Trp Phe Val Asp Asp Val Glu Val His Thr Ala Gln Thr Gln Pro
    290                 295                 300

Arg Glu Glu Gln Phe Asn Ser Thr Phe Arg Ser Val Ser Glu Leu Pro
305                 310                 315                 320

Ile Met His Gln Asp Trp Leu Asn Gly Lys Glu Phe Lys Cys Arg Val
                325                 330                 335

Asn Ser Ala Ala Phe Pro Ala Pro Ile Glu Lys Thr Ile Ser Lys Thr
            340                 345                 350

Lys Gly Arg Pro Lys Ala Pro Gln Val Tyr Thr Ile Pro Pro Pro Lys
        355                 360                 365

Glu Gln Met Ala Lys Asp Lys Val Ser Leu Thr Cys Met Ile Thr Asp
    370                 375                 380

Phe Phe Pro Glu Asp Ile Thr Val Glu Trp Gln Trp Asn Gly Gln Pro
385                 390                 395                 400

Ala Glu Asn Tyr Lys Asn Thr Gln Pro Ile Met Asp Thr Asp Gly Ser
                405                 410                 415

Tyr Phe Val Tyr Ser Lys Leu Asn Val Gln Lys Ser Asn Trp Glu Ala
            420                 425                 430

Gly Asn Thr Phe Thr Cys Ser Val Leu His Glu Gly Leu His Asn His
```

His Thr Glu Lys Ser Leu Ser His Ser Pro Gly Lys
    450                 455                 460

<210> SEQ ID NO 47
<211> LENGTH: 117
<212> TYPE: PRT
<213> ORGANISM: Mus musculus

<400> SEQUENCE: 47

Gln Val Gln Leu Gln Gln Pro Gly Ser Val Leu Val Arg Pro Gly Ala
  1               5                  10                  15

Ser Val Lys Leu Ser Cys Thr Ala Ser Gly Tyr Thr Phe Thr Ser Tyr
             20                  25                  30

Trp Met Asn Trp Val Lys Gln Arg Pro Gly Gln Gly Leu Glu Trp Ile
         35                  40                  45

Gly Glu Ile Tyr Pro Ile Ser Gly Arg Thr Asn Tyr Asn Glu Lys Phe
     50                  55                  60

Lys Val Lys Ala Thr Leu Thr Val Asp Thr Ser Ser Ser Thr Ala Tyr
 65                  70                  75                  80

Met Asp Leu Asn Ser Leu Thr Ser Glu Asp Ser Ala Val Tyr Tyr Cys
                 85                  90                  95

Ala Arg Ser Arg Ala Asn Trp Asp Asp Tyr Trp Gly Gln Gly Thr Thr
            100                 105                 110

Leu Thr Val Ser Ser
        115

<210> SEQ ID NO 48
<211> LENGTH: 107
<212> TYPE: PRT
<213> ORGANISM: Mus musculus

<400> SEQUENCE: 48

Asp Ile Gln Met Thr Gln Thr Thr Ser Ser Leu Ser Ala Ser Leu Gly
  1               5                  10                  15

Asp Arg Val Thr Ile Ser Cys Ser Ala Ser Gln Gly Ile Ser Asn Tyr
             20                  25                  30

Leu Asn Trp Tyr Gln Gln Lys Pro Asp Gly Thr Phe Lys Leu Leu Ile
         35                  40                  45

Tyr Tyr Thr Ser Ile Leu His Ser Gly Val Pro Ser Arg Phe Ser Gly
     50                  55                  60

Ser Gly Ser Gly Thr Asp Tyr Ser Leu Thr Ile Ser Asn Leu Glu Pro
 65                  70                  75                  80

Glu Asp Ile Ala Thr Tyr Tyr Cys Gln Gln Tyr Gly Trp Leu Pro Arg
                 85                  90                  95

Thr Phe Gly Gly Gly Thr Lys Leu Glu Ile Lys
            100                 105

<210> SEQ ID NO 49
<211> LENGTH: 461
<212> TYPE: PRT
<213> ORGANISM: Artificial Sequence
<220> FEATURE:
<223> OTHER INFORMATION: synthetic construct
<220> FEATURE:
<221> NAME/KEY: CHAIN
<222> LOCATION: (1)...(461)
<223> OTHER INFORMATION: AB0045 heavy chain

<400> SEQUENCE: 49

```
Met Gly Trp Ser Leu Ile Leu Leu Phe Leu Val Ala Val Ala Thr Arg
1               5                   10                  15

Val His Ser Gln Val Gln Leu Gln Glu Ser Gly Pro Gly Leu Val Lys
            20                  25                  30

Pro Ser Glu Thr Leu Ser Leu Thr Cys Thr Val Ser Gly Phe Ser Leu
        35                  40                  45

Leu Ser Tyr Gly Val His Trp Val Arg Gln Pro Pro Gly Lys Gly Leu
    50                  55                  60

Glu Trp Leu Gly Val Ile Trp Thr Gly Gly Thr Thr Asn Tyr Asn Ser
65                  70                  75                  80

Ala Leu Met Ser Arg Phe Thr Ile Ser Lys Asp Asp Ser Lys Asn Thr
                85                  90                  95

Val Tyr Leu Lys Met Asn Ser Leu Lys Thr Glu Asp Thr Ala Ile Tyr
            100                 105                 110

Tyr Cys Ala Arg Tyr Tyr Gly Met Asp Tyr Trp Gly Gln Gly Thr
        115                 120                 125

Leu Val Thr Val Ser Ser Ala Ser Thr Lys Gly Pro Ser Val Phe Pro
    130                 135                 140

Leu Ala Pro Cys Ser Arg Ser Thr Ser Glu Ser Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Ser Leu Gly Thr Lys Thr Tyr Thr Cys Asn Val Asp His Lys Pro Ser
    210                 215                 220

Asn Thr Lys Val Asp Lys Arg Val Glu Ser Lys Tyr Gly Pro Pro Cys
225                 230                 235                 240

Pro Pro Cys Pro Ala Pro Glu Phe Leu Gly Gly Pro Ser Val Phe Leu
                245                 250                 255

Phe Pro Pro Lys Pro Lys Asp Thr Leu Met Ile Ser Arg Thr Pro Glu
            260                 265                 270

Val Thr Cys Val Val Val Asp Val Ser Gln Glu Asp Pro Glu Val Gln
        275                 280                 285

Phe Asn Trp Tyr Val Asp Gly Val Glu Val His Asn Ala Lys Thr Lys
    290                 295                 300

Pro Arg Glu Glu Gln Phe Asn Ser Thr Tyr Arg Val Val Ser Val Leu
305                 310                 315                 320

Thr Val Leu His Gln Asp Trp Leu Asn Gly Lys Glu Tyr Lys Cys Lys
                325                 330                 335

Val Ser Asn Lys Gly Leu Pro Ser Ser Ile Glu Lys Thr Ile Ser Lys
            340                 345                 350

Ala Lys Gly Gln Pro Arg Glu Pro Gln Val Tyr Thr Leu Pro Pro Ser
        355                 360                 365

Gln Glu Glu Met Thr Lys Asn Gln Val Ser Leu Thr Cys Leu Val Lys
    370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Val Leu Asp Ser Asp Gly
                405                 410                 415
```

-continued

```
Ser Phe Phe Leu Tyr Ser Arg Leu Thr Val Asp Lys Ser Arg Trp Gln
                420                 425                 430

Glu Gly Asn Val Phe Ser Cys Ser Val Met His Glu Ala Leu His Asn
            435                 440                 445

His Tyr Thr Gln Lys Ser Leu Ser Leu Ser Leu Gly Lys
        450                 455                 460

<210> SEQ ID NO 50
<211> LENGTH: 234
<212> TYPE: PRT
<213> ORGANISM: Artificial Sequence
<220> FEATURE:
<223> OTHER INFORMATION: synthetic construct
<220> FEATURE:
<221> NAME/KEY: CHAIN
<222> LOCATION: (1)...(234)
<223> OTHER INFORMATION: AB0045 light chain

<400> SEQUENCE: 50

Met Arg Val Pro Ala Gln Leu Leu Gly Leu Leu Leu Leu Trp Leu Pro
 1               5                  10                  15

Gly Ala Arg Cys Asp Ile Gln Met Thr Gln Ser Pro Ser Ser Leu Ser
            20                  25                  30

Ala Ser Val Gly Asp Arg Val Thr Ile Thr Cys Lys Ala Ser Gln Asp
        35                  40                  45

Val Arg Asn Thr Val Ala Trp Tyr Gln Gln Lys Pro Gly Lys Ala Pro
    50                  55                  60

Lys Leu Leu Ile Tyr Ser Ser Tyr Arg Asn Thr Gly Val Pro Asp
65                  70                  75                  80

Arg Phe Ser Gly Ser Gly Ser Gly Thr Asp Phe Thr Leu Thr Ile Ser
                85                  90                  95

Ser Leu Gln Ala Glu Asp Val Ala Val Tyr Tyr Cys Gln His Tyr
            100                 105                 110

Ile Thr Pro Tyr Thr Phe Gly Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```